(12) United States Patent
Pamukcu et al.

(10) Patent No.: US 6,358,992 B1
(45) Date of Patent: Mar. 19, 2002

(54) METHOD OF INHIBITING NEOPLASTIC CELLS WITH INDOLE DERIVATIVES

(75) Inventors: Rifat Pamukcu, Spring House; Gary A. Piazza, Doylestown, both of PA (US)

(73) Assignee: Cell Pathways, Inc., Horsham, PA (US)

( * ) Notice: Subject to any disclaimer, the term of this patent is extended or adjusted under 35 U.S.C. 154(b) by 0 days.

(21) Appl. No.: 09/443,395

(22) Filed: Nov. 19, 1999

Related U.S. Application Data

(63) Continuation of application No. 09/200,139, filed on Nov. 25, 1998, now abandoned.

(51) Int. Cl.⁷ .............................................. A61K 31/404
(52) U.S. Cl. ...................... 514/414; 514/415; 514/418; 514/419
(58) Field of Search ................................ 514/414, 415, 514/418, 419

(56) References Cited

U.S. PATENT DOCUMENTS

| | | | |
|---|---|---|---|
| 4,950,680 A | 8/1990 | Taylor et al. | 514/356 |
| 5,206,377 A | * 4/1993 | McAfee | 548/253 |
| 5,696,159 A | 12/1997 | Gross et al. | 514/468 |
| 6,001,868 A | * 12/1999 | Firestone et al. | 514/415 |

FOREIGN PATENT DOCUMENTS

| | | |
|---|---|---|
| WO | WO 95/19978 | 7/1995 |
| WO | WO 00/15222 | 3/2000 |

OTHER PUBLICATIONS

Blaya, C. et al., Effect of the protein kinase inhibitors, 1–(5–isoquinolinylsulfonyl)–2–methylpiperazine H–7 and N–(2–[methylamino]ethyl)–5–isoquinoline–sulfonamide H–8 on Lewis lung carcinoma tumor progression, European Journal of Pharmacology, 354, pp. 99–104 (1998).

Chang, W. et al., Sulindac Sulfone Modulates the Expression and Cellular Localization of b–Catenin in Human Colon Carcinoma Cells, Digestive Disease Week, Apr. 1, 1999.

Earnest, D. et al., Piroxicam and Other Cyclooxygenase Inhibitors: Potential for Cancer Chemoprevention, Journal of Cellular Biochemistry, Supplement 161:156–166 (1992).

Easwaran, V. et al., The Ubiquitin–Proteasome Pathway and Serine Kinase Activity Modulate Adenomatous Polyposis Coli Protein–mediated Regulation of β–Catenin–Lymphocyte Enhancer–binding Factor Signaling, The Journal of Biological Chemistry, vol. 274, No. 23, pp. 16641–16645, Jun. 4, 1999.

Jiang, X. et al., Inhibition of calmodulin–dependent phosphodiesterase induces apoptosis in human leukemic cells, Proc. Natl. Acad. Sci. USA, vol. 83, pp. 11236–11241, Oct. 1996.

Korinek, V. et al., Constitutive Transcriptional Activation by a β–Catenin–Tcf Complex in $APC^{-/-}$ Colon Carcinoma, Science, vol. 275, pp. 1784–1786, Mar. 21, 1997.

Mahmoud, N. et al., Apc Gene Mutation is Associated with a Dominant–Negative Effect upon Intestinal Cell Migration, Cancer Research 57, pp. 5045–5050, Nov. 15, 1997.

Mahmoud, N. et al., Genotype–Phenotype Correlation in Murine Apc Mutation: Differences in Enterocyte Migration and Response to Sulindac, Cancer Research 59, pp. 353–359, Jan. 15, 1999.

Morin, P. et al., Activation of β–Catenin–Tcf Signaling in Colon Cancer by Mutations in β–Catenin or APC, Science, vol. 275, pp. 1787–1789, Mar. 21, 1997.

Peifer, M., β–Catenin as Oncogene: The Smoking Gun, Science, vol. 275, pp. 1752–1753, Mar. 21, 1997.

Rubinfeld, B. et al., Stabilization of β–Catenin by Genetic Defects in Melanoma Cell Lines, Science, vol. 275, pp. 1790–1792, Mar. 21, 1997.

\* cited by examiner

Primary Examiner—Fiona T. Powers
(74) Attorney, Agent, or Firm—Robert W. Stevenson

(57) ABSTRACT

A method for inhibiting neoplasia, particularly cancerous and precancerous lesions, by exposing the affected cells to indole derivatives.

14 Claims, No Drawings

METHOD OF INHIBITING NEOPLASTIC CELLS WITH INDOLE DERIVATIVES

This is a continuation of application Ser. No. 09/200,139 filed Nov. 25, 1998 now abandoned.

TECHNICAL FIELD

This invention relates to a method for the selective inhibition of neoplastic cells, for example, for the treatment or prevention of precancerous lesions or other neoplasias in mammals.

BACKGROUND OF THE INVENTION

Each year in the United States alone, untold numbers of people develop precancerous lesions, which is a form of neoplasia, as discussed below. Such lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds that prevent or induce the remission of existing precancerous or cancerous lesions or carcinomas would greatly reduce illness and death from cancer.

For example, approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and clonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

In the breast, breast cancer is often treated surgically, often by radical mastectomy with its painful aftermath. Such surgery is costly, too.

As indicated above, each lesion carries with it a chance that it will develop into a cancer. The likelihood of cancer is diminished if a precancerous lesion is removed. However, many of these patients demonstrate a propensity for developing additional lesions in the future. They must, therefore, be monitored periodically for the rest of their lives for reoccurrence.

In most cases (i.e. the cases of sporadic lesion formation, e.g. so-called common sporadic polyps), lesion removal will be effective to reduce the risk of cancer. In a small percentage of cases (i.e. cases where numerous lesions form, e.g. the so-called polyposis syndromes), removal of all or part of the effected area (e.g. the colon) is indicated. For example, the difference between common sporadic polyps and polyposis syndromes is dramatic. Common sporadic polyp cases are characterized by relatively few polyps which can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each lesion carries with it a palpable risk of cancerous development, patients who form many lesions (e.g. polyposis syndrome patients) invariably develop cancer if left untreated. Surgical removal of the colon is the conventional treatment in polyposis patients. Many polyposis patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because chemotherapy for cancer itself is often not effective and has severe side effects. Cancer chemoprevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those patients with high-risk genetic factors, such as the potential for polyposis syndrome, who would greatly benefit from chemopreventative drugs. Therefore, finding such anti-cancer drugs that can be used for prolonged preventive use is of vital interest.

Known chemopreventative and chemotherapeutic drugs are believed to kill cancer cells by inducing apoptosis, sometimes referred to as "programmed cell death." Apoptosis naturally occurs in virtually all tissues of the body, and especially in self-renewing tissues such as bone marrow, immune cells, gut, liver and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis play a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long-term use, or use in otherwise healthy individuals with precancerous lesions. These side effects, which are a result of the high levels of cytotoxicity of the drugs, include hair loss, weight loss, vomiting, immune suppression and other toxicities. Therefore, there is a need to identify new drug candidates for therapy that do not have such serious side effects in humans.

In recent years, several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the prophylactic use of currently available NSAIDs, even in polyposis syndrome patients, is marked by severe side reactions that include gastrointestinal irritations, perforations, ulcerations and kidney toxicity. Once NSAID treatment is terminated due to such complications, the polyps return, particularly in polyposis syndrome patients.

Sulindac has been particularly well received among the NSAIDs for polyp treatment. Sulindac is a sulfoxide compound that itself is believed to be inactive as an anti-arthritic agent. The sulfoxide is reportedly converted by liver enzymes to the corresponding sulfide, which is acknowledged to be the active moiety as a prostaglandin synthesis inhibitor. The sulfide, however, is associated with the side effects of conventional NSAIDs. The sulfoxide is also known to be metabolized to a sulfone compound that has been found to be inactive as an inhibitor of prostaglandin synthesis but active as an inhibitor of precancerous lesions.

SUMMARY OF THE INVENTION

This invention includes a method of inhibiting neoplastic cells by exposing those cells to a pharmacologically effective amount of those compounds described below. Such compounds are effective in modulating apoptosis and eliminating and inhibiting the growth of neoplasias such as precancerous lesions, but are not characterized by the severe side reactions of conventional NSAIDs or other chemotherapeutics.

The compounds of that are useful in the methods of this invention include those of Formula I:

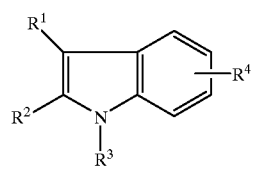

(I)

wherein $R^1$ is selected from the group consisting of hydrogen, halogen, nitro, carboxy, protected carboxy, acyl, cyano, hydroxyimino(lower)alkyl, lower alkenyl optionally substituted with oxo, or lower alkyl optionally substituted with protected carboxy, carboxy or hydroxy;

$R^2$ is selected from the group consisting of hydrogen, halogen, lower alkenyl, acyl, or lower alkyl optionally substituted with protected carboxy, carboxy, lower alkoxy, or hydroxy, or $R^1$ and $R^2$, together with the carbon atoms to which they are attached form a 4- to 7-membered carbocyclic ring optionally substituted with Oxo;

$R^3$ is selected from the group consisting of lower alkenyl or lower alkyl, both of which are optionally substituted with one or more substituent(s) selected from the group consisting of (1) oxo, (2)aryl optionally substituted with one or more substituents selected from the group consisting of halogen, aryl, lower alkoxy, lower aklylenedioxy, cyano, nitro, carboxy, protected carboxy, acyl, and amino optionally substituted with acyl or protected carboxy, and (3) a heterocyclic group optionally substituted with halogen; and $R^4$ is selected from the group consisting of carboxy, protected carboxy, acyl, cyano, halogen, a heterocyclic group, amino optionally substituted with acyl or protected carboxy, or lower alkyl optionally substituted with protected carboxy, carboxy, or acyl;

or its pharmaceutically acceptable salts

DETAILED DESCRIPTION OF THE PREFERRED EMBODIMENTS

As indicated above, this invention relates to a method for inhibiting neoplasia, particularly cancerous and precancerous lesions by exposing the affected cells to a compound of Formula I above.

Preferably, such compounds are administered without therapeutic amounts of an NSAID.

The present invention is also a method of treating mammals with precancerous lesions by administering a pharmacologically effective amount of an enterically coated pharmaceutical composition that includes compounds of this invention.

Also, the present invention is a method of inhibiting the growth of neoplastic cells by exposing the cells to an effective amount of compounds of Formula I, wherein $R_1$ through $R_3$ are defined as above.

In still another form, the invention is a method of inducing apoptosis in human cells by exposing those cells to an effective amount of compounds of Formula I to those cells sensitive to such a compound.

As used herein, the term "precancerous lesion" includes syndromes represented by abnormal neoplastic, including dysplastic, changes of tissue.

Examples include adenomatous growths in colonic, breast or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), prostatic dysplasia, bronchial dysplasia, breast, bladder and/or skin and related conditions (e.g., actinic keratosis), whether the lesions are clinically identifiable or not.

As used herein, the term "carcinomas" refers to lesions that are cancerous. Examples include malignant melanomas, breast cancer, and colon cancer.

As used herein, the term "neoplasm" refers to both precancerous and cancerous lesions.

It will also be appreciated that a compound of Formula I or a physiologically acceptable salt or solvate thereof can be administered as the raw compound, or as a pharmaceutical composition containing either entity.

Compounds useful in the methods of this invention are preferably formulated into compositions together with pharmaceutically acceptable carriers for oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories that may contain, in addition to the compounds of Formula I, excipients such as cocoa butter or a suppository wax.

The pharmaceutically acceptable carrier and compounds of this invention are formulated into unit dosage forms for administration to a patient. The dosage levels of active ingredient (i.e. compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g. a box or bottle, or both) with suitable printed material (e.g. a package insert) containing indications, directions for use, etc.

For administration to humans in the curative or prophylactic treatment of the disorders identified above, oral dosages of a compound of Formula I will generally be in the range of from 0.01–1000 mg daily for an average adult patient, preferably from 0.1–500 mg of active compound more preferably, in a suitable pharmaceutically acceptable vehicle or carrier, for administration in single or multiple doses, once or several times per day. In practice, the physician will determine the actual dosing regimen that will be most suitable for an individual patient and it will vary with the age, weight and response of the particular patient. The above dosages are believed to be exemplary of the average case, but there may be individual instances in which higher or lower dosage ranges may be merited, and such are within the scope of this invention.

A preferred group of compounds useful in the practice of this invention are those of formula I wherein $R^1$ is selected from the group consisting of cyano, acyl, or lower alkyl optionally substituted with hydroxy; $R^2$ is selected from the group consisting of hydrogen, acyl, lower alkenyl, or lower alkyl optionally substituted with lower alkoxy or hydroxy; $R^3$ is methyl substituted with aryl or a heterocyclic group, wherein aryl is optionally substituted with one or more substituent selected from the group consisting of halogen, lower alkylenedioxy, protected carboxy and carboxy; or $R^1$ and $R^2$ together with the carbon atoms to which they are attached represent a 4- to 7-membered carbocyclic ring optionally substituted with oxo; and $R^4$ is selected from the group consisting of acyl, cyano, or a heterocyclic group.

A more preferred group of compounds useful in the practice of this invention are those of formula I wherein $R^1$ is selected from the group consisting of lower alkyl, or lower alkanoyl optionally substituted with hydroxy, lower alkoxy, or aryl; $R^2$ is selected from the group consisting of hydrogen, lower alkenyl, or lower alkyl optionally substituted with lower alkoxy; and $R^3$ is benzyl optionally substituted with one or more substituent(s) selected from the group consisting of halogen and lower alkylenedioxy.

A particularly preferred group of compounds useful in the practice of this invention are those of formula I wherein $R^4$ is —C(O)NR$^5$R$^6$ wherein $R^5$ is selected from the group consisting of hydrogen or lower alkyl, and $R^6$ is selected from the group consisting of hydrogen, hydroxy, lower alkoxy, arylsulfonyl, a heterocyclic group, or lower alkyl optionally substituted with lower cycloalkyl or a heterocyclic group; or $R^5$ and $R^6$, together with the nitrogen atom to which they are attached, may represent a heterocyclic group.

An especially preferred group of compounds useful in the practice of this invention are those of formula I wherein $R^1$ is selected from the group consisting of lower alkanoyl optionally substituted with alkoxy; $R^2$ is lower alkyl; and $R^4$ is carbamoyl.

Compounds of formula (I) may contain one of more asymmetric centers and thus can exist as enantiomers or diastereoisomers. Furthermore, certain compounds of formula (I) that contain alkenyl groups may exist as cis- or trans-isomers. In each instance, the methods of this invention can be practices with mixtures or separate individual isomers.

Compounds of formula (I) may also exist in tautomeric forms and the methods of this invention can be practiced with mixtures and separate individual tautomers. Solvates of compounds of formula (I) can also be used in the methods of this invention.

Compounds of Formula I may be prepared by any suitable method known in the art or by the following processes disclosed in WO96/32379, which is incorporated herein by reference.

Process 1

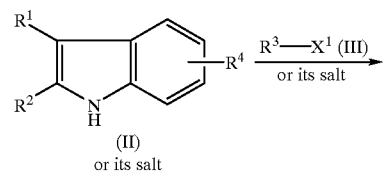

Process 2

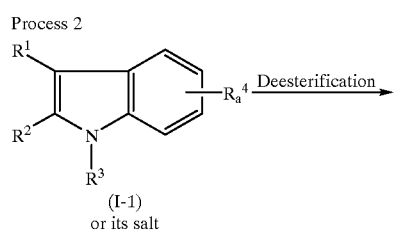
(I-1) or its salt

Deesterification →

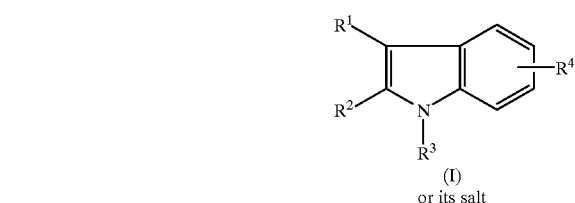
(I-2) or its salt

Process 3

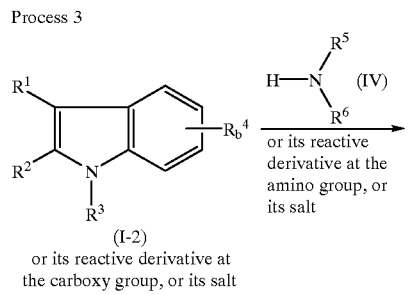
(I-2) or its reactive derivative at the carboxy group, or its salt $H-N\begin{smallmatrix}R^5\\R^6\end{smallmatrix}$ (IV)

or its reactive derivative at the amino group, or its salt

→

(I-3) or its salt

Process 4

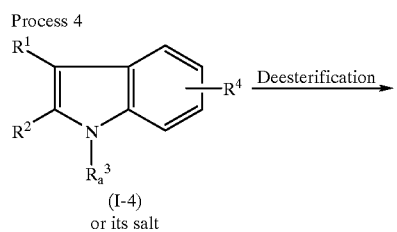
(I-4) or its salt

Deesterification →

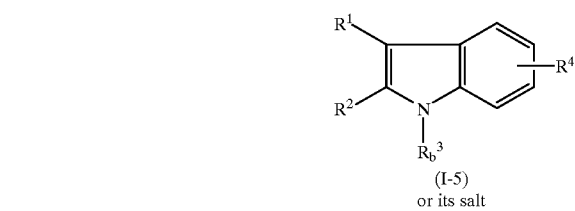
(I-5) or its salt

Process 5

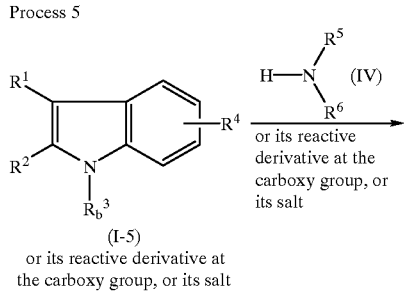
(I-5) or its reactive derivative at the carboxy group, or its salt $H-N\begin{smallmatrix}R^5\\R^6\end{smallmatrix}$ (IV)

or its reactive derivative at the carboxy group, or its salt

→

(I-6) or its salt

Process 6

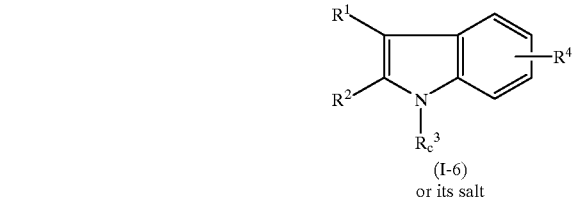
(I-7) or its salt

Reduction →

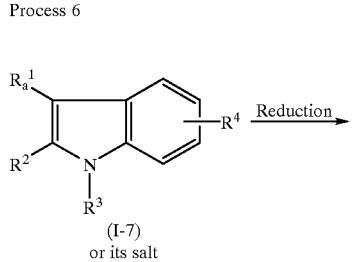
(I-8) or its salt

Process 7

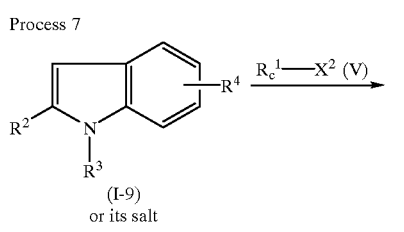
(I-9) or its salt $R_c^1\!-\!X^2$ (V) →

(I-10) or its salt

Process 8

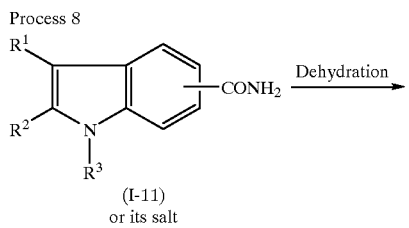
(I-11) or its salt

Dehydration →

-continued
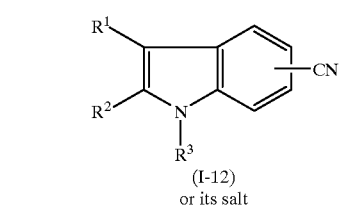
(I-12)
or its salt
Process 9
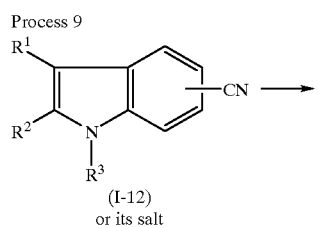
(I-12)
or its salt
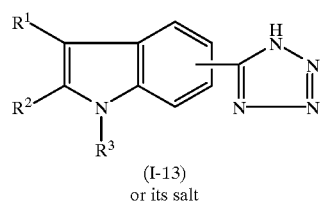
(I-13)
or its salt
Process 10
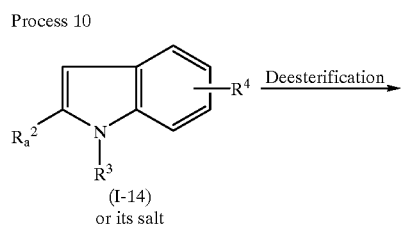
(I-14)
or its salt
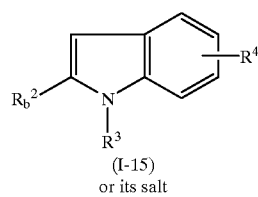
(I-15)
or its salt
Process 11
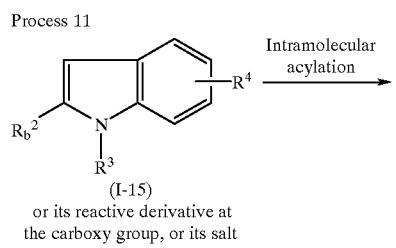
(I-15)
or its reactive derivative at
the carboxy group, or its salt
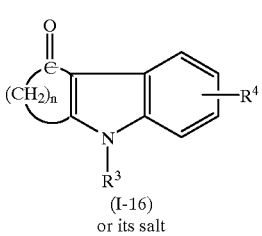
(I-16)
or its salt
Process 12
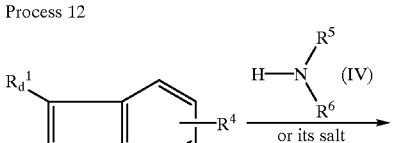
(I-17)
or its salt
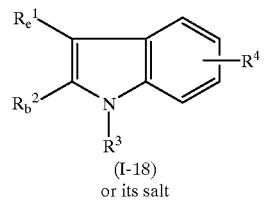
(I-18)
or its salt
Process 13
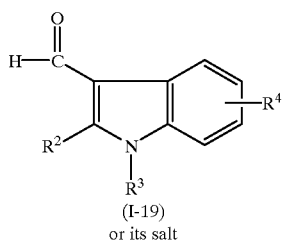
(I-9)
or its salt
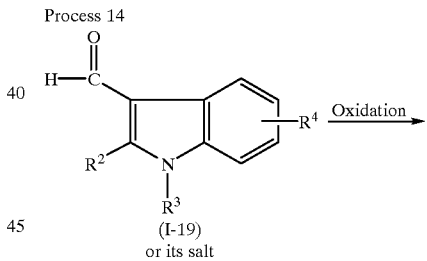
(I-19)
or its salt
Process 14
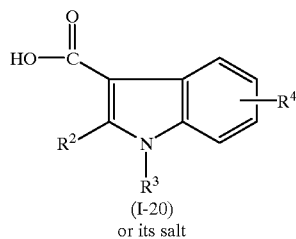
(I-19)
or its salt
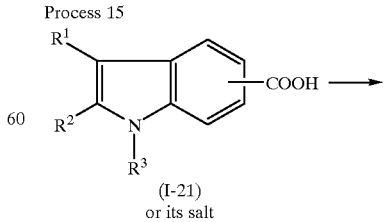
(I-20)
or its salt
Process 15
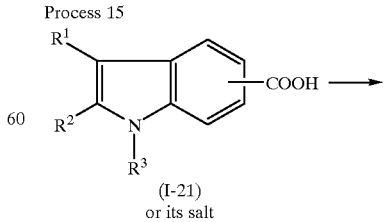
(I-21)
or its salt -continued Process 16

$R^1$, $R^2$, $R^3$ indole with $NH_2$ group (I-23) or its reactive derivative at the amino group, or its salt $R^8$—$X^3$ (VI) or its salt, or $R^9$—$N=C=O$ (VII) or its salt $R^1$, $R^2$, $R^3$ indole with $NHR^7$ (I-22) or its salt $R^1$, $R^2$, $R^3$ indole with $NHR^8$ (I-24) or its salt Process 17

$R^1$, $R^2$, $R_d^3$ indole with $R^4$ (I-25) or its salt

Reduction →

$R^1$, $R^2$, $R_e^3$ indole with $R^4$ (I-26) or its salt

Process 18

$R_f^1$, $R^2$, $R^3$ indole with $R^4$ (I-27) or its salt

Dealkylation →

$R_g^1$, $R^2$, $R^3$ indole with $R^4$ (I-28) or its salt

Process 19

$R^1$, $R_c^2$, $R^3$ indole with $R^4$ (I-29) or its salt

Oxidation →

$R^1$, $R_d^2$, $R^3$ indole with $R^4$ (I-30) or its salt

Process 20

$R^2$, $R^3$ indole with $R^4$ (I-9) or its salt

Halogenation →

$R_h^1$, $R^2$, $R^3$ indole with $R^4$ (I-31) or its salt

Process 21

$R^2$, $R^3$ indole with $R^4$ (I-9) or its salt

Nitration →

$O_2N$, $R^2$, $R^3$ indole with $R^4$ (I-32) or its salt

Process 22

$R_a^1$, $R^2$, $R^3$ indole with $R^4$ (I-7) or its salt

Reduction →

$R_i^1$, $R^2$, $R^3$ indole with $R^4$ (I-33) or its salt

-continued

Process 23

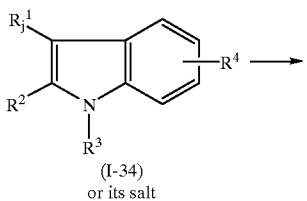
(I-34)
or its salt

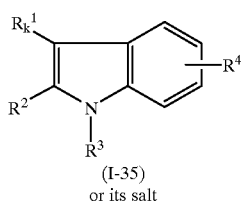
(I-35)
or its salt

Process 24

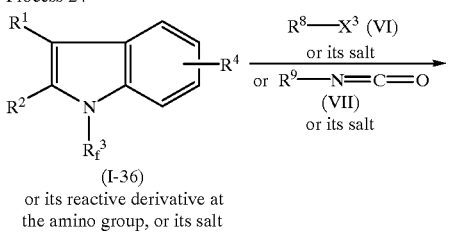
(I-36)
or its reactive derivative at
the amino group, or its salt

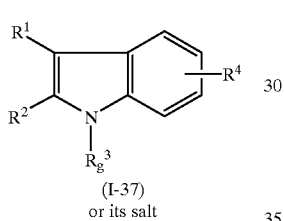
(I-37)
or its salt wherein $R^1$ to $R^6$ are each as defined above, $R_a^1$ is lower alkanoyl optionally substituted with protected carboxy or carboxy, $R_b^1$ is lower alkyl optionally substituted with protected carboxy or carboxy, $R_c^1$ is lower alkenoyl, aroyl, or lower alkanoyl optionally substituted with protected carboxy, carboxy or aryl, $R_d^1$ is chloroacetyl, $R_e^1$ is

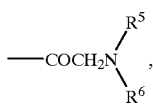

$R_f^1$ is lower alkanoyl substituted with lower alkoxy, $R_g^1$ is lower alkanoyl substituted with hydroxy, $R_h^1$ is halogen, $R_i^1$ is lower alkyl optionally substituted with protected carboxy or carboxy, $R_j^1$ is lower alkanoyl, $R_k^1$ is hydroxyimino(lower)alkyl, $R_a^2$ is lower alkyl substituted with protected carboxy, $R_b^2$ is lower alkyl substituted with carboxy, $R_c^2$ is 1-hydroxy(lower)alkyl, $R_d^2$ is lower alkanoyl, $R_a^3$ is lower alkenyl or lower alkyl, both of which are optionally substituted with oxo and both of which are substituted with aryl which is substituted with protected carboxy, $R_b^3$ is lower alkenyl or lower alkyl, both of which are optionally substituted with oxo and both of which are substituted with aryl which is substituted with carboxy, $R_c^3$ is lower alkenyl or lower alkyl, both of which are optionally substituted with oxo and both of which are substituted with aryl which is substituted with

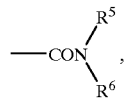

$R_d^3$ is lower alkenyl or lower alkyl, both of which are optionally substituted with oxo and both of which are substituted with aryl which is substituted with nitro, $R_e^3$ is lower alkenyl or lower alkyl, both of which are optionally substituted with oxo and both of which are substituted with aryl which is substituted with amino, $R_f^3$ is lower alkenyl or lower alkyl, both of which are optionally substituted with oxo and both of which are substituted with aryl which is substituted with amino, $R_g^3$ is lower alkenyl or lower alkyl, both of which are optionally substituted with oxo and both of which are substituted with aryl which is substituted with amino substituted with acyl, $R_a^4$ is protected carboxy or lower alkyl substituted with protected carboxy, $R_b^4$ is carboxy or lower alkyl substituted with carboxy, $R_c^4$ is

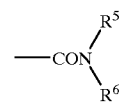

or lower alkyl substituted with

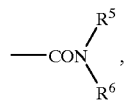

$R^7$ is hydrogen, protected carboxy, or

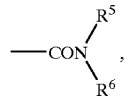

$R^8$ is acyl, $R^9$ is lower alkyl, $X^1$ is leaving group, $X^2$ and $X^3$ are each as the same as $X^1$, and n is 1, 2, 3 or 4.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

Suitable "lower alkyl" and lower alkyl moiety in the terms "lower alkoxy" and "hydroxyimino(lower)alkyl", may be a straight or branched $C_1$–$C_6$ alkyl such as methyl, ethyl, propyl, isopropyl, butyl, isobutyl, tert-butyl, pentyl, hexyl or the like, in which preferable one is $C_1$–$C_4$ lower alkyl such as methyl, ethyl, propyl, butyl, isobutyl or tert-butyl.

Suitable "lower alkenyl" may be a straight or branched $C_2$–$C_6$ alkenyl such as ethenyl, propenyl (i.e. allyl or 1-propenyl), butenyl, isobutenyl, or the like.

Suitable "lower cycloalkyl" may include one having 3 to 6 carbon atoms, for example, cyclopropyl, cyclobutyl, cyclopentyl, or the like.

Suitable "aryl" and aryl moiety in the term of "arylsulfonyl", "aroyl" and "ar(lower)alkanoyl" may include phenyl, naphthyl, tolyl, mesityl, xylyl, or the like.

Suitable "halogen" may be fluoro, chloro, bromo or iodo.

Suitable "lower alkylenedioxy" may include methylenedioxy, ethylenedioxy, or the like.

Suitable "protected carboxy" may be a pharmaceutically acceptable and a common protected carboxy, such as an esterified carboxy, or the like, and concrete examples of the ester moiety in said esterified carboxy may be lower alkyl optionally substituted with aryl (e.g. methyl, ethyl, propyl, tert-butyl, benzyl, and so on).

Suitable "heterocyclic group" may be one containing at least one hetero atom selected from nitrogen, sulfur and oxygen atom, and may include saturated or unsaturated, monocyclic or polycyclic heterocyclic group such as
(1) unsaturated 3 to 7-membered, preferably 5 or 6-membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g. 4H-1,2,4-triazolyl, 1H-1,2,3-triazolyl, 2H-1,2,3-triazolyl, etc.], tetrazolyl [e.g. 1H-tetrazolyl, 2H-tetrazolyl, etc.], etc.;
(2) saturated 3 to 7-membered, preferably 5 or 6-membered heteromonocyclic group containing 1 to 4 nitrogen atoms [e.g. pyrrolidinyl, imidazolidinyl, piperidino, piperazinyl, etc.];
(3) unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g. tetrazolo[1,5-b]pyridazinyl, etc.], etc.;
(4) unsaturated 3 to 7-membered, preferably 5 or 6-membered heteromonocyclic group containing an oxygen atom, for example, pyranyl, furyl, etc.;
(5) unsaturated, 3 to 7-membered, preferably 5 or 6-membered heteromonocyclic group containing 1 to 2 sulfur atoms, for example, thienyl, etc.;
(6) unsaturated 3 to 7-membered, preferably 5 or 6-membered heteromonocyclic group containing 1 to 2 oxygen atoms and 1 to 3 nitrogen atoms, for example, oxazolyl, isoxazolyl, oxadiazolyl [e.g. 1,2,4-oxadiazolyl, 1,3,4-oxadiazolyl, 1,2,5-oxadiazolyl, etc.], etc.;
(7) saturated 3 to 7-membered, preferably 5 or 6-membered heteromonocyclic group containing 1 to 2 oxygen atoms and 1 to 3 nitrogen atoms [e.g. morpholinyl, etc.];
(8) unsaturated condensed heterocyclic group containing 1 to 2 oxygen atoms and 1 to 3 nitrogen atoms [e.g. benzoxazolyl, benzoxadiazolyl, etc.];
(9) unsaturated 3 to 7-membered, preferably 5 or 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.], etc.
(10) saturated 3 to 7-membered, preferably 5 or 6-membered heteromonocyclic group containing 1 to 2 sulfur atoms and 1 to 3 nitrogen atoms [e.g., thiazolidinyl, etc.];
(11) unsaturated condensed heterocyclic group containing 1 to 2 sulfur atoms and 1 to 3 nitrogen atoms [e.g., benzothiazolyl, benzothiadiazolyl, etc.];
(12) unsaturated condensed heterocyclic group containing 1 to 2 sulfur atoms or 1 to 2 oxygen atoms [e.g., benzothiophen, benzofuran, etc.]; or the like.

"Heterocyclic group" defined above may be substituted with suitable substituent(s) such as lower alkyl, hydroxy, halogen, a heterocyclic group, or the like (e.g., 3-hydroxypyrrolidine, 4-methylpiperadine, 4-hydroxypiperidine, 1-methylimidazole, 4-(pyrimidin-2-yl)piperazin, and so on).

Suitable "acyl" may be aliphatic acyl, aromatic acyl or aliphatic acyl optionally substituted aryl, which are derived from carboxylic acid or carbamic acid.

The aliphatic acyl may include
(1) lower alkanoyl optionally substituted with one or more suitable substituent(s) such as hydroxy, lower alkoxy, carboxy, protected carboxy, halogen, lower alkylthio, heterocyclicthio, oxo, cyclo(lower)alkyl or a heterocyclic group (e.g. formyl, acetyl, propionyl, butyryl, isobutyryl, pentanoyl, hexanoyl, 3,3-dimethylbutanoyl, 3-hydroxy-3-methylbutanoyl, 3-oxo-butanoyl, 3-methoxycarbonylpropanoyl, 3-carboxypropanoyl, 4-methoxycarbonylbutanoyl, 4-carboxybutanoyl, methylthioacetyl, (1-methylimidazol-2-yl)thioacetyl, hydroxyacetyl, methoxyacetyl, ethoxyacetyl, 3-methoxybutanoyl, chloroacetyl, morpholinoacetyl, piperidinylacetyl, 4-methylpiperidin-1-ylacetyl, 4-hydroxypiperidinyl, pyrolidinylacetyl, 4-(pyrimidin-2-yl)piperidinylacetyl, 3-hydroxypyrrolidinylacetyl, oxolan-4-ylacetyl, and so on);
(2) cyclo(lower)alkanecarbonyl (e.g. cyclopropylcarbonyl, cyclobutylcarbonyl, cyclopentylcarbonyl, cyclohexylcarbonyl, and so on);
(3) lower alkenoyl (e.g. acryloyl, methacryloyl, crotonoyl, 3-methylbutanoyl, and so on);
(4)

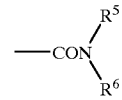

(wherein $R^5$ is hydrogen or lower alkyl, and $R^6$ is hydrogen, hydroxy, lower alkoxy, arylsulfonyl, a heterocyclic group, lower alkyl optionally substituted with lower cycloalkyl or a heterocyclic group, or the like, in addition to their significances above, $R^5$ and $R^6$, together with the nitrogen atom to which they are attached, may represent a heterocyclic group), such as carbamoyl, N-methylcarbamoyl, N,N-dimethylcarbamoyl, N-ethylcarbamoyl, N,N-diethylcarbamoyl, N-propylcarbamoyl, N-phenylsulfonylcarbamoyl, N-methoxycarbamoyl, N-(tetrazol-5-yl)carbamoyl, 1-pyrolidinylcarbonyl, piperidinocarbonyl, 4-methyl-1-piperazinylcarbonyl, 4-cyclohexyl-1-piperazinylcarbonyl, morpholinocarbonyl, 4-thiomorpholinylcarbonyl, or the like.

The aromatic acyl may include aroyl optionally substituted with one or more suitable substituent(s) such as nitro (e.g. benzoyl, naphthoyl, nitrobenzoyl, and so on), or the like.

The aliphatic acyl substituted with aryl may include ar(lower)alkanoyl which may have one or more suitable substituent(s) such as lower alkoxy (e.g. phenylacetyl, 4-methoxyphenylacetyl, and so on) or the like.

Suitable "arylsulfonyl" may include phenylsulfonyl, tosyl, methoxyphenylsulfonyl, or the like.

Suitable "leaving group" may include hydroxy, halogen, acyloxy, in which the halogen and the acyl moiety may be those as exemplified above, or the like.

The starting compound (II) is prepared in similar manners to those of the below-mentioned Preparations.

Suitable salts of the compounds (I), (I-1) to (I-36) and (II) to (VII) may include pharmaceutically acceptable salts such as basic salts, for example, alkali metal salt (e.g. sodium salt, potassium salt, etc.), alkaline earth metal salt (e.g. calcium salt, magnesium salt, etc.), ammonium salt, amine salt (e.g. triethylamine salt, N-benzyl-N-methylamine salt, etc.) and other conventional organic salts, or acid addition salts, for example, hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, p-toluenesulfonate, or the like.

The processes for preparing the object compound (I) are explained in detail in the following.

PROCESS 1

The compound (I) or its salt can be prepared by reacting the compound (II) or its salt with the compound (III) or its salt.

This reaction is usually carried out in the presence of an inorganic or an organic base.

Suitable inorganic base may include an alkali metal [e.g., sodium, potassium, etc.], an alkali metal hydroxide [e.g., sodium hydroxide, potassium hydroxide, etc.], alkali metal hydrogen carbonate [e.g., sodium hydrogen carbonate, potassium hydrogen carbonate, etc.], alkali metal carbonate [e.g., sodium carbonate, etc.], alkali earth metal carbonate [calcium carbonate, etc.], or the like.

Suitable organic base may include tri(lower)alkylamine [e.g. triethylamine, N,N-diisopropylethylamine, etc.], alkyl lithium [e.g. methyl lithium, butyl lithium, etc.], lithium diisopropylamide, lithium hexamethyldisirazido, alkali metal hydride [e.g., sodium hydride, potassium hydride, etc.] or the like.

The reaction is usually carried out in a conventional solvent such as water, alcohol [e.g., methanol, ethanol, isopropyl alcohol, etc.], tetrahydrofuran, dioxane, toluene, methylene chloride, chloroform, N,N-dimethylformamide or any other organic solvents which do not adversely affect the reaction, or the mixture thereof.

The reaction temperature is not critical and the reaction is usually carried out under cooling to warming.

PROCESS 2

The object compound (I-2) or its salt can be prepared by subjecting a compound (I-1) to deesterification.

The reaction is carried out in accordance with a conventional method such as hydrolysis, reduction or the like.

The hydrolysis is preferably carried out in the presence of a base, an acid, or the combination of Lewis acids and Lewis bases.

Suitable base may include an inorganic base and an organic base.

Suitable inorganic base may be the same as those exemplified in Process 1.

Suitable organic base may include tri(lower)alkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, hydroiodic acid, sulfuric acid, etc.].

The hydrolysis is also carried out in the presence of the combination of Lewis acids and Lewis bases.

Suitable Lewis acid may include metal halide [e.g., aluminum chloride, aluminum bromide, titanium(IV) chloride, tin(IV) chloride, etc.], metal alkoxide [e.g., titanium(IV) isopropoxide, etc.] or the like.

Suitable Lewis base may include lower alkyl thiol [e.g., ethanethiol, ethanedithiol, etc.], di(lower)alkyl sulfide [dimethylsulfide, etc.], or the like.

The reaction is usually carried out in a solvent such as water, an alcohol [e.g. methanol, ethanol, etc.], xylene, diethylene glycol monomethyl ether, methylene chloride, tetrahydrofuran, a mixture thereof or any other solvent which does not adversely influence the reaction. A liquid base or acid can be also used as the solvent.

The reaction temperature is not critical and the reaction is usually carried out under cooling to warming.

The reduction can be applied preferably for elimination of the ester moiety such as 4-nitrobenzyl, 2-iodoethyl, 2,2,2-trichloroethyl, or the like. The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid exemplified above.

Suitable catalysts to be used in catalytic reduction are conventional ones such as platinum catalyst [e.g. platinum on carbon, platinum oxide, etc.], palladium catalyst [e.g. palladium black, palladium oxide, palladium on carbon, etc.] or any other catalyst ordinary employed in the field of organic synthetic chemistry. The catalytic reduction may be carried out in the presence of hydrogen or hydrogen doner such as formic acid, ammonium formate, cyclohexene, or the like.

The reduction is usually carried out in a conventional solvent which does not adversely influence the reaction such as water, an alcohol [e.g. methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

PROCESS 3

The compound (I-3) or its salt can be prepared by reacting the compound (I-2) or its reactive derivative at the carboxy group,.or its salt, with the compound (IV) or its reactive derivative at the amino group, or its salt, according to any well known procedure.

Suitable reactive derivative at the amino group of the compound (IV) may include Schiff's base type imino or its tautomeric enamine type isomer formed by the reaction of the compound (IV) with a carbonyl compound such as aldehyde, ketone or the like; a silyl derivative formed by the reaction of the compound (IV) with a silylating reagent such as trimethylsilyl chloride, N,O-bis(trimethylsilyl)acetamide, N-trimethylsilylacetamide, or the like.

Suitable reactive derivative of the compound (I-2) may include an acid chloride, acid azide, an acid anhydride, an activated amide, an activated ester, or the like.

The suitable acid anhydride may include a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfuric acid, thiosulfuric acid, alkanesulfonic acid (e.g., methanesulfonic acid, ethanesulfonic acid, etc.), sulfuric acid, alkanoic acid (e.g., pivalic acid, pentanoic acid, isopentanoic acid, etc.), aromatic carboxylic acid (e.g., benzoic acid, chlorobenzoic acid, fluorobenzoic acid, nitrobenzoic acid, etc.),or the like.

Suitable activated amide may be imidazoylamide, 4-substituted imidazoylamide, dimethylpyrazolylamide, triazolylamide tetrazolylamide, or the like.

Suitable activated ester may be dimethyliminomethyl [$(CH_3)_2N=CH—$] ester, vinyl ester, propargyl ester, 4-nitrophenyl ester, 2,4-dinitrophenyl ester, trichlorophenyl ester, pentachlorophenol ester, pentafluorophenyl ester, methanesulfonylphenyl ester, phenyl thioester, p-nitrophenyl thioester, carboxymethyl thioester, pyranyl ester, pyridyl ester, 8-quinolyl thioester, an ester with a N-hydroxy compound (e.g., N,N-dimethylhydroxylamine, 1-hydroxy-2H-pyridone, N-hydroxysuccinimido, N-hydroxybenzotriazole, N-hydroxyphthalimide, etc.), or the like.

These reactive derivatives can optionally be selected from them according to the kind of compound (I-2) to be used.

When the compound (I-2) is used in free acid form or its salt form in the reaction, the reaction is preferably carried out in the presence of condensing agent.

Suitable condensing agent may include a carbodiimide (e.g., N,N-dicyclohexylcarbodiimide, N-cyclohexyl-N'-(4-diethylaminocyclohexyl)carbodiimide, N-ethyl-N'-(3-dimethylaminopropyl)carbodiimide or its hydrochloride, etc.) diphenylphosphinic azido, diphenylphosphinic chloride, diethylphosphoryl cyanide., bis(2-oxo-3-oxazolidinyl)-phosphinic chloride, N,N'-carbonyldiimidazole, 2-ethoxy-1-ethoxycarbonyl-1,2-dihydroquinoline, cyanuric chloride, or the like.

The reaction may be also carried out in the presence of organic or inorganic base such as alkali metal carbonate, tri(lower)alkylamine, pyridine, N-(lower)alkylmorphorine, or the like.

The reaction is usually carried out in a conventional solvent such as water, acetone, alcohol [e.g., methanol, ethanol, isopropyl alcohol, etc.], tetrahydrofuran, dioxane, toluene, methylene chloride, chloroform, N,N-dimethylformamide or any other organic solvents which do not adversely affect the reaction, or the mixture thereof.

The reaction temperature is not critical and the reaction is usually carried out under cooling to warming.

PROCESS 4

The compound (I-5) or its salt can be prepared by subjecting the compound (I-4) or its salt to deesterification.

This deesterification can be carried out in a similar manner to that of the Process 2, and therefore the reagents to be used and the reaction conditions (e.g., solvent, reaction temperature, etc.) can be referred to those of the Process 2.

PROCESS 5

The compound (I-6) or its salt can be prepared by reacting the compound (I-5) or its reactive derivative at the carboxy group, or its salt, with the compound (IV) or its reactive derivative at the amino group, or its salt.

This reaction can be carried out in a similar manner to that of the Process 3, and therefore the reagents to be used and the reaction conditions (e.g., solvent, reaction temperature, etc.) can be referred to those of the Process 3.

PROCESS 6

The compound (I-8) or its salt can be prepared by reacting a compound (I-7) or its salt with a reducing agent.

Suitable reducing agent may be diborane, sodium borohydride, lithium aluminum hydride or the like.

The reaction is usually carried out in a conventional solvent such as diethyl ether, tetrahydrofuran or any other organic solvent which dose not adversely influence the reaction.

The reaction temperature is not critical, and the reaction can be carried out under cooling to heating.

PROCESS 7

The compound (I-10) or its salt can be prepared by reacting the compound (I-9) or its salt with an acylating agent (V).

Suitable acylating agent (V) may be a conventional one used in the Friedel-Crafts acylation reaction such as an acid halide [e.g. acid chloride, acid bromide, etc.], an acid anhydride or the like.

This reaction is preferably carried out in the presence of a Lewis acid such as aluminum halide [e.g. aluminum chloride, aluminum bromide, etc.], titanium halide [e.g. titanium tetrachloride, etc.], zinc halide (e.g. zinc chloride), boron trifluoride or the like.

The reaction is usually carried out in a conventional solvent such as carbon disulfide, dichloroethane, tetrachloromethane, benzene or any otherorganic solvent which does not adversely influence the reaction.

The reaction temperature is not critical, and the reaction is usually carried out under cooling to heating.

PROCESS 8

The compound (I-12) or its salt can be prepared by subjecting the compound (I-11) or its salt to dehydration at the carbamoyl group.

Dehydration is carried out in the conventional manner, which is capable dehydrating a carbamoyl group to cyano group, and suitable dehydrating agent may be phosphorus compound (e.g. phosphorous pentoxide, phosphorus pentachloride, phosphorous oxychloride, pyrocatechyl phosphorus trichloride, and so on); thionyl chloride; or a combination of triaryl phosphine (e.g. triphenyl phosphine, and so on) and chloroform or carbon tetrachloride.

The reaction is usually carried out in a conventional solvent such as water, alcohol [e.g., methanol, ethanol, isopropyl alcohol, etc.), tetrahydrofuran, dioxane, toluene, methylene chloride, chloroform, carbon tetrachloride, N,N-dimethylformamide or any other organic solvents which do not adversely affect the reaction, or the mixture thereof.

The reaction temperature is not critical and the reaction is usually carried out under cooling to warming.

PROCESS 9

The object compound (I-13) or its salt can be prepared by reacting a compound (I-12) or its salt with an azide compound.

Suitable azide compound may be alkali metal azide [e.g. sodium azide, potassium azide, etc.], alkaline earth metal azide [e.g. calcium azide, etc.], aluminum azide, hydrogen azide, trimethyltin azide, or the like.

The reaction is preferably carried out in the presence of ammonium halide [e.g. ammonium chloride, ammonium bromide, etc.], lower alkylammonium halide [e.g. trimethylammonium chloride, triethylammonium chloride, etc.] or the like.

The reaction is usually carried out in a conventional solvent such as tetrahydrofuran, dioxane, N,N-dimethylformamide or any other organic solvent which does not adversely influence the reaction.

The reaction temperature is not critical, and the reaction can be carried out under warming to heating.

PROCESS 10

The compound (I-15) or its salt can be prepared by subjecting the compound (I-14) or its salt to deesterification.

This deesterification can be carried out in a similar manner to that of the Process 2, and therefore the reagents to be used and the reaction conditions (e.g., solvent, reaction temperature, etc.) can be referred to those of the Process 2.

PROCESS 11

The compound (I-16) or its salt can be prepared by subjecting the acid chloride or acid anhydride derived from the compound (I-15) or its salt to intramolecular acylation reaction.

This intramolecular acylation reaction can be carried out in a similar manner to that of the Process 7, and therefore the reagents to be used and the reaction conditions (e.g., solvent, reaction temperature, etc.) can be referred to those of the Process 7.

PROCESS 12

The compound (I-18) or its salt can be prepared by reacting the compound (I-17) or its salt with compound (IV).

This reaction is preferably carried out in the presence of organic or inorganic base exemplified in Process 1, and/or alkali metal iodide (e.g. sodium iodide, potassium iodide, etc.).

The reaction is usually carried out in a solvent such as water, tetrahydrofuran, dioxane, N,N-dimethylformamide or any other solvent which does not adversely influence the reaction.

The reaction temperature is not critical, and the reaction is usually carried out at ambient temperature of under warming to heating.

PROCESS 13

The compound (I-19) or its salt can be prepared by reacting a compound (I-9) or its salt with a formylating agent.

Suitable formylating agent may be N,N-dimethylformamide; $(CH_3)_2N^+=CHCl.Cl_2PO_2^-$ (so-called Vilsmeier reagent prepared by the reaction of N,N-dimethylformamide with phosphorus oxychloride, phosgene, etc.); or the like.

When a formylating agent is N,N-dimethylformamide, the reaction is preferably carried out in the presence of a base such as lower alkyl alkali metal [e.g. n-butyl lithium, ethyl magnesium bromide, etc.], or the like.

The reaction is usually carried out in a solvent such as dioxane, tetrahydrofuran, N,N-dimethylformamide, methylene chloride, chloroform, or any other organic solvent which does not adversely influence the reaction.

The reaction temperature is not critical, and the reaction is usually carried out under cooling to heating.

PROCESS 14

The compound (I-20) or its salt can be prepared by subjecting the compound (I-19) or its salt to oxidation reaction.

Oxidation is carried out in a conventional manner, which is capable of oxidizing formyl group to carboxy group, and suitable oxidizing reagent may be oxygen acid such as periodate (e.g. sodium periodate, potassium periodate, etc.), peroxy acid such as peroxybenzoic acid (e.g., peroxybenzoic acid, m-chloroperoxybenzoic acid, etc.), potassium permanganate, cromic acid, sodium hypochlorite, or the like.

The reaction is usually carried out in a conventional solvent such as water, alcohol (e.g., methanol, ethanol, isopropyl alcohol, etc.), tetrahydrofuran, dioxane, dichloromethane, ethylene dichloride, chloroform, N,N-dimethylformamide, N,N-dimethylacetamide, or any other organic solvent which does not adversely affect the reaction.

Among these solvents, hydrophilic solvents may be used in a mixture with water.

The reaction temperature is not critical and the reaction is usually carried out under cooling to heating.

PROCESS 15

The compound (I-22) or its salt can be prepared by subjecting the compound (I-21) or its salt to a rearrangement reaction.

The rearrangement reaction, which is capable of converting the carboxy group into amino group optionally substituted with protected carboxy or acyl (e.g. Carbamoyl substituted with lower alkyl, etc.), may be the condition such as Curtius Rearrangement, Hoffmann reaction, Schmidt reaction, or the modification thereof.

For example, the Curtius rearrangement consists of the formation of acid azide, the decomposition of acid azide to isocyanate and nitrogen, and the reaction of isocyanate with water, alcohol or amine to afford amine, urethane or urea, respectively.

Acid azide can be prepared by treating corresponding acid hydrazide with nitrous acid, treating corresponding acid chloride with alkali metal azide, treating carboxylic acid with diphenylphosphoryl azide, or the like.

Acid azide can be rearranged in inert solvent (e.g., toluene, dichloromethane, etc.), from which the isocyanate can be isolated, or in the presence of reagents like alcohol or amine which will react with the intermediate isocyanate to form urethan or urea. Amine or its salt can be obtained by hydrolysis of isocyanate, urethan, or urea.

The reaction temperature is not critical and the reaction is usually carried out under cooling to warming.

PROCESS 16

The compound (I-24) or its salt can be prepared by reacting the compound (I-23) or its reactive derivative at the amino group, or its salt, with the compound (VI) or its salt, or the compound (VII) or its salt.

When free acid is used as the compound (VI), the reaction is preferably carried out in the presence of condensing agent exemplified in Process 3.

The reaction is usually carried out in a conventional solvent such as water, alcohol [e.g., methanol, ethanol, isopropyl alcohol, etc.], tetrahydrofuran, dioxane, toluene, methylene chloride, chloroform, N,N-dimethylformamide or any other organic solvents which do not adversely affect the reaction, or the mixture thereof.

The reaction temperature is not critical and the reaction is usually carried out under cooling to warming.

PROCESS 17

The compound (I-26) or its salt can be prepared by subjecting a compound (I-25) or its salt to reduction.

The present reduction is carried out by chemical reduction, catalytic reduction, or the like.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalyst [e.g. platinum, platinum black, platinum oxide, etc.], palladium catalyst [e.g. palladium black, palladium oxide, palladium on carbon, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reduction is usually carried out in a conventional solvent which does not adversely influence the reaction such as water, an alcohol [e.g. methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent and other conventional solvent such as diethyl ether, methylene chloride, dioxane, tetrahydrofuran, etc., or a mixture thereof.

The reaction temperature of this reduction is not critical and the reaction is usually carried out under cooling to warming.

PROCESS 18

The compound (I-28) or its salt can be prepared by subjecting a compound (I-27) or its salt to cleavage of ether bond.

The cleavage of ether bond is carried out in the presence of an acid including Lewis acid [e.g. hydrochloric acid, hydrobromic acid, hydroiodic acid, boron tribromide, boron trichloride, etc.], tri(lower)alkylsilyliodide [e.g. trimethylsilyliodide, etc.], or any other method ordinary employed in the field of organic synthesis.

The reaction is usually carried out in a solvent such as water, acetic acid, methylene chloride, tetrahydrofuran, a mixture thereof or any other solvent which does not adversely influence the reaction.

The reaction temperature is not critical and the reaction is usually carried out under cooling to heating.

PROCESS 19

The compound (I-30) or its salt can be prepared by subjecting the compound (I-29) or its salt to oxidation.

This oxidation can be performed according to the general procedures ordinarily employed in the field of organic chemistry, which is capable of oxidizing a secondary alcohol to ketone, and suitable oxidizing agent is, for example, derivatives of hexavalent chromium($Cr^{VI}$) (e.g. chromium trioxide, sodium dichromate, chromium trioxide-dipyridine complex, etc.) or heptavalent manganese($Mn^{VII}$) (e.g. potassium permanganate, manganese dioxide, etc.).

The reaction is usually carried out in a conventional solvent such as water, tetrahydrofuran, dioxane, toluene, methylene chloride, chloroform, N,N-dimethylformamide, acetone, or any other organic solvents which do not adversely affect the reaction, or the mixture thereof.

The reaction temperature is not critical and the reaction is usually carried out under cooling to warming.

PROCESS 20

The compound (I-31) or its salt can be prepared by subjecting the compound (I-9) or its salt to halogenation.

This halogenation is usually carried out by using a conventional halogenating agent such as halogen (e.g., chlorine, bromine, etc.), phosphorus trihalide (e.g., phosphorus tribromide, phosphorus ichloride, etc.), phosphorus pentahalide (e.g., phosphorous pentachloride, phosphorus pentabromide, etc.), phosphorus oxychloride (e.g., phosphoryl trichloride, phosphoryl monochloride, etc.), thionyl halide (e.g., thionyl chloride, thionyl bromide, etc.), oxalyl halide (e.g., oxalyl chloride, oxalyl bromide, etc.), sulfuryl halide (e.g. sulfuryl chloride, etc.), pyridinium hydrobromide perbromide, or the like.

This reaction is usually carried out in a solvent such as water, alcohol (e.g., methanol, ethanol, isopropyl alcohol, etc.), benzene, dioxane, N,N-dimethylformamide, tetrahydrofuran, methylene chloride, ethylene dichloride, chloroform, diethyl ether or any other solvent which dose not adversely affect the reaction.

The reaction temperature is not critical and the reaction is usually carried out under cooling to warming.

PROCESS 21

The compound (I-32) or its salt can be prepared by reacting a compound (I-9) or its salt with a nitrating agent.

Suitable nitrating agent may be nitric acid, fuming nitric acid, potassium nitrate, nitronium tetrafluoroborate or the like.

The reaction is usually carried out in an acid or an acid anhydride such as sulfuric acid, acetic acid, acetic anhydride or the like.

The reaction temperature is not critical, and the reaction is usually carried out under cooling to heating.

PROCESS 22

The compound (I-33) or its salt can be prepared by subjecting the compound (I-7) or its salt to reduction.

This reduction can be performed according to the general procedures ordinarily employed in the field of organic chemistry, which is capable of reducing a ketone to a secondary alcohol, and suitable reducing agent is, for example, metal hydride such as aluminum hydrides (e.g. lithium aluminum hydride, lithium di(lower)alkylaluminum hydride, Red-Al®, etc.), boron hydrides (e.g. sodium borohydride, sodium borocyanohydride, etc.), or the like.

The reaction is usually carried out in a conventional solvent such as water, tetrahydrofuran, dioxane, toluene, methylene chloride, chloroform, N,N-dimethylformamide, acetone, or any other organic solvents which do not adversely affect the reaction, or the mixture thereof.

The reaction temperature is not critical and the reaction is usually carried out under cooling to warming.

PROCESS 23

The compound (I-35) or its salt can be prepared by reacting a compound (I-34) or its salt with hydroxylamine or its salt.

The reaction is usually carried out in a conventional solvent such as water, an alcohol [e.g. methanol, ethanol, etc.], acetone, dioxane, acetonitrile, chloroform, methylene chloride, ethylene chloride, tetrahydrofuran, ethyl acetate, N,N-dimethylformamide, dioxane or any other organic solvent which does not adversely influence the reaction. These conventional solvents may also be used in a mixture with water.

The reaction is preferably carried out in the presence of an inorganic or organic base exemplified in Process 1.

The reaction temperature is not critical, and the reaction is usually carried out under cooling to heating.

PROCESS 24

The compound (I-37) or its salt can be prepared by reacting the compound (I-36) or its reactive derivative at the amino group, or its salt with the compound (VI) or compound (VII).

This reaction can be carried out in a similar manner to that of Process 16 and therefore the regents to be used and the reaction conditions (e.g. reaction temperature, etc.) can be referred to those of the Process 16.

The compounds (I) and pharmaceutically acceptable salts thereof of the present invention possess inhibitory activity of cGMP-PDE (especially PDE-V), relaxant activity of smooth muscle, bronchodilator activity, vasodilative activity, inhibitory activity of smooth muscle cells proliferation, inhibitory activity of allergy, and so on.

The compounds (I) and pharmaceutically acceptable salts thereof, therefore, have utility in the treatment and intramuscular, or parenteral applications. The active ingredient may be compounded, for example, with the usual non-toxic, pharmaceutically acceptable, carriers for ointment, cream, plaster, tablets, pellets, capsules, suppositories, solutions (saline, for example), emulsion, suspensions (olive oil, for example), and any other form suitable for use. The carriers which can be used are water, wax, glucose, lactose, gum acacia, gelatin, mannitol, starch paste, magnesium trisilicate, talc, corn starch, keratin, paraffin, colloidal silica, potato starch, urea and other carriers suitable for use in manufacturing preparations, in solid, semisolid, or liquid form, and in addition auxiliary, stabilizing, thickening and coloring agents and perfumes may be used. The active compound is included in the pharmaceutical composition in an effective amount sufficient to produce the desired effect upon the process or condition of the diseases.

Mammals which may be treated by the present invention include livestock mammals such as cows, horses, etc., domestic animals such as dogs, cats, rats, etc. and humans, preferably humans.

For applying this composition to a human, it is preferable to apply it by external (topical), oral, parenteral, enteral, intravenous, or intramuscular administration.

While the dosage of therapeutically effective amount of the macrolide compounds varies from and also depends upon the age and condition of each individual patient to be treated, in case of the systemic administration; a daily dose of about 0.01–1000 mg, preferably 0.1–500 mg and more preferably 0.5–100 mg of the active ingredient is generally given for treating the diseases, and an average single dose of about 0.2–0.5 mg, 1 mg, 5 mg, 10 mg, 50 mg, 100 mg, 250 mg and 500 mg is generally administered. Daily doses for chronic administration in humans will be in the range of about 0.3

PREPARATION 1

(1) To a solution of 2-amino-4-methoxycarbonylphenyl trifluoromethanesulfonate (2.6 g) in a mixture of pyridine (5.6 ml) and dichloromethane (20 ml) was added benzyl chloroformate (2.08 ml) at 0° C., and the mixture was stirred at 20° C. for 4.5 hours. The mixture was diluted with dichloromethane and washed successively with diluted hydrochloric acid, aqueous sodium bicarbonate and brine. The organic layer was dried over sodium sulfate and evaporated in vacuo. The residue was chromatographed on silica gel eluting with dichloromethane to give 2-benzyloxycarbonylamino-4-methoxycarbonylphenyl trifluoromethanesulfonate (2.61 g) as colorless crystals.

NMR (CDCl$_3$, $\delta$): 3.92 (3H, s), 5.23 (2H, s), 6.89 (1H, br s), 7.3–7.45 (6H, m), 7.83 (1H, dd, J=1, 8 Hz), 8.61 (1H, s).

(2) A mixture of 2-benzyloxycarbonylamino-4-methoxycarbonylphenyl trifluoromethanesulfonate (1.01 g), 1-pentynyl(tributyl)stannane (1.02 g), lithium chloride (0.29 g) and tetrakis(triphenylphosphine)palladium (80 mg) in dioxane (24 ml) was heated at 100° C. for 2 hours. The solvent was evaporated in vacuo and the residue was chromatographed on silica gel eluting with a mixture of hexane and ethyl acetate (4:1) to give methyl 3-benzyloxycarbonylamino-4-(1-pentynyl)benzoate (536 mg) as colorless crystals.

NMR (CDCl$_3$, $\delta$): 1.03 (3H, t, J=7 Hz), 1.67 (2H, m), 2.44 (2H, t, J=7 Hz), 3.87 (3H, s), 5.23 (2H, s), 7.25–7.7 (7H, m), 8.78 (1H, s).

(3) To a solution of methyl 3-benzyloxycarbonylamino-4-(1-pentynyl)benzoate (949 mg) in tetrahydrofuran (24 ml) was added gold(III)sodium chloride (24 mg) under argon atmosphere, and the mixture was heated under reflux for 100 minutes. The solvent was evaporated in vacuo and the residue was chromatographed on silica gel eluting with a mixture of hexane, dichloromethane, and ethyl acetate (6:3:2) to give methyl 1-benzyloxycarbonyl-2-propylindole-6-carboxylate (852 mg) as colorless crystals.

NMR (CDCl$_3$, $\delta$): 0.98 (3H, t, J=7 Hz), 1.71 (2H, m), 2.97 (2H, t, J=7 Hz), 3.90 (3H, s), 5.49 (2H, s), 6.39 (1H, s), 7.3–7.6 (6H, m), 7.91 (1H, dd, J=1, 8 Hz), 8.80 (1H, s).

(4) To a solution of methyl 1-benzyloxycarbonyl-2-propylindole-6-carboxylate (200 mg) in a mixture of methanol and ethyl acetate (1:1, 8 ml) was added 10% palladium on carbon (30 mg), and the mixture was stirred under hydrogen atmosphere or 20 minutes. The catalyst was removed by filtration through celite and washed with methanol. The filtrate was evaporated in vacuo to give methyl 2-propylindole-6-carboxylate (112 mg) as colorless crystals.

NMR (CDCl$_3$, $\delta$): 1.02 (3H, t, J=7 Hz), 1.78 (2H, m), 2.76 (2H, t, J=7 Hz), 3.93 (3H, s), 6.29 (1H, s), 7.51 (1H, d, J=8 Hz), 7.77 (1H, d, J=8 Hz), 8.04 (1H, s), 8.15 (1H, br s).

(5) To a stirring suspension of aluminum chloride (294 mg) and acetyl chloride (0.08 ml) in dichloromethane (10 ml) was added methyl 2-propylindole-6-carboxylate (200 mg), and the mixture was stirred at 20° C. for 1 hour. The resulting mixture was poured onto ice and extracted with ethyl acetate. The combined organic chase was washed with aqueous sodium bicarbonate and brine, then dried over sodium sulfate and evaporated in vacuo. The residue was triturated with isopropyl ether to give methyl 3-acetyl-2-propylindole-6-carboxylate (78 mg) as colorless crystals.

NMR (CDCl$_3$, δ): 1.02 (3H, t, J=7 Hz), 1.61 (2H, m), 2.69 (2H, s), 3.18 (2H, t, J=7 Hz), 3.96 (3H, s), 7.93 (1H, dd, J=1, 8 Hz), 8.01 (1H, d, J=8 Hz), 8.12 (1H, d, J=1 Hz), 8.88 (1H, br s).

PREPARATION 2

Methyl 3-isobutyryl-2-propylindole-6-carboxylate (474 mg) was prepared from methyl 2-propylindole-6-carboxylate (700 mg) and isobutyryl chloride (1.01 ml) in a similar manner to that of Preparation 1 (5).

NMR (CDCl$_3$, δ): 1.04 (3H, t, J=8 Hz), 1.28 (6H, d, J=8 Hz), 1.83 (2H, sextet, J=8 Hz), 3.18 (2H, t, J=8 Hz), 3.52 (2H, septet, J=8 Hz), 3.96 (3H, s), 7.92 (2H, s), 8.16 (1H, s), 9.13 (1H, br s).

PREPARATION 3

Methyl 3-propionyl-2-propylindole-6-carboxylate (298 mg) was prepared from methyl 2-propylindole-6-carboxylate (500 mg) and propionyl chloride (0.40 ml) in a similar manner to that of Preparation 1 (5).

NMR (CDCl$_3$, δ): 1.04 (3H, t, J=8 Hz), 1.29 (3H, t, J=8 Hz), 1.83 (2H, sextet, J=8 Hz), 3.06 (2H, q, J=8 Hz), 3.20 (2H, t, J=8 Hz), 3.96 (3H, s), 7.93 (1H, dd, J=1, 8 Hz), 8.00 (1H, d, J=8 Hz), 8.15 (1H, d, J=1 Hz), 9.22 (1H, s),

PREPARATION 4

(1) Methyl 3-benzyloxycarbonylamino-4-(4-methyl-1-pentynyl)benzoate (2.25 g) was prepared from 2-benzyloxycarbonylamino-4-methoxycarbonylphenyl trifluoromethanesulfonate (3.0 g) and (4-methyl-1-pentynyl)(tributyl)stannane (2.7 g) in a similar manner to that of Preparation 1 (2).

NMR (CDCl$_3$, δ): 1.05 (6H, d, J=8 Hz), 1.88–2.02 (1H, m), 2.40 (2H, d, J=8 Hz), 3.90 (3H, s), 5.25 (2H, s), 7.32–7.45 (6H, m), 7.52 (1H, s), 7.66 (1H, d, J=8 Hz), 8.78 (1H, s).

(2) Methyl 1-benzyloxycarbonyl-2-isobutylindole-6-carboxylate (1.67 g) was prepared from methyl 3-benzyloxycarbonylamino-4-(4-methyl-1-pentynyl)benzoate (2.15 g) in a similar manner to that of Preparation 1 (3).

NMR (CDCl$_3$, δ): 0.90 (6H, d, J=8 Hz), 1.90–2.04 (1H, m), 2.86 (2H, d, J=8 Hz), 3.90 (3H, s), 5.48 (2H, s), 6.38 (1H, s), 7.40–7.56 (6H, m), 7.91 (1H, d, J=8 Hz), 8.82 (1H, s).

(3) Methyl 2-isobutylindole-6-carboxylate (752 mg) was prepared from methyl 1-benzyloxycarbonyl-2-isobutylindole-6-carboxylate (1.5 g) in a similar manner to that of Preparation 1 (4).

NMR (CDCl$_3$, δ): 0.98 (6H, d, J=8 Hz), 1.95–2.08 (1H, m), 2.66 (2H, d, J=8 Hz), 3.92 (3H, s), 6.28 (1H, s), 7.53 (1H, d, J=8 Hz), 7.76 (1H, d, J=8 Hz), 8.08 (1H, s), 8.23 (1H, br s).

(4) Methyl 2-isobutyl-3-isobutyrylindole-6-carboxylate (246 mg) was prepared from methyl 2-isobutylindole-6-carboxylate (300 mg) and isobutyryl chloride (0.41 ml) in a similar manner to that of Preparation 1 (5).

NMR (CDCl$_3$, δ): 0.98 (6H, d, J=8 Hz), 1.27 (1H, d, J=8 Hz), 2.10–2.23 (1H, m), 3.06 (2H, d, J=8 Hz), 3.52 (2H, septet, J=8 Hz), 3.96 (3H, s), 7.92 (2H, s), 8.16 (1H, s), 9.02 (1H, s).

PREPARATION 5

(1) Methyl 3-benzyloxycarbonylamino-4-(1-butynyl)benzoate (646 mg) was prepared from 2-benzyloxycarbonylamino-4-methoxycarbonylphenyl trifluoromethanesulfonate (1.82 g) and 1-butynyl(tributyl)stannane (1.51 g) in a similar manner to that of Preparation 1 (2).

NMR (CDCl$_3$, δ): 1.26 (3H, t, J=7 Hz), 2.50 (2H, q, J=7 Hz), 3.91 (3H, s), 5.24 (2H, s), 7.3–7.5 (7H, m), 7.65 (1H, dd, J=1, 8 Hz), 8.79 (1H, br s).

(2) Methyl 1-benzyloxycarbonyl-2-ethylindole-6-carboxylate (551 mg) was prepared from methyl 3-benzyloxycarbonylamino-4-(1-butynyl)benzoate (640 mg) in a similar manner to that of Preparation 1 (3).

NMR (CDCl$_3$, δ): 1.30 (3H, t, J=7 Hz), 3.05 (2H, q, J=7 Hz), 3.88 (3H, s), 4.98 (2H, s), 6.92 (1H, s), 7.35–7.60 (6H, m), 7.89 (1H, dd, J=1, 8 Hz), 8.79 (1H, s).

(3) Methyl 2-ethylindole-6-carboxylate (306 mg) was prepared from methyl 1-benzyloxycarbonyl-2-ethylindole-6-carboxylate (546 mg) in a similar manner to that of Preparation 1 (4).

NMR (CDCl$_3$, δ): 1.38 (3H, t, J=7 Hz), 2.82 (2H, q, J=7 Hz), 3.91 (3H, s), 6.30 (1H, s), 7.50 (1H, d, J=8 Hz), 7.75 (1H, d, J=8 Hz), 8.03 (1H, s), 8.14 (1H, br s).

(4) Methyl 2-ethyl-3-propionylindole-6-carboxylate (435 mg) was prepared from methyl 2-ethylindole-6-carboxylate (660 mg) and propionyl chloride (0.62 ml) in a similar manner to that of Preparation 1 (5).

NMR (CDCl$_3$, δ): 1.29 (3H, t, J=7 Hz), 1.39 (3H, t, J=7 Hz), 3.06 (2H, t, J=7 Hz), 3.26 (2H, t, J=7 Hz), 3.94 (3H, s), 7.24 (1H, s), 7.92 (1H, d, J=8 Hz), 7.98 (1H, d, J=8 Hz), 8.14 (1H, s), 8.92 (1H, br s).

PREPARATION 6

(1) Methyl 3-isobutyrylindole-6-carboxylate (618 mg) was prepared from methyl indole-6-carboxylate (500 mg) and isobutyryl chloride (0.84 ml) in a similar manner to that of Preparation 1 (5).

NMR (CDCl$_3$, δ): 1.23 (6H, d, J=7 Hz), 3.35 (1H, m), 3.96 (3H, s), 7.93–8.06 (2H, m), 8.19 (1H, s), 8.46 (1H, d, J=8 Hz), 8.96 (1H, br s).

(2) To a solution of methyl 3-isobutyrylindole-6-carboxylate (146 mg) in tetrahydrofuran (5 ml) was added 1M solution of brane-tetrahydrofuran complex in tetrahydrofuran (1.8 ml), and the mixture was stirred at 50° C. for 1 hour. The resulting mixture was evaporated in vacuo, and the residue was quenched with aqueous ammonium chloride and extracted with ethyl acetate. The organic phase was washed with brine, and dried over sodium sulfate. After evaporation of solvent, the residue was chromatographed on silica gel eluting with a mixture of hexane and ethyl acetate (2:1) to give methyl 3-isobutylindole-6-carboxylate (105 mg) as colorless crystals.

NMR (CDCl$_3$, δ): 0.94 (6H, d, J=7 Hz), 1.98 (1H, m), 2.62 (2H, d, J=7 Hz), 3.93 (3H, s), 7.12 (1H, s), 7.61 (1H, d, J=8 Hz), 7.78 (1H, d, J=8 Hz), 8.08 (1H, s), 8.16 (1H, br s).

(3) Methyl 2-acetyl-3-isobutylindole-6-carboxylate (43 mg) was prepared from methyl 3-isobutylindole-6-carboxylate (99 mg) and acetyl chloride (0.073 ml) in a similar manner to that of Preparation 1 (5).

NMR (CDCl$_3$, δ): 1.01 (6H, d, J=7 Hz), 2.02 (1H, m), 2.69 (3H, s), 2.98 (2H, d, J=7 Hz), 3.96 (3H, s), 7.73 (1H, d, J=8 Hz), 7.79 (1H, d, J=8 Hz), 8.11 (1H, s), 9.09 (1H, br s).

PREPARATION 7

(1) Methyl 3-acetylindole-6-carboxylate (470 mg) was prepared from methyl indole-6-carboxylate (655 mg) and acetyl chloride (0.27 ml) in a similar manner to that of Preparation 1 (5).

NMR (DMSO-d$_6$, δ): 2.46 (3H, s), 3.88 (3H, s), 7.79 (1H, d, J=8 Hz), 8.10 (1H, s), 8.24 (1H, d, J=8 Hz), 8.52 (1H, s).

2) Methyl 3-ethylindole-6-carboxylate (327 mg) was prepared from methyl 3-acetylindole-6-carboxylate (470 mg) in a similar manner to that of Preparation 6 (2).

NMR (CDCl$_3$, δ): 1.33 (3H, t, J=7 Hz), 2.78 (2H, q, J=7 Hz), 3.93 (3H, s), 7.15 (1H, s), 7.63 (1H, d, J=8 Hz), 7.79 (1H, d, J=8 Hz), 8.12 (1H, s), 8.14 (1H, br s).

(3) Methyl 3-ethyl-2-propionylindole-6-carboxylate (65.7 mg) was prepared From methyl 3-ethylindole-6-carboxylate (184 mg) and propionyl chloride (0.17 ml) in a similar manner to that of Preparation 1 (5).

NMR (CDCl$_3$, δ): 1.29 (3H, t, J=7 Hz), 1.34 (3H, t, J=7 Hz), 3.03 (2H, q, J=7 Hz), 3.14 (2H, q, J=7 Hz), 3.94 (3H, s), 7.73 (1H, d, J=8 Hz), 7.79 (1H, d, J=8 Hz), 8.13 (1H, s), 9.10 (1H, br s).

PREPARATION 8

(1) 3-Isobutyryl-2-propylindole-6-carboxylic acid (853 mg) was prepared from methyl 3-isobutyryl-2-propylindole-6-carboxylate (935 mg) in a similar manner to that of Example 2.

NMR (DMSO-d$_6$, δ): 0.95 (3H, t, J=8 Hz), 1.14 (6H, d, J=8 Hz), 1.72 (2H, sextet, J=8 Hz), 3.08 (2H, t, J=8 Hz), 3.46 (1H, septet, J=8 Hz), 7.76 (1H, d, J=9 Hz), 7.92 (1H, dd, J=1, 9 Hz), 8.00 (1H, d, J=1 Hz).

(2) 3-Isobutyryl-2-propylindole-6-carboxamide (853 mg) was prepared from 3-isobutyryl-2-propylindole-6-carboxylic acid (935 mg) in a similar manner to that of Example 6.

NMR (DMSO-d$_6$, δ): 0.95 (3H, t, J=8 Hz), 1.15 (6H, d, J=8 Hz), 1.70 (2H, sextet, J=8 Hz), 3.07 (2H, t, J=8 Hz), 3.46 (1H, septet, J=8 Hz), 7.26 (1H, br s), 7.72 (1H, d, J=9 Hz), 7.87 (1H, dd, J=1, 9 Hz), 7.94 (1H, d, J=1 Hz).

PREPARATION 9

Methyl 3-benzoyl-2-propylindole-6-carboxylate (289 mg) was prepared from methyl 2-propylindole-6-carboxylate (500 mg) and benzoyl chloride (970 mg) in a similar manner to that of Preparation 1 (5).

NMR (CDCl$_3$, δ): 0.82 (3H, t, J=8 Hz), 1.66 (2H, sextet, J=8 Hz), 2.78 (2H, t, J=8 Hz), 3.85 (3H, s), 7.29 (1H, d, J=8 Hz), 7.49–7.54 (2H, m), 7.60–7.64 (4H, m), 8.02 (1H, s).

PREPARATION 10

To a stirred solution of methyl 2-propylindole-6-carboxylate (911 mg) in acetonitrile (15 ml) was added chlorosulfonylisocyanate (0.6 g) in acetonitrile (1.5 ml) at 0° C. The mixture was stirred at 0° C. for 30 minutes, then N,N-dimethylformamide (0.35 g) in acetonitrile (15 ml) was added at 0° C. The resultant mixture was stirred at 20° C. for 40 minutes, and then poured into water. The mixture was extracted with methylene chloride three times, and the combined organic phase was dried over sodium sulfate and evaporated in vacuo. The residue was chromatographed on silica gel eluting with a mixture of ethyl acetate and hexane (1:3) to give the crystals which were recrystallized from a mixture or ethyl acetate and hexane to give methyl 3-cyano-2-propylindole-6-carboxylate (535 mg) as colorless crystals.

mp: 148.5–150° C.; IR (KBr): 3251, 2218, 1710, 1284, 1218 cm$^{-1}$; NMR (CDCl$_3$, δ): 1.07 (3H, t,=7 Hz), 1.89 (2H, sextet, J=7 Hz), 3.00 (2H, t, J=7 Hz), 3.99 (3H, s), 7.70 (1H, d, J=7.5 Hz), 7.95 (1H, d, J=7.5 Hz), 8.19 (1H, s), 9.05 (1H, br s); MASS (m/z): 243 (M$^+$+1), 76 (bp).

PREPARATION 11

Methyl 3-acetyl-2-ethylindole-6-carboxylate (106 mg) was prepared from methyl 2-ethylindole-6-carboxylate (237 mg) and acetyl chloride (0.19 ml) in a similar manner to that of Preparation 1 (5).

NMR (CDCl$_3$, δ): 1.42 (3H, t, J=7 Hz), 2.69 (3H, s), 3.27 (2H, q, J=7 Hz), 3.96 (3H, s), 7.93 (1H, d, J=8 Hz), 8.01 (1H, d, J=8 Hz), 8.12 (1H, s), 8.93 (1H, br s).

PREPARATION 12

Methyl 2-ethyl-3-isobutyrylindole-6-carboxylate (200 mg) was prepared from methyl 2-ethylindole-6-carboxylate (317 mg) and isobutyryl chloride (0.36 ml) in a similar manner to that of Preparation 1 (5).

NMR (CDCl$_3$, δ): 1.28 (6H, d, J=1 Hz), 1.38 (3H, t, J=7 Hz), 3.25 (2H, q, J=7 Hz), 3.51 (1H, m), 3.94 (3H, s), 7.92 (2H, s), 8.13 (1H, s), 8.92 (1H, br s).

PREPARATION 13

(1) Methyl 3-benzyloxycarbonylamino-4-(1-propynyl)benzoate (1.34 g) was prepared from 2-benzyloxycarbonylamino-4-methoxycarbonylphenyl trifluoromethanesulfonate (2.1 g) and tributyl (1-propynyl)stannane (2.49 g) in a similar manner to that of Preparation 1 (2).

NMR (CDCl$_3$, δ): 2.14 (3H, s), 3.91 (3H, s), 5.24 (2H, s), 7.35–7.50 (6H, m), 7.65 (1H, d, J=8 Hz), 8.82 (1H, s).

(2) Methyl 1-benzyloxycarbonyl-2-methylindole-6-carboxylate (1.2 g) was prepared from methyl 3-benzyloxycarbonylamino-4-(1-propynyl)benzoate (1.32 g) in a similar manner to that of Preparation 1 (3).

NMR (CDCl$_3$, δ): 2.63 (3H, s), 3.89 (3H, s), 5.50 (2H, s), 6.38 (1H, s), 7.35–7.56 (6H, m), 7.91 (1H, d, J=8 Hz), 8.81 (1H, s).

(3) Methyl 2-methylindole-6-carboxylate (562 mg) was prepared from methyl 1-benzyloxycarbonyl-2-methylindole-6-carboxylate (1.18 g) in a similar manner to that of Preparation 1 (4).

NMR (CDCl$_3$, δ): 2.49 (3H, s), 3.92 (3H, s), 6.28 (1H, s), 7.51 (1H, d, J=8 Hz), 7.77 (1H, d, J=8 Hz), 8.03 (1H, s), 8.12 (1H, br s).

(4) Methyl 3-isobutyryl-2-methylindole-6-carboxylate (142 mg) was prepared from methyl 2-methylindole-6-carboxylate (305 mg) and isobutyryl chloride (0.47 ml) in a similar manner to that of Preparation 1 (5).

NMR (CDCl$_3$, δ): 1.26 (6H, d, J=7 Hz), 2.81 (3H, s), 3.47 (1H, m), 3.93 (3H, s), 7.92 (1H, d, J=8 Hz), 8.09 (1H, s), 8.85 (1H, br s).

PREPARATION 14

(1) Methyl 3-benzyloxycarbonylamino-4-(3-methoxy-1-propynyl)benzoate (4.23 g) was prepared from 2-benzyloxycarbonylamino-4-methoxycarbonylphenyl trifluoromethanesulfonate (7.73 g) and (3-methoxy-1-propynyl)tributylstannane (6.67 g) in a similar manner to that of Preparation 1 (2).

NMR (CDCl$_3$, δ): 3.44 (3H, s), 3.91 (3H, s), 4.38 (2H, s), 1.23 (2H, s), 7.3–7.5 (7H, m), 7.69 (1H, d, J=8 Hz, 8.82 (1H, s).

(2) Methyl 1-benzyloxycarbonyl-2-methoxymethylindole-6-carboxylate (2.14 g) was prepared from methyl 3-benzyloxycarbonylamino-4-(3-methoxy-1-propynyl)benzoate (4.23 g) in a similar manner to that of Preparation 1 (3).

NMR (CDCl$_3$, δ): 3.44 (3H, s), 3.88 (3H, s), 4.80 (2H, s), 5.49 (2H, s), 6.70 (1H, s), 7.38–7.58 (6H, m), 7.92 (1H, d, J=8 Hz), 8.80 (1H, s).

(3) Methyl 2-methoxymethylindole-6-carboxylate (0.42 g) was prepared from methyl 1-benzyloxycarbonyl-2-methoxymethylindole-6-carboxylate (2.12 g) in a similar manner to that of Preparation 1 (4).

NMR (CDCl$_3$, δ): 3.41 (3H, s), 3.94 (3H, s), 4.64 (2H, s), 6.47 (1H, s), 7.59 (1H, d, J=8 Hz), 7.80 (1H, d, J=8 Hz), 8.11 (1H, s), 8.59 (1H, br s).

(4) Methyl 3-isobutyryl-2-methoxymethylindole-6-carboxylate (146 mg) was prepared from methyl 2-methoxymethylindole-6-carboxylate (396 mg) and isobutyryl chloride (0.53 ml) in a similar manner to that of Preparation 1 (5).

NMR (CDCl$_3$, δ): 1.26 (6H, d, J=7 Hz), 3.48 (1H, m), 3.58 (3H, s), 3.94 (3H, s), 5.03 (2H, s), 7.88 (1H, d, J=8 Hz), 7.96 (1H, d, J=8 Hz), 8.18 (1H, s), 9.45 (1H, br s).

PREPARATION 15

(1) To a solution of methyl 2-propylindole-6-carboxylate (300 mg) in dichloromethane (10 ml) was added a 1M solution of tin(IV) chloride in dichloromethane (2.76 ml) at 20° C. The mixture was stirred at 20° C. for 30 minutes, then methoxyacetyl chloride (0.25 ml) was added. After stirred at 20° C. or 30 minutes, the mixture was partitioned between ethyl acetate and water. The organic layer was washed with water and brine, dried over magnesium sulfate, and evaporated in vacuo. The residue was chromatographed on silica gel eluting with a mixture of ethyl acetate and hexane (1:10–1:1) to give methyl 3-methoxyacetyl-2-propylindole-6-carboxylate (135 mg) as pale yellow crystals.

mp: 127–129° C.; NMR (CDCl$_3$, δ): 1.05 (3H, t, J=8 Hz), 1.83 (2H, sextet, J=8 Hz), 3.02 (2H, t, J=3 Hz), 3.57 (3H, 5), 3.97 (3H, s), 4.72 (2H, s), 7.83 (1H, d, J=6 Hz), 7.95 (1H, d, J=8 Hz), 8.18 (1H, s), 9.38 (1H, br s).

(2) 3-Methoxyacetyl-2-propylindole-6-carboxylic acid (108 mg) was prepared from methyl 3-methoxyacetyl-2-propylindole-6-carboxylate (120 mg) in a similar manner to that of Example 2.

mp: >250° C. NMR (DMSO-d$_6$, δ): 0.97 (3H, t, J=8 Hz), 1.74 (2H, sextet, J=8 Hz), 3.09 (2H, t, J=8 Hz), 3.38 (3H, s), 4.61 (2H, s), 7.75 (1H, d, J=8 Hz), 7.91 (1H, d, J=8 Hz), 8.00 (1H, s).

(3) 3-Methoxyacetyl-2-propylindole-6-carboxamide (89 mg) was prepared from 3-methoxyacetyl-2-propylindole-6-carboxylic acid (95 mg) in a similar manner to that of Example 6.

mp: 165–167° C. NMR (DMSO-d$_6$, δ): 0.95 (3H, t, J=8 Hz), 1.74 (2H, sextet, J=8 Hz), 3.06 (2, t, J=8 Hz), 3.38 (3H, s), 4.60 (2H, s), 7.25 (1H, br s), 7.70 (1H, d, J=8 Hz), 7.84 (1H, d, J=8 Hz), 7.94 (1H, 5), 7.97 (1H, br s).

PREPARATION 16

To a solution of methyl 2-amino-3-hydroxybenzoate (882 mg) in pyridine (2 ml) was added acetic anhydride (1.2 ml) and the mixture was stirred at 20° C. for 8 hours. The reaction mixture was diluted with diisopropyl ether, and the resulting solid was collected and washed with diisopropyl ether. The solid was triturated with diisopropyl ether to give methyl 2-acetamido-3-acetoxybenzoate (1.25 g) as solid.

NMR (CDCl$_3$, δ): 2.18 (3H, s), 2.26 (3H, s), 3.90 (3H, s), 7.27 (1H, t, J=8 Hz), 7.39 (1H, d, J=8 Hz), 7.83 (1H, d, J=8 Hz), 9.09 (1H, br s).

PREPARATION 17

The following compounds described in (1) to (4) were prepared in a similar manner to that of Preparation 16.

(1) Methyl 3-acetamido-4-acetoxybenzoate

NMR (CDCl$_3$, δ): 2.21 (3H, s), 2.37 (3H, s), 3.93 (3H, s), 7.22 (1H, d, J=8 Hz), 7.83 (1H, d, J=8 Hz), 8.22 (1H, s).

(2) Methyl 4-acetamido-3-acetoxybenzoate

NMR (DMSO-d$_6$, δ): 2.12 (3H, s), 2.33 (3H, s), 3.84 (3H, s), 7.73 (7H, d, J=2 Hz), 7.82 (1H, dd, J=2, 8 Hz), 8.22 (1H, d, J=8 Hz), 9.64 (1H, s).

(3) Methyl 3-acetamido-2-acetoxybenzoate

NMR (CDCl$_3$, δ): 2.20 (3H, s), 2.43 (3H, s), 3.91 (3H, s), 7.29 (1H, t, J=8 Hz), 7.74 (1H, d, J=8 Hz), 8.51 (1H, d, J=8 Hz).

(4) Methyl 3-acetamido-4-trifluoromethanesulfonyloxyphenyl-acetate mp: 68.5–70° C.; IR (KBr): 3341, 1727, 1699, 1437, 1425 cm$^{-1}$; NMR (CDCl$_3$, δ): 2.24 (3H, s), 3.68 (3H, s), 3.73 (3H, s), 7.11 (1H, dd, J=8, 1 Hz), 7.24–7.30 (2H, m), 8.19 (1H, s); MASS (m/z): 354 (M$^+$–1), 149 (bp).

PREPARATION 18

To a solution of methyl 2-acetamido-3-acetoxybenzoate (1.72 g) in methanol (9 ml) was added powdered potassium carbonate (1.4 g), and the mixture was stirred for 20 minutes. The resulting solid was removed by filtration and washed with methanol. The filtrate was evaporated in vacuo, and the residue was acidified with 1N hydrochloric acid and extracted with ethyl acetate. The organic phase was washed with brine, dried over sodium sulfate and evaporated in vacuo. The residue was triturated with a mixture of isopropyl ether and hexane to give methyl 2-acetamido-3-hydroxybenzoate (1.21 g) as solid.

NMR (CDCl$_3$, δ): 2.33 (3H, s), 3.93 (3H, s), 7.14 (1H, t, J=8 Hz), 7.23 (1H, d, J=8 Hz), 7.61 (1H, d, J=8 Hz), 9.88 (1H, s).

PREPARATION 19

The following compounds described in (1) to (3) were prepared in a similar manner to that of Preparation 18.

(1) Methyl 3-acetamido-4-hydroxybenzoate

NMR (DMSO-d$_6$, δ): 2.11 (3H, s), 3.80 (3H, s), 6.93 (1H, 4, J=8 Hz), 7.56 (1H, d, J=2 Hz), 8.47 (1H, s), 9.20 (1H, s).

(2) Methyl 4-acetamido-3-hydroxybenzoate

NMR (DMSO-d$_6$, δ): 2.14 (3H, s), 3.78 (3H, s), 7.37 (1H, dd, J=2, 8 Hz), 7.45 (1H, d, J=2 Hz), 8.08 (1H, d, J=8 Hz), 9.32 (1H, s).

(3) Methyl 4-acetamido-2-hydroxybenzoate

NMR (CDCl$_3$, δ): 2.33 (3H, s), 4.97 (3H, s), 6.90 (1H, t, J=8 Hz), 7.56 (1H, d, J=8 Hz), 7.81 (1H, br s), 8.57 (1H, d, J=8 Hz).

PREPARATION 20

To a solution of methyl 2-acetamido-3-hydroxybenzoate (1.2 g) in a mixture of pyridine (1.4 ml) and dichloromethane (2 ml) was added slowly trifluoromethanesulfonic anhydride (1.1 ml) at 0° C. When addition was completed, the mixture was stirred at 20° C. for 20 minutes. The resulting mixture was poured into ice and extracted with ethyl acetate. The organic chase was washed with 1N hydrochloric acid, aqueous sodium bicarbonate and brine, dried over sodium sulfate and evaporated in vacuo. The residue was triturated with a mixture of dichloromethane and hexane to give methyl 2-acetamido-3-trifluoromethanesulfonyloxybenzoate (1.78 g) as solid.

NMR (CDCl$_3$, δ): 2.24 (3H, s), 3.93 (3H, s), 7.34 (1H, t, J=8 Hz), 7.49 (1H, d, J=6 Hz), 7.99 (1H, d, J=8 Hz), 8.90 (1H, br s).

PREPARATION 21

The Following compounds described in (1) to 4) were prepared in a similar manner to that of preparation 20.

(1) Methyl 3-acetamido-4-trifluoromethanesulfonyloxybenzoate

NMR (CDCl$_3$, δ): 2.25 (3H, s), 3.93 (3H, s), 7.37 (1H, d, J=8 Hz), 7.92 (1H, m), 8.86 (1H, br s).

(2) Methyl 4-acetamido-3-trifluoromethanesulfonyloxybenzoate

NMR (CDCl$_3$, δ): 2.27 (3H, s), 3.94 (3H, s), 7.51 (1H, br s), 7.94 (1H, d, J=2 Hz), 8.05 (1H, dd, J=2, 8 Hz), 8.47 (1H, d, J=8 Hz).

(3) Methyl 3-acetamido-2-trifluoromethanesulfonyloxyphenyl-acetate

NMR (CDCl$_3$, δ): 2.23 (3H, s), 3.93 (3H, s), 7.40 (1H, br s), 7.43 (1H, t, J=8 Hz), 7.76 (1H, d, J=8 Hz), 8.39 (1H, d, J=8 Hz).

(4) Methyl 3-nitro-4-trifluoromethanesulfonyloxyphenyl-acetate mp: 44–45° C. IR (KBr): 1736, 1544, 1434, 1340 cm$^{-1}$; NMR (CDCl$_3$, δ): 3.75 (2H, s), 3.76 (3H, s), 7.41 (1H, d, J=8 Hz), 7.68 (1H, dd, J=8, 1 Hz), 8.10 (1H, d, J=1 Hz); MASS (m/z): 343 (M$^+$), 135 (bp).

PREPARATION 22

The following compounds described in (1) to (3) were prepared from a similar manner to that of Preparation 1 (2).

(1) Methyl 2-acetamido-3-(1-pentynyl)benzoate

NMR (CDCl$_3$, δ): 1.06 (3H, t, J=7 Hz), 1.64 (2H, m), 2.20 (3H, s), 2.43 (2H, t, J=7 Hz), 3.88 (3H, s), 7.16 (1H, t, J=8 Hz), 7.57 (1H, d, J=8 Hz), 7.76 (1H, d, J=8 Hz), 8.42 (1H, br s).

(2) Methyl 4-acetamido-3-(1-pentynyl)benzoate

NMR (CDCl$_3$, δ): 1.11 (3H, t, J=8 Hz), 1.68 (2H, sextet, J=8 Hz), 2.24 (3H, s), 2.52 (2H, t, J=8 Hz), 3.89 (3H, s), 7.94 (1H, dd, J=1, 8 Hz), 8.07 (1H, d, J=1 Hz), 8.12 (1H, br s), 8.48 (1H, d, J=8 Hz).

(3) Methyl 3-acetamido-2-(1-pentynyl)benzoate

NMR (CDCl$_3$, δ): 1.12 (3H, t, J=7 Hz), 1.73 (2H, m), 2.22 (3H, s), 2.59 (2H, t, J=7 Hz), 3.91 (3H, s), 7.32 (1H, t, J=8 Hz), 7.63 (1H, d, J=8 Hz), 8.29 (1H, br s), 8.62 (7H, d, J=8 Hz).

PREPARATION 23

A mixture of methyl 3-acetamido-4-trifluoromethanesulfonyloxybenzoate (1.43 g), methyl 5-hexynoate (582 mg), palladium(II) chloride (14 .9 mg), triphenylphosphine (43.8 mg) and cooper(I) chloride (32 mg) in diethylamine (18 ml) was stirred at 20° C. for 14 hours. The solvent was evaporated in vacuo an the residue was chromatographed on silica gel eluting with a mixture of hexane and ethyl acetate (1:2) to give methyl 3-acetamido-4-(5-methoxycarbonyl-1-pentynyl)-benzoate (1.15 g) as colorless crystals.

NMR (CDCl$_3$, δ): 2.02 (2H, m), 2.27 (3H, s), 2.53 (2H, t, J=7 Hz), 2.63 (2H, t, J=7 Hz), 3.68 (3H, s), 3.90 (3H, s), 7.41 (1H, d, J=8 Hz), 7.70 (1H, d, J=8 Hz), 8.00 (1H, br s), 8.98 (1H, br s).

PREPARATION 24

The following compounds described in (1) to (3) were prepared in a similar manner to that of Preparation 23.

(1) Methyl 3-acetamido-4-(1-ethynyl)benzoate

NMR (CDCl$_3$, δ): 1.12 (3H, t, J=7 Hz), 1.65 (2H, m), 2.23 (3H, s), 2.54 (2H, t, J=7 Hz), 3.90 (3H, s), 7.43 (1H, dd, J=1, 8 Hz), 7.70 (1H, m), 7.95 (1H, br s), 8.98 (1H, br s).

(2) Methyl 3-acetamido-4-(4-methoxycarbonyl-1-butynyl)benzoate

NMR (CDCl$_3$, δ): 2.32 (3H, s), 2.68 (2H, m), 2.80 (2H, m), 3.73 (3H, s), 3.89 (3H, s), 7.38 (1H, d, J=8 Hz), 7.67 (1H, m), 8.28 (1H, br s), 9.04 (1H, br s).

(3Methyl 3-acetamido-4-(1-pentynyl)phenylacetate mp: 77–78° C.; IR (KBr): 3293, 1739, 1699, 1665, 1428 cm$^{-1}$; NMR (CDCl$_3$, δ): 1.09 (3H, t, J=7 Hz), 1.69 (2H, sextet, J=7 Hz), 2.22 (3H, s), 2.49 (2H, t, J=7 Hz), 3.64 (2H, s), 3.70 (3H, s), 6.94 (1H, d, J=7.5 Hz), 7.31 (1H, d, J=7.5 Hz), 7.93 (1H, br s), 8.33 (1H, s); MASS (m/z): 274 (M$^+$+1, bp).

PREPARATION 25

The following compounds described in (1) to (7) were prepared in a similar manner to that of Preparation 1 (3).

(1) Methyl 1-acetyl-2-(3-methoxycarbonylpropyl)indole-6-carboxylate

NMR (CDCl$_3$, δ): 2.08 (2H, m), 2.43 (2H, t, J=7 Hz), 2.66 (3H, s), 3.12 (2H, t, J=7 Hz), 3.67 (3H, s), 3.94 (3H, s), 6.49 (1H, s), 7.52 (1H, d, J=8 Hz), 7.93 (1H, d, J=8 Hz), 8.47 (1H, s).

(2) Methyl 1-acetyl-2-propylindole-7-carboxylate

NMR (CDCl$_3$, δ): 1.04 (3H, t, J=7 Hz), 1.78 (2H, m), 2.39 (3H, s), 2.79 (2H, m), 3.91 (3H, s), 6.38 (1H, m), 7.23 (1H, t, J=8 Hz), 7.68 (1H, d, J=8 Hz), 7.79 (1H, d, J=8 Hz).

(3) Methyl 1-acetyl-2-propylindole-6-carboxylate

NMR (CDCl$_3$, δ): 1.06 (3H, t, J=7 Hz), 1.77 (2H, m), 2.82 (3H, s), 3.03 (2H, t, J=8 Hz), 3.94 (3H, s), 6.47 (1H, s), 7.49 (1H, d, J=8 Hz), 7.94 (1H, d, J=8 Hz), 8.53 (1H, s).

(4) Methyl 1-acetyl-2-propylindole-5-carboxylate

NMR (CDCl$_3$, δ): 1.05 (3H, t, J=8 Hz), 1.75 (2H, sextet, J=8 Hz), 2.76 (3H, s), 2.98 (2H, t, J=8 Hz), 3.94 (3H, s), 6.48 (1H, d, J=1 Hz), 7.87 (1H, d, J=8 Hz), 7.95 (1H, d, J=8 Hz), 8.18 (1H, s).

(5) Methyl 1-acetyl-2-propylindole-4-carboxylate

NMR (CDCl$_3$, δ): 1.07 (3H, t, J=7 Hz), 1.80 (2H, m), 2.76 (3H, s), 3.01 (2H, t, J=8 Hz), 3.97 (3H, s), 7.18 (1H, s), 7.28 (1H, t, J=8 Hz), 8.06 (1H, d, J=8 Hz), 8.15 (1H, d, J=8 Hz).

(6) Methyl 1-acetyl-2-(2-methoxycarbonylethyl)indole-6-carboxylate

NMR (CDCl$_3$, δ): 2.78 (2H, t, J=7 Hz), 2.67 (3H, s), 3.39 (2H, t, J=7 Hz), 3.68 (3H, s), 3.94 (3H, s), 6.49 (1H, s), 7.52 (1H, d, J=8 Hz), 7.93 (1H, d, J=8 Hz), 8.46 (1H, s).

(7) methyl 1-acetyl-2-propylindol-6-ylacetate mp: 85–87° C. IR (KBr): 1736, 1700, 1376, 1320, 1303 cm$^{-1}$; NMR (CDCl$_3$, δ): 1.04 (3H, t, J=7 Hz), 1.74 (2H, sextet, J=7 Hz), 2.75 (3H, s), 2.96 (2H, t, J=7 Hz), 3.70 (2H, s), 3.75 (3H, s), 6.40 (1H, s), 7.14 (1H, d, J=8 Hz), 7.43 (1H, d, J=8 Hz), 7.81 (1H, s); MASS (m/z): 274 (M$^+$+1), 74 (bp).

PREPARATION 26

To a solution of methyl 1-acetyl-2-(3-methoxycarbonylpropyl)indole-6-carboxylate (2.34 g) in methanol (20 ml) was added powdered potassium carbonate (1.04 g), and the mixture was stirred under reflux for 10 minutes. The resulting mixture was evaporated in vacuo and the residue was acidified with 1N hydrochloric acid and extracted with chloroform. The organic phase was washed with aqueous sodium bicarbonate and brine, dried over sodium sulfate and then evaporated in vacuo. The residue was triturated with ether to give methyl 2-(3-methoxycarbonylpropyl)indole-6-carboxylate (1.23 g) as solid.

NMR (CDCl$_3$, δ): 2.07 (2H, m), 2.42 (2H, t, J=7 Hz), 2.84 (2H, t, J=7 Hz), 3.68 (3H, s), 3.92 (3H, s), 6.31 (1H, s), 7.52 (1H, d, J=8 Hz), 7.78 (1H, d, J=8 Hz), 8.07 (1H, s), 8.39 (1H, br s).

PREPARATION 27

The following compounds described in (1) to (5) were prepared in a similar manner to that of Preparation 26.

(1) Methyl 2-propylindole-7-carboxylate

NMR (CDCl$_3$, δ): 1.02 (3H, t, J=7 Hz), 1.78 (2H, m), 2.78 (2H, t, J=7 Hz), 3.98 (3H, s), 6.28 (1H, m), 7.09 (1H, t, J=8 Hz), 7.72 (1H, d, J=8 Hz), 7.79 (1H, d, J=8 Hz), 9.58 (1H, br s).

(2) Methyl 2-propylindole-6-carboxylate (3) Methyl 2-propylindole-5-carboxylate

NMR (CDCl$_3$, δ): 1.02 (3H, t, J=8 Hz), 1.76 (2H, sextet, J=8 Hz), 2.74 (2H, t, J=8 Hz), 3.92 (3H, s), 6.33 (1H, d, J=1 Hz), 7.28 (1H, d, J=8 Hz), 7.73 (1H, d, J=8 Hz), 8.10 (1H, br s), 8.28 (1H, s).

(4) Methyl 2-propylindole-4-carboxylate

NMR (CDCl$_3$, δ): 1.03 (3H, t, J=7 Hz), 1.80 (2H, m), 2.78 (2H, m), 3.98 (3H, s), 6.89 (1H, s), 7.14 (1H, t, J=8 Hz), 7.48 (1H, d, J=8 Hz), 7.84 (1H, d, J=8 Hz), 8.08 (1H, br s).

(5) Methyl 2-2-methoxycarbonylethyl)indole-6-carboxylate

NMR (CDCl$_3$, δ): 2.78 (2H, m), 3.10 (2H, m), 3.73 (3H, s), 3.93 (3H, s), 6.30 (1H, s), 7.53 (1H, d, J=8 Hz), 7.76 (1H, d, J=8 Hz) 8.08 (1H, s) 8.88 (1H, br s).

PREPARATION 28

The following compounds described in (1) to (19) were prepared in a similar manner to that of Preparation 1 (5).

(1) Methyl 3-isobutyryl-2-propylindole-7-carboxylate

NMR (CDCl$_3$, δ): 1.04 (3H, t, J=7 Hz), 1.27 (6H, d, J=7 Hz), 1.82 (2H, m), 3.26 (2H, m), 3.47 (1H, m), 3.99 (3H, s), 7.28 (1H, t, J=8 Hz), 7.85 (1H, d, J=8 Hz), 8.18 (1H, s).

(2) Methyl 3-isobutyryl-2-propylindole-5-carboxylate

NMR (CDCl$_3$, δ): 1.04 (3H, t, J=8 Hz), 1.28 (6H, d, J=8 Hz), 1.78 (2H, sextet, J=8 Hz), 3.15 (2H, t, J=8 Hz), 3.56 (1H, septet, J=8 Hz), 3.96 (3H, s), 7.37 (1H, d, J=1 Hz), 7.93 (1H, dd, J=1, 8 Hz), 8.66 (1H, d, J=8 Hz), 8.75 (1H, br s).

(3) Methyl 3-(3-methoxycarbonylpronanoyl)indole-6-carboxylate

NMR (DMSO-d$_6$, δ): 2.65 (2H, t, J=7 Hz), 3.22 (2H, t, J=7 Hz), 3.59 (3H, s), 3.87 (3H, s), 7.80 (1H, d, J=7 Hz), 8.10 (1H, s), 8.23 (1H, d, J=8 Hz), 8.59 (1H, s).

(4) Methyl 3-acetyl-2-methylindole-6-carboxylate

NMR (CDCl$_3$, δ): 2.54 (3H, s), 2.73 (3H, s), 3.86 (3H, s), 7.76 (1H, d, J=8 Hz), 7.97 (1H, s), 8.12 (1H, d, J=8 Hz).

(5) Methyl 2-methyl-3-proponylindole-6-carboxylate

NMR (CDCl$_3$, δ): 1.12 (3H, t, J=7 Hz), 2.72 (3H, s), 2.92 (2H, q, J=7 Hz), 3.86 (3H, s), 7.75 (1H, d, J=8 Hz), 7.96 (1H, s), 8.11 (1H, d, J=8 Hz).

(6) Methyl 3-(3,3-dimethylbutanoyl)indole-6-carboxylate

NMR (CDCl$_3$, δ): 1.11 (9H, m), 2.33 (2H, s), 3.94 (3H, s), 7.92–8.0 (2H, m), 8.19 (1H, s), 8.52 (1H, d, J=8 Hz), 8.90 (1H, br s).

(7) Ethyl 3-isobutyryl-2-propylindol-6-ylacetate

IR (Neat): 3300, 1740, 1625 cm$^{-1}$; NMR (CDCl$_3$, δ): 1.04 (3H, t, J=7 Hz), 1.25 (6H, d, J=7 Hz), 1.26 (3H, t, J=7 Hz), 1.77 (2H, sextet, J=7 Hz), 3.12 (2H, t, J=7 Hz), 3.41–3.55 (1H, m), 3.72 (2H, s), 4.16 (2H, q, J=7 Hz), 7.17 (1H, d, J=7.5 Hz), 7.30 (1H, s), 7.82 (1H, d, J=7.5 Hz), 8.40 (1H, br s); MASS (m/z): 316 (M$^+$+1), 74 (bp).

(8) Methyl 3-isobutyryl-2-propylindol-6-ylacetate

IR (Neat): 3290, 1730, 1625 cm$^{-1}$; NMR (CDCl$_3$, δ): 1.03 (3H, t, J=7 Hz), 1.26 (6H, d, J=7 Hz), 1.76 (2H, sextet, J=7 Hz), 3.12 (2H, t, J=7 Hz), 3.41–3.54 (1H, m), 3.71 (2H, s), 3.75 (3H, s), 7.16 (1H, d, J=7.5 Hz), 7.30 (1H, s), 7.83 (1H, d, J=7.5 Hz), 8.40 (1H, br s); MASS (m/z): 302 (M$^+$+1, bp).

(9) Methyl 2-acetyl-3-methylindole-6-carboxylate

NMR (CDCl$_3$, δ): 2.66 (3H, s), 2.67 (3H, s), 3.94 (3H, s), 7.72 (1H, d, J=8 Hz), 7.81 (1H, d, J=8 Hz), 8.11 (1H, S) 9.09 (1H, br s).

(10) Methyl 3-propionylindole-6-carboxylate

NMR (CDCl$_3$, δ): 1.12 (3H, t, J=7 Hz), 2.89 (2H, q, J=7 Hz), 3.87 (3H, s), 7.79 (1H, d, J=8 Hz), 8.11 (1H, s), 8.28 (1H, d, J=8 Hz), 8.53 (1H, s).

(11) Methyl 2-propionyl-3-propylindole-6-carboxylate

NMR (CDCl$_3$, δ): 1.06 (3H, t, J=7 Hz), 1.29 (3H, t, J=7 Hz), 1.74 (2H, m), 2.95–3.13 (4H, m), 3.94 (3H, s), 7.72 (1H, d, J=8 Hz), 7.79 (1H, d, J=8 Hz), 8.12 (1H, s), 9.11 (1H, br s).

(12) Methyl 2-isobutyryl-3-propylindole-6-carboxylate

NMR (CDCl$_3$, δ): 1.04 (3H, t, J=7 Hz), 1.29 (6H, t, J=7 Hz), 1.76 (2H, m), 3.09 (2H, m), 3.44 (1H, m), 3.94 (3H, s), 7.71 (1H, d, J=8 Hz), 7.79 (1H, d, t, =8 Hz), 8.12 (1H, s), 9.12 (1H, br s).

(13) Methyl 3-cyclopropanecarbonyl-2-propylindole-6-carboxylate mp: 152.5–154° C.; IR (KBr): 3371, 1687, 1623, 1458 cm$^{-1}$;

NMR (CDCl$_3$, δ): 1.00–1.09 (2H, m), 1.02 (3H, t, J=7 Hz), 1.28–1.32 (2H, m), 1.82 (2H, sextet, J=7 Hz), 2.56–2.65 (1H, m), 3.15 (2H, t, J=7 Hz), 3.96 (3H, s), 8.00 (2H, AB, J=8, 8 Hz), 8.15 (1H, s), 8.89 (1H, br s); MASS (m/z): 286 (M$^+$+1, bp).

(14) Methyl 3-cyclobutanecarbonyl-2-propylindole-6-carboxylate mp: 159–160° C.; IR (KBr): 1692, 1645, 1623 cm$^{-1}$;

NMR (CDCl$_3$, δ): 1.06 (3H, t, J=7 Hz), 1.83 (2H, sextet, J=7 Hz), 1.93–2.13 (2H, m), 2.30–2.51 (4H, m), 3.20 (2H, t, J=7 Hz), 3.95 (3H, s), 3.99 (1H, quintet, J=7 Hz), 7.93 (2H, s), 8.15 (1H, s), 9.08 (1H, br s); MASS (m/z): 300 (M$^+$+1), 74 (bp).

(15) Methyl 3-cylcopentanecarbonyl-2-propylindole-6-carboxylate mp: 137–139° C.; IR (KBr): 1692, 1647, 1624 cm$^{-1}$; (CDCl$_3$, δ): 1.02 (3H, t, J=7 Hz), 1.64–1.82 (6H, m), 1.94–2.05 (4H, m), 3.17 (2H, t, J=7 Hz), 3.72 (1H, quintet, J=7 Hz), 3.95 (3H, 5), 7. 93 (2H, ABX, J=8, 8, 1 Hz), 8.15 (1H, d, J=1 Hz), 9.19 (1H, s); MASS (m/z): 314 (M$^+$+1, bp).

(16) Methyl 3-cyclohexanecarbonyl-2-propylindole-6-carboxylate mp: 136–137° C.; IR (KBr): 1691, 1651, 1487, 1435 cm$^{-1}$;

NMR (CDCl$_3$, δ): 1.03 (3H, t, J=7 Hz), 1.25–2.04 (12H, n), 3.14–3.25 (1H, m), 3.18 (2H, t, J=7 Hz), 3.97 (3H, s), 7.90 (2H, q, J=7.5 Hz), 8.17 (1H, s), 9.16 (1H, br s); MASS (m/z): 328 (M$^+$+1), 74 (bp);

(17) Methyl 3-(3-methyl-2-butenoyl)-2-propylindole-6-carboxylate mp: 146–147° C.; IR (KBr): 1715, 1464, 1433, 1220 cm$^{-1}$; NMR (CDCl$_3$, δ): 1.05 (3H, t, J=7 Hz), 1.82 (2H, sextet, J=7 Hz), 2.05 (3H, s), 2.20 (3H, s), 3.18 (2H, t, J=7 Hz), 3.94 (3H, s), 6.63 (1H, s), 7.95 (2H, AB, J=7.5, 7.5 Hz), 8.11 (1H, s), 8.88 (1H, br s); MASS (m/z): 300 (M$^+$+1), 74 (bp).

(18) Methyl 3-crotonoyl-2-propylindole-6-carboxylate mp: 153–154° C.; IR (KBr): 1715, 1650, 1583, 1567, 1459, 1432 cm$^{-1}$; NMR (CDCl$_3$, δ): 1.05 (3H, t, J=7 Hz), 1.83 (2H, sextet, J=7 Hz), 2.04 (3H, t, J=7, 1 Hz), 3.15 (2H, t, J=7 Hz), 3.96 (3H, s), 6.89 (1H, dd, J=15, 1 Hz), 7.04 (1H, dd, J=15, 7 Hz), 7.94 (2H, dq, J=7, 1 Hz), 8.12 (1H, s), 8.99 (1H, br s); MASS (m/z): 286 (M$^+$+1).

(19) 3-Acetyl-6-chloroindole

NMR (CDCl$_3$, δ): 2.44 (3H, s), 7.19 (1H, d, J=8 Hz), 7.51 (1H, s), 8.14 (1H, d, J=8 Hz), 8.35 (1H, s).

PREPARATION 29

The following compounds described in (1) to (3) were prepared in a similar manner to that of Preparation 6 (2).

(1) Methyl 3-(3-methoxycarbonylpropyl)indole-6-carboxylate

NMR (CDCl$_3$, δ): 2.04 (2H, m), 2.37 (2H, t, J=7 Hz), 2.81 (2H, t, J=7 Hz), 3.64 (3H, s), 3.93 (3H, s), 7.16 (H, s), 7.61 (1H, d, J=8 Hz), 7.79 (1H, d, J=8Hz), 8.10 (1H, s), 8.22 (1H, br s).

(2) Methyl 3-methylindole-6-carboxylate

NMR (CDCl$_3$, δ): 2.33 (3H, s), 3.93 (3H, s), 7.12 (1H, s), 7.59 (1H, d, J=8 Hz), 7.80 (1H, d, J=8 Hz), 8.09 (1H, S), 8. 10 (1H, br s).

(3) Methyl 3-propylindole-6-carboxylate

NMR (CDCl$_3$, δ): 1.00 (3H, t, J=7 Hz), 1.74 (2H, m), 2.73 (2H, t, J=7 Hz), 3.93 (3H, S), 7.14 (1H, d, J=1 Hz), 7.60 (1H, d, J=8 Hz), 7.73 (1H, d, J=8 Hz), 8.10 (1H, s)) 8.18 (1H, br s).

PREPARATION 30

To a solution of methyl 3-(3-methoxycarbonylpropyl)-indole-6-carboxylate (656 mg) in methanol (24 ml) was added 1N aqueous sodium hydroxide (2.46 ml), and the mixture was stirred at 20° C. for 2 days. The resulting mixture was evaporated in vacuo, and the residue was acidified with 1N hydrochloric acid (2.6 ml) and extracted with ethyl acetate. The organic chase was washed with brine, dried over sodium sulfate and evaporated in vacuo. The residue was triturated with ether to give methyl 3-(3-carboxypropyl)indole-6-carboxylate (486 mg) as solid.

NMR (CDCl$_3$, δ): 2.03 (2H, m), 2.37 (2H, m), 2.80 (2H, m), 3.93 (3H, s), 7.17 (1H, s), 7.59 (1H, d, J=8 Hz), 7.74 (1H, , J=8 Hz), 8.09 (1H, s).

PREPARATION 31

A mixture or methyl 3-(3-carboxypropyl)indole-6-carboxylate (173 mg), triphenylphosphine (191 mg) and carbon tetrachloride (1.0 ml) in 1,2-dichloroethane (10 ml) was heated at 80° C. for 2 hours. The resulting mixture was diluted with chloroform and washed with water, aqueous sodium bicarbonate and brine. The organic phase was dried over sodium sulfate and evaporated in vacuo. The residue was purified by silica gel thin layer chromatography with a mixture of hexane and ethyl acetate (4:1) and recrystallized from a mixture of hexane and ethyl acetate to give methyl 8-oxo-5,6,7,8-tetrahydrocarbazole-2-carboxylate (72.2 mg) as colorless crystals.

NMR (CDCl$_3$, δ): 2.29 (2H, m), 2.69 (2H, t, J=7 Hz), 3.03 (2H, t, J=7 Hz), 3.94 (3H, s), 7.69 (1H, d, J=8 Hz), 7.82 (1H, d, J=8 Hz), 8.16 (1H, s), 8.95 (1H, br s).

PREPARATION 32

To a stirred mixture of methyl (E)-4-[2-(dimethylamino) vinyl]-3-nitrobenzoate (500 mg), which was prepared by the method of Brown et al. described in Journal of Medicinal Chemistry, vol. 35, page 2419 (1992), and pyridine (0.16 ml) in tetrahydrofuran (3 ml) was added butyryl chloride (0.21 ml) at 20° C. The reaction mixture was stirred at 40° C. for 24 hours and 50° C. for 4 hours. After cooled to 20° C., the reaction mixture was diluted with water and extracted with ethyl acetate. The organic phase was washed with water and brine, dried over magnesium sulfate and evaporated in vacuo. The residue was chromatographed on silica gel eluting with a mixture of ethyl acetate and hexane (1:1) to give methyl 4-(1-dimethylaminomethylene-2-oxopentyl)-3-nitrobenzoate (426 mg) as colorless amorphous.

NMR (CDCl$_3$, δ): 0.89 (3H, t, J=7 Hz), 1.52–1.65 (2H, m), 2.30 (2H, t, J=7 Hz), 2.78 (6H, s), 3.99 (3H, s), 7.34 (1H, d, J=7.5 Hz), 7.56 (1H, s), 8.18 (1H, dd, J=7.5, 1Hz), 8.51 (1H, d, J=1 Hz); MASS (m/z): 321 (M$^+$+1).

PREPARATION 33

A solution of methyl 4-(1-dimethylaminomethylene-2-oxopentyl)-3-nitrobenzoate (172 mg) in dioxane (9 ml) was refluxed For 4 days. The resulting mixture was evaporated in vacuo, and the residue was purified by thin layer chromatography with a mixture of hexane and ethyl acetate (2:1) to give methyl 3-nitro-4-(2-oxopentyl)benzoate (127 mg).

NMR (CDCl$_3$, δ): 0.97 (3H, t, J=7 Hz), 1.69 (2H, m), 2.60 (2H, t, J=7 Hz), 3.95 (3H, s), 4.16 (2H, s), 7.36 (1H, d, J=8 Hz), 8.22 (1H d, J=8 Hz), 8.73 (1H, s).

PREPARATION 34

To a solution of methyl 3-nitro-4-(2-oxopentyl)benzoate (114 mg) in a mixture of tetrahydrofuran (1.5 ml), ethanol (1.5 ml) and water (2.1 ml) was added sodium hydrosulfite (3.0 g), and the mixture was stirred under reflux for 30 minutes. The resulting mixture was evaporated in vacuo, and the residue was diluted with ethyl acetate. The organic phase was washed with water and brine, dried over sodium sulfate and evaporated in vacuo. The residue was purified by thin layer chromatography with a mixture of hexane and ethyl acetate (2:1) to give methyl 2-propylindole-6-carboxylate (54.6 mg).

PREPARATION 35

To a stirred solution of 3-isobutyryl-2-propylindole-6-carboxylic acid (331 mg) in tetrahydrofuran (5 ml) were added benzylalcohol (1.25 ml), dicyclohexylcarbodiimide (303 mg) and 4-dimethylaminopyridine (20 mg) at 20° C. The reaction mixture was stirred at 20° C. for 8 hours. The precipitated urea was filtered off and the filtrate was evaporated in vacuo. The residue was extracted with ethyl acetate and the extract was washed with water two times and brine. The organic phase was dried over sodium sulfate and evaporated in vacuo. The residue was chromatographed on silica gel eluting with a mixture of ethyl acetate and hexane (1:4) to give the crystals which were recrystallized from a mixture of ethyl acetate and hexane to give benzyl 3-isobutyryl-2-propylindole-6-carboxylate (215 mg) as colorless crystals.

mp: 102–104° C.; IR (KBr): 1700, 1655 cm$^{-1}$; NMR (CDCl$_3$, δ): 1.05 (3H, t, J=7 Hz), 1.28 (6H, t, J=7 Hz), 1.73–1.87 (2H, m), 3.17 (2H, t, J=7 Hz), 3.45–3.53 (1H, m), 5.40 (2H, s), 7.32–7.50 (5H, m), 7.95 (2H, AB, J=9, 8 Hz), 8.14 (1H, s), 8.59 (1H, br s); MASS m/z): 364 (M$^+$+1), 76 (bp).

PREPARATION 36

The following compound was prepared in a similar manner to that of Example 32.

Methyl 3-formylindole-6-carboxylate

NMR (CDCl$_3$, δ): 3.88 (3H, s), 7.83 (1H, dd, J=1, 8 Hz), 8.12 (1H, s), 8.16 (1H, d, J=8 Hz), 8.49 (1H, s), 12.45 (1H, br s).

PREPARATION 37

To a solution of methyl 3-isobutyryl-2-propylindole-6-carboxylate (201 mg) in carbon tetrachloride (7 ml) was added N-bromosuccinimide (187 mg) and 2,2'-azobis (4-methoxy-2,4-dimethylvaleronitrile; (20 mg) and refluxed for 30 minutes. The resulting mixture was filtered and the filtrate was evaporated in vacuo. The residue was purified by preparative thin layer chromatography on silica gel eluting with a mixture of hexane and ethyl acetate (2:1) to give methyl 2-(1-bromopropyl)-3-isobutyrylindole-6-carboxylate (179 mg).

This compound was used immediately without purification.

PREPARATION 38

To a solution of methyl 2-(1-bromopropyl)-3-isobutyrylindole-6-carboxylate (179 mg) in 1,2-dichloroethane (8 ml) was added N,N-diisopropylethylamine (0.24 ml) and refluxed for 40 minutes. The resulting mixture was evaporated in vacuo, then the residue was diluted with ethyl acetate and washed with diluted hydrochloric acid, water and brine. The organic phase was dried over sodium sulfate and evaporated in vacuo. Trituration with diethyl ether gave methyl 3-isobutyryl-2-(1-propenyl)indole-6-carboxylate (55.2 mg).

NMR (CDCl$_3$, δ): 1.27 (6H, d, J=7 Hz), 2.01 (3H, d, J=7 Hz), 3.47 (1H, m), 3.93 (3H, s), 6.44 (1H, m), 7.32 (1H, d, J=16 Hz), 7.59 (1H, d, J=8 Hz), 7.94 (1H, d, J=8 Hz), 8.11 (1H, s), 8.94 (1H, br s).

PREPARATION 39

To a solution of methyl 2-(1-bromopropyl)-3-isobutyrylindole-6-carboxylate (323 mg) in acetic acid (3 ml) was added potassium acetate (345 mg) and the mixture was stirred at 6° C. for 2 hours. The resulting mixture was evaporated in vacuo, then he residue was diluted with ethyl acetate and washed with water, aqueous sodium bicarbonate and brine. The organic phase was dried over sodium sulfate and evaporated in vacuo. The residue was purified by preparative thin layer chromatography on silica gel eluting with a mixture of hexane and ethyl acetate (2:1) to give methyl 2-(1-acetoxypropyl)-3-isobutyrylindole-6-carboxylate (207 mg).

NMR (CDCl$_3$, δ): 0.99 (3H, t, J=7 Hz), 1.23 (3H, d, J=7 Hz), 1.29 (3H, d, J=7 Hz), 1.94 (1H, m), 2.08 (1H, m), 2.18 (3H, s), 3.52 (1H, m), 3.94 (3H, s), 6.6 (1H, m), 7.88 (1H, d, J=8 Hz), 7.94 (1H, d, J=8 Hz), 8.18 (1H, s) 9.09 (1H, br s).

PREPARATION 40

To a mixture of methyl 2-propylindole-6-carboxylate (10 g), methoxyacetic acid (4.6 ml) and carbontetrachloride (13.4 ml) in 1,2-dichloroethane (45 ml) was added slowly triphenylphosphine (16.7 g) in 1,2-dichloroethane (30 ml) over 1 hour under reflux, and the resulting mixture was heated under reflux for additional 8 hours. After evaporation of solvent, the residue was chromatographed on silica gel eluting with a mixture of hexane and ethyl acetate (1:1) and triturated with diethyl ether to give methyl 3-methoxyacetyl-2-propylindole-6-carboxylate (8.11 g).

PREPARATION 41

The following compound was prepared in a similar manner to that of Preparation 15 (1).

Methyl 3-ethoxyacetyl-2-propylindole-6-carboxylate

NMR (CDCl$_3$, δ): 1.05 (3H, t, J=7 Hz), 1.32 (3H, t, J=7 Hz), 1.84 (2H, sextet, J=8 Hz), 3.22 (2H, t, J=7 Hz), 3.74 (3H, q, J=7 Hz), 3.97 (3H, s), 4.75 (2H, s), 7.83 (1H, d, J=8 Hz), 7.94 (1H, d, J=8 Hz), 8.15 (1H, s), 9.27 (1H, br s).

PREPARATION 42

To a stirred mixture of methyl 4-hydroxyphenylacetate (10.0 g) in acetic acid (55 ml) was added nitric acid (22.1 ml) at 0° C. The reaction mixture was stirred at 0° C. for 2 hours. After warmed to 20° C., the reaction mixture was diluted with water (200 ml) and precipitated crystals were collected. The crystals were dissolved in chloroform, and the solution was washed with water, dried over magnesium sulfate and evaporated in vacuo. The residue was recrystallized from a mixture of chloroform and hexane to give methyl 4-hydroxy-3-nitrophenylacetate (9.3 g) as yellow crystals.

mp: 64–69° C.; IR (KBr): 1734, 1540, 1534, 1263, 1170 cm$^{-1}$; NMR (CDCl$_3$, δ): 3.64 (2H, 5), 3.73 (3H, s), 7.14 (1H, d, J=8 Hz), 7.52 (1H, dd, J=8, 1 Hz), 8.02 (1H, d, J=1 Hz); MASS (m/z): 210 (M$^+$–1).

PREPARATION 43

Iron powder (2.5 g) was added to a stirred mixture of methyl 3-nitro-4-trifluoromethanesulfonyloxyphenylacetate (2.97 g) and conc. hydrochloric acid (7.3 ml) in methanol (22 ml) at 0° C. in some small portion. The reaction mixture was stirred at 20° C. for 2 hours, then poured into a mixture of ethyl acetate and saturated sodium bicarbonate. The organic chase was washed with saturated sodium bicarbonate and brine, dried over sodium sulfate and evaporated in vacuo. The residue was chromatographed on silica gel eluting with a mixture of ethyl acetate and hexane (1:4 to give methyl 3-amino-4-trifluoromethanesulfonyloxyphenylacetate 2.34 g) as colorless crystals.

mp: 66–69° C.; NMR (CDCl$_3$, δ): 3.57 (2H, s) 3.71 (3H, s, 3.94 (2H, s), 6.67 (1H, dd, J=7.5, 1 Hz), 6.79 (1H, d, J=1 Hz), 7.11 (1H, dd, J=7.5 Hz).

PREPARATION 44

The following compounds were prepared from methyl 1-acetyl-2-propylindol-6-ylacetate in a similar manner to that of Preparation 26.

Methyl 2propylindol-6-ylacetate

IR (Neat) 3400, 1740 cm$^{-1}$; NMR (CDCl$_3$, δ): 1.00 (3H, t, J=7 Hz), 1.75 (2H, sextet, J=7 Hz), 2.72 (2H, t, J=7 Hz), 3.70 (3H, s), 3.72 (2H, s), 6.22 (1H, s), 6.99 (1H, d, J=7.5 Hz), 7.22 (1H, s), 7.47 (1H, d, J=7.5 Hz), 7.83 (1H, br s); MASS (m/z): 232 (M$^+$+1), 74 (bp).

Ethyl 2-propylindol-6-ylacetate

IR (Neat) 3400, 1735 cm$^{-1}$; NMR (CDCl$_3$, δ): 1.00 (3H, t, J=7 Hz), 1.05 (3H, t, J=7 Hz), 1.74 (2H, sextet, J=7 Hz), 2.72 (2H, t, J=7 Hz), 3.69 (3H, s), 4.13 (2H, q, J=7 Hz), 6.20 (1H, s), 6.99 (1H, d, J=7.5 Hz), 7.23 (1H, s), 7.46 (1H, d, J=7.5 Hz), 7.83 (1H, br s); MASS (m/z): 346 (M$^+$-1), 74 (bp).

2-propylindol-6-ylacetic acid mp: 85–87° C.; IR (KBr): 3381, 1701, 1691 cm$^{-1}$; NMR (CDCl$_3$, δ): 1.00 (3H, t,=7 Hz), 1.73 (2H, sextet, J=7 Hz), 2.72 (2H, t, J=7 Hz), 3.73 (2H, s), 6.21 (1H, s), 6.98 (1H, d, J=7.5 Hz), 7.21 (1H, s), 7.48 (1H, d, J=7.5 Hz), 7.83 (1H, br s); MASS (m/z): 216 1(M$^+$-1, bp).

PREPARATION 45

To a stirred solution of methyl 3-ethylindole-6-carboxylate (138 mg) in dichloromethane (5 ml) was added sulfuryl chloride (0.066 ml), and the mixture was stirred at 20° C. for 1 hour. The resulting mixture was poured into ice and extracted with ethyl acetate. The combined organic phase was washed with aqueous sodium bicarbonate and brine, then dried over sodium sulfate and evaporated in vacuo. The residue was chromatographed on silica gel eluting with a mixture of hexane and ethyl acetate (4:1) to give methyl 2-chloro-3-ethylindole-6-carboxylate (58.2 mg) as a solid.

NMR (CDCl$_3$, δ): 1.26 (3H, t, J=7 Hz), 2.76 (2H, q, J=7 Hz), 3.92 (3H, s), 7.54 (1H, d, J8 Hz), 7.82 (1H, d, J=8 Hz) 8.02 (1H, s), 8.19 (1H, br s).

PREPARATION 46

To a stirred solution of methyl 3-formylindole-6-carboxylate (368 mg) in 1,4-dioxane (10 ml) was added acetylmethylene triphenylphosphorane (1.15 g), and the mixture was stirred under reflux for 14 hours. The resulting mixture was evaporated in vacuo, redissolved with ethyl acetate and washed with 1N hydrochloric acid and brine. The organic phase was dried over sodium sulfate and evaporated in vacuo. The residue was chromatographed on silica gel eluting with a mixture of chloroform and ethyl acetate (1:2) to give methyl 3-(3-oxo-1-butenyl)indole-6-carboxylate (75 mg) as a solid.

NMR (CDCl$_3$, δ): 2.39 (3H, s), 3.95 (3H, s), 6.79 (1H, d, J=15 Hz), 7.71 (1H, s), 7.80 (1H, d, J=8 Hz), 7.87–7.96 (2H, m), 8.14 (1H, s).

PREPARATION 47

The following compound was prepared from in a similar manner to that of Preparation 46.

Methyl 3-(2-methoxycarbonylethenyl)indole-6-carboxylate

NMR (DMSO-d$_6$, δ): 3.72 (3H, s), 4.87 (3H, s), 6.44 (1H, d, J=15 Hz), 7.76 (1H, d, J=8 Hz), 7.89 (1H, d, J=15 Hz), 7.98 (1H, d, J=8 Hz), 8.10 (1H, s), 8.20 (1H, s).

PREPARATION 48

To a solution of methyl 3-(2-methoxycarbonylethenyl)-indole-6-carboxylate (213 mg) in a mixture of 1,4-dioxane (2 ml) and methanol (3 ml) was added 10% palladium on carbon (40 mg) and the mixture was stirred under hydrogen at 20° C. for 6.5 hours. The resulting mixture was filtered through celite and the filtrate was evaporated in vacuo. The residue was triturated with diisopropyl ether to give methyl 3-(2-methoxycarbonylethyl)indole-6-carboxylate (177 mg).

NMR (CDCl$_3$, δ): 2.72 (2H, t, J=7 Hz), 3.12 (2H, t, J=7 Hz), 3.68 (3H, s), 3.94 (3H, s), 7.20 (1H, d, J=2 Hz), 7.62 (1H, d, J=8 Hz), 7.82 (1H, d, J=8 Hz), 8.12 (1H, s), 8.21 (1H, br s).

PREPARATION 49

The following compound was prepared from a similar manner to that of Preparation 30.

3-(6-Methoxycarbonylindol-3-yl)propionic acid

NMR (CDCl$_3$, δ): 2.72 (2H, t, J=7 Hz), 3.10 (2H, t, J=7 Hz), 3.94 (3H, s), 7.19 (1H, s) 7.60 (1H, d, J=8 Hz), 7.77 (1H, d, J=8 Hz), 8.10 (1H, s).

PREPARATION 50

The following compound was prepared in a similar manner to that of Preparation 31.

Methyl 3-oxo-1,2,3,4-tetrahydrocyclopent[b]indole-6-carboxylate

NMR (CDCl$_3$, δ): 3.05 (2H, m), 3.14 (2H, m), 3.97 (3H, s), 7.76 (1H, d, J=8 Hz), 7.85 (1H, d, J=8 Hz), 8.21 (1H, s).

PREPARATION 51

The following compounds described in (1) to (6) were prepared in a similar manner to that of Preparation 8 (1).

(1) 3-Cyclopropanecarbonyl-2-propylindole-6-carboxylic acid mp: 250.5–251.5° C. (dec.); IR. (KBr): 1685, 1600, 1463, 1424, 1300 cm$^{-1}$; NMR (CDCl$_3$–CD$_3$OD, δ): 1.00–1.09 (2H, m), 1.02 (3H, t, J=7 Hz), 1.25–1.29 (2H, m), 1.81 (2H, sextet, J=7 Hz), 2.59–2.69 (1H, m), 3.12 (2H, t, J=7 Hz), 7.99 (2H, AB, J=7.5, 7.5 Hz), 8.09 (1H, s); MASS (m/z): 270 (M$^+$-1).

(2) 3-Cyclobutanecarbonyl-2-propylindole-6-carboxylic acid mp: 244–245° C.; IR (KBr): 1688, 1419, 1292 cm$^{-1}$; NMR (CDCl$_3$–CD$_3$OD, δ): 1.05 (3H, t, J=7 Hz), 1.80 (2H, sextet, J=7 Hz), 1.92–2.15 (2H, m), 2.29–2.49 (2H, m), 4.01 (1H, quintet, J=7 Hz), 7.90 (2H, s), 8.08 (1H, s); MASS (m/z): 286 (M$^+$+1), 74 (bp).

(3) 3-Cylcopentanecarbonyl-2-propylindole-6-carboxylic acid mp: 233–235° C.; IR (KBr): 1673, 1611, 1463, 1453 cm$^{-1}$;

NMR (CDCl$_3$–CD$_3$OD, δ): 0.99 (3H, t, J=7 Hz), 1.51–1.79 (6H, m), 1.89–1.97 (4H, m), 3.10 (2H, t, J=7 Hz), 3.70 (1H, quintet, J=7 Hz), 7.85–7.94 (2H, m), 8.05 (1H, s); MASS (m/z): 298 (M$^+$-1, bp).

(4) 3-Cyclohexanecarbonyl-2-propylindole-6-carboxylic acid mp: 217–218° C.; IR (KBr): 1675, 1614, 1457 cm$^{-1}$;

NMR (CDCl$_3$–CD$_3$OD, δ): 0,99 (3H, t, J=7 Hz), 1.19–1.56 (6H, m), 1.74 (2H, sextet, J=7 Hz), 1.80–1.95 (4H, m), 3.08 (2H, t, J=7 Hz), 3.09–3.20 (1H, m), 7.80 (1H, d, J=8 Hz), 7.88 (1H, dd, J=8, 1 Hz), 8.03 (1H, d, J=1 Hz); MASS (m/z): 312 (M$^+$−1, bp).

(5) 3-(3-methyl-2-butenoyl)-2-propylindole-6-carboxylic acid mp: 246–248° C. (dec.); IR (KBr): 1669, 1465, 1423 cm$^{-1}$;

NMR (DMSO-d$_6$, δ): 0.97 (3H, t, J=7 Hz), 1.75 (2H, sextet, J=7 Hz), 2.00 (3H, s), 2.09 (3H, s), 3.08 (2H, t, J=7 Hz), 6.60 (1H, s), 7.73 (1H, d, J=7.5 Hz), 7.95 (1H, d, J=7.5 Hz), 7.99 (1H, s); MASS (m/z): 284 (M$^+$−1, bp), 82 (bp).

PREPARATION 52

The following compounds described in (1) to (6) were prepared in the similar manner to that of Example 6.

(1) 3-Cyclopropanecarbonyl-2-propylindole-6-carboxamide mp: 120–122° C.; IR (KBr): 1670, 1623, 1598, 1394 cm$^{-1}$;

NMR (DMSO-d$_6$, δ): 0.94 (3H, t, J=7 Hz), 0.99–1.04 (4H, m), 1.73 (2H, sextet, J=7 Hz), 2.55–2.62 (1H, m), 3.07 (2H, t, J=7 Hz), 7.22 (1H, br s), 7.69 (1H, dd, J=7.5, 1 Hz), 7.93 (1H, d, J=1 Hz), 7.96 (1H, br s), 8.00 (1H, d, J=7.5 Hz); MASS (m/z): 269 (M$^+$−1), 98 (bp).

(2) 3-Cyclobutanecarbonyl-2-propylindole-6-carboxamide mp: 253–255° C.; IR (KBr): 1675, 1624, 1605, 1456, 1397 cm$^{-1}$; NMR (DMSO-d$_6$, δ): 0.97 (3H, t, J=7 Hz), 1.66–1.89 (3H, m), 1.97–2.09 (1H, m), 2.23–2.30 (4H, m), 3.09 (2H, t, J=7 Hz), 3.99 (1H, quintet, J=7 Hz), 7.24 (1H, br s), 7.69 (1H, d, J=7.5 Hz), 7.86 (1H, d, J=7.5 Hz), 7.90 (1H, s), 7.97 (1H, br s); MASS (m/z): 295 (M$^+$+1), 85 (bp).

(3) 2-Cyclopentanecarbonyl-2-propylindole-6-carboxamide mp: 213–255° C. IR (KBr): 1666, 1628, 1623, 1604 cm$^{-1}$;

NMR (CDCl$_3$–CD$_3$OD, δ): 1.01 (3H, t, J=7 Hz), 1.61–1.83 (6H, m) 1.90–1.98 (4H, m), 3.13 (2H, t, J=7 Hz), 3.69 (1H, quintet, J=7 Hz), 7.52 (1H, dd, J=8, 1 Hz), 7.91 (1H, d, J=1 Hz), 7.96 (1H, d, J=8 Hz); MASS (m/z): 299 (M$^+$+1), 74 (bp).

(4) 3-Cyclohexanecarbonyl-2-propylindole-6-carboxamide mp: 245–247° C.; IR (KBr): 1663, 1627, 1595, 1459, 1402 cm$^{-1}$; NMR (DSMO-d$_6$, δ): 0.95 (3H, t, J=7 Hz), 1.16–1.30 (1H, m), 1.35–1.46 (4H, m), 1.70 (2H, sextet, J=7 Hz), 1.75–1.88 (5H, m), 3.05 (2H, t, J=7 Hz), 3.10–3.17 (1H, m), 7.25 (1H, br s), 7.70 (1H, dd, J=7.5, 1 Hz), 7.81 (1H, d, J=7.5 Hz), 7.93 (1H, d, J=1 Hz), 7.95 (1H, br s); MASS (m/z): 313 (M$^+$+1), 85 (bp).

(5) 3-(3-Methyl-2-butenoyl)-2-propylindole-6-carboxamide mp 179–181° C.; IR (KBr): 1669, 1648, 1591, 1458, 1394 cm$^{-1}$; NMR (DMSO-d$_6$, δ): 0.95 (3H, t, J=7 Hz), 1.72 (2H, sextet, J=7 Hz), 1.99 (3H, s), 2.05 (3H, s), 3.05 (1H, t, J=7 Hz), 6.59 (1H, s), 7.22 (1H, br s), 7.67 (1H, d, J=7.5 Hz), 7.88 (1H, d, J=7.5 Hz), 7.90 (1H, s), 7.92 (1H, br s); MASS (m/z): 285 (M$^+$+1), 85 (bp).

(6) 3-(3-Methoxybutanoyl)-2-propylindole-6-carboxamide mp: 140–144° C.; IR (KBr): 1644, 1623, 1604, 1460, 1394 cm$^{-1}$; NMR (CDCl$_3$, δ): 1.02 (3H, t, J=7 Hz), 1.30 (3H, d, J=7 Hz), 1.80 (2H, sextet, J=7 Hz), 2.98 (1H, dd, J=15, 7 Hz), 3.17 (2H, t, J=7 Hz), 3.39 (1H, dd, J=15, 7 Hz), 3.40 (3H, s), 7.10 (1H, sextet, J=7 Hz), 7.55 (1H, dd, J=8, 1 Hz), 8.02 (1H, d, J=8 Hz), 8.10 (1H, d, J=1 Hz), 9.60 (1H, br s); MASS (m/z): 303 (M$^+$+1), 74 (bp).

PREPARATION 53

The following compound was prepared from methyl 3-crotonyl-2-propylindole-6-carboxylate in a similar manner to that of Preparation 8 (1).

3-(3-Methoxybutanoyl)-2-propylindole-6-carboxylic acid mp: 286–288° C. (dec.); IR (KBr): 3288, 1685, 1645, 1620 cm$^{-1}$; NMR (DMSO-d$_6$, δ): 0.96 (3H, t, J=7 Hz), 1.19 (3H, d, J=7 Hz), 1.73 (2H, sextet, J=7 Hz), 2.90 (1H, dd, J=15, 7 Hz), 3.08 (2H, t, J=7 Hz), 3.13 (3H, s), 3.15 (1H, dd, J=15, 7 Hz), 3.91 (1H, sextet, J=7 Hz), 7.26 (1H, d, J=8 Hz), 7.99 (1H, s), 8.00 (1H, d, J=8 Hz); MASS (m/z): 302 (M$^+$−1), 98 (bp).

EXAMPLE 1

To a solution of methyl 3-acetyl-2-propylindole-6-carboxylate (74 mg) in dimethylformamide (1.4 m ) was added sodium hydride (60%, 15.4 mg). The mixture was stirred at 20° C. for 30 minutes, then 2-chlorobenzyl bromide (0.045 ml) was added. After stirred for 1 hour, the mixture was diluted with ethyl acetate and washed with water and brine. The organic chase was dried over sodium sulfate and evaporated in vacuo to give methyl 3-acetyl-1-(2-chlorobenzyl)-2-propylindole-6-carboxylate (125 mg) as solid.

NMR (CDCl$_3$, δ): 1.01 (3H, t, J=7 Hz), 1.63 (2H, m), 2.74 (3H, s), 3.05 (2H, m), 3.89 (3H, s), 5.49 (2H, s), 6.22 (1H, d, J=8 Hz), 7.03 (1H, t, J=8 Hz), 7.20 (1H, t, J=8 Hz) 7.46 (1H, d, J=8 Hz), 7.93 (1H, s), 7.97 (1H, d, J=8 Hz), 8.04 (1H, d, J=8 Hz).

EXAMPLE 2

To a solution of methyl 3-acetyl-1-(2-chlorobenzyl)-2-propylindole-6-carboxylate (125 mg) in ethanol (6 ml) was added 1N aqueous sodium hydroxide (0.7 ml), and the mixture was stirred under reflux for 1 hour. The resulting mixture was evaporated in vacuo, and the residue was acidified with 1N hydrochloric acid (0.75 ml) and extracted with ethyl acetate. The extract was washed with brine, dried over sodium sulfate and evaporated in vacuo. The residue was triturated with isopropyl ether to give 3-acetyl-1-(2-chlorobenzyl)-2-propylindole-6-carboxylic acid (78 mg) as solid.

NMR (CDCl$_3$, δ): 1.02 (3H, t, J=7 Hz), 1.61 (2H, m), 2.76 (3H, s), 3.08 (2H, m), 5.52 (2H, s), 6.24 (1H, d, J=8 Hz), 7.04 (1H, t, J=8 Hz), 7.22 (1H, t, J=8 Hz), 7.46 (1H, d, J=8 Hz), 7.99 (1H, s), 8.03 (1H, d, J=8 Hz), 8.08 (1H, d, J=8 Hz);

EXAMPLE 3

To a solution of 3-acetyl-1-(2-chlorobenzyl)-2-propylindole-6-carboxylic acid (74 mg) in dimethylformamide (2 ml) were added 1-hydroxybenzotriazole (38 mg), 1-(3-dimethylaminopropyl)-3-ethylcarbodiimide hydrochloride (98 mg) and 3N methanol solution of ammonia (0.5 ml). After stirred at 20° C. for 14 hours, the resulting mixture was diluted with ethyl acetate. The organic phase was washed successively with 1N hydrochloric acid, water, aqueous sodium bicarbonate and brine, dried over sodium sulfate and evaporated in vacuo. The residue was triturated with isopropyl ether to give 3-acetyl-1-(2-chlorobenzyl)-2-propylindole-6-carboxamide (67 mg) as colorless crystals.

mp 208–211° C.; NMR (CDCl$_3$, δ): 1.01 (3H, t, J=7 Hz), 1.61 (2H, m), 2.73 (3H, s), 3.06 (2H, m), 5.49 (2H, s), 6.22 (1H, dd, J=1, 8 Hz), 7.02 (1H, dt, J=1, 8 Hz), 7.21 (1H, dt, J=1, 8 Hz), 7.45 (1H, dd, J=1, 8 Hz), 7.63 (1H, dd, J=1, 8 Hz), 7.84 (1H, d, J=8 Hz), 8.07 (1H, d, J=8 Hz).

EXAMPLE 4

Methyl 1-(2-chlorobenzyl)-3-isobutyryl-2-propylindole-6-carboxylate (533 mg) was prepared from methyl 3-isobutyryl-2-propylindole-6-carboxylate (440 mg, and 2-chlorobenzyl bromide (346 mg) in a similar manner to that of Example 1.

NMR (CDCl$_3$, δ): 1.01 (3H, t, J=8 Hz), 1.30 (6H, d, J=8 Hz), 1.55–1.66 (2H, m), 3.02–3.07 (12H, m), 3.58 (2H, septet, J=8 Hz), 3.90 (3H, s), 5.50 (2H, s), 6.24 (1H, dd, J=1, 8Hz), 7.05 (1H, dt, J=1, 8 Hz), 7.24 (1H, dt, J=1, 8 Hz), 7.46 (1H, dd, J=1, 8 Hz), 7.95 (1H, s), 7.97 (2H, s).

EXAMPLE 5

1-(2-Chlorobenzyl)-3-isobutyryl-2-propylindole-6-carboxylic acid (450 mg) was prepared from methyl 1-(2-chlorobenzyl)-3-isobutyryl-2-propylindole-6-carboxylate (510 mg) in a similar manner to that of Example 2.

NMR (DMSO-d$_6$, δ): 0.92 (3H, t, J=8 Hz), 1.18 (6H, d, J=8 Hz), 1.38–1.52 (2H, m), 3.02–3.08 (2H, m), 3.55 (2H, septet, J=8 Hz), 5.68 (2H, s), 6.28 (1H, dd, J=1, 8 Hz), 7.18 (1H, dt, J=1, 8 Hz), 7.32 (1H, dt, J=1, 8 Hz), 7.52 (1H, dd, J=1, 8 Hz), 7.84 (1H, dd, J=1, 8 Hz), 7.97 (1H, d, J1 Hz), 8.00 (H, d, J=8 Hz).

EXAMPLE 6

To a solution of 1-(2-chlorobenzyl)-3-isobutyryl-2-propylindole-6-carboxylic acid (150 mg) in dimethylformamide (3 ml) were added 1-hydroxybenzotriazole (102 mg), 1-(3-dimethylaminopropyl)-3-ethylcarbodiimide hydrochloride (109 mg). After stirred at 20° C. over night, the resulting mixture was poured into 28% aqueous ammonia (5 ml). The mixture was partitioned between ethyl acetate and water, and the organic phase was washed with 1N hydrochloric acid and brine, dried over sodium sulfate and evaporated in vacuo. The crystalline residue was recyrystallized from a mixture of ethyl acetate and hexane to give 1-(2-chlorobenzyl)-3-isobutyryl-2-propylindole-6-carboxamide (123 mg) as colorless crystals.

mp: 85–86° C. NMR (CDCl$_3$, δ): 1.01 (3H, t, J=8 Hz), 1.30 (6H, d, J=8 Hz), 1.55–1.66 (2H, m), 3.00–3.06 (2H, m), 3.56 (2H, septet, J=8 Hz), 5.49 (2H, s), 6.24 (2H, dd, J=1, 8 Hz), 7.04 (1H, dt, J=1, 8 Hz), 7.23 (1H, dt, J=1, 8 Hz), 7.46 (2H, dd, J=1, 8 Hz), 7.63 (1H=, dd, J=1, 8 Hz), 7.85 (1H, d, J=1 Hz), 7.97 (1H, d, J=8 Hz).

EXAMPLE 7

Methyl 1-(2-chlorobenzyl)-3-propionyl-2-propylindole-6-carboxylate (436 mg) was prepared from methyl 3-propionyl-2-propylindole-6-carboxylate (260 mg) and 2-chlorobenzyl bromide (216 mg) in a similar manner to that of Example 1.

NMR (CDCl$_3$, δ): 1.02 (3H, t, J=8 Hz), 1.30 (3H, t, J=8 Hz), 1.55–1.68 (2H, m), 3.00–3.16 (4H, m), 3.90 (3H, s), 5.49 (2H, s), 6.22 (1H, dd, J=1, 8 Hz), 7.05 (1H, dt, J=1, 8 Hz), 7.23 (1H, dt, J=1, 8 Hz), 7.46 (1H, dd, J=1, 8Hz), 7.93 (1H, d, J=8 Hz), 7.96 (1H, d, J=1, 8 Hz), 8.03 (1H, d, J=8 Hz).

EXAMPLE 8

1-(2-Chlorobenzyl)-3-propionyl-2-propylindole-6-carboxylic acid (308 mg) was prepared from methyl 1-(2-chlorobenzyl)-3-propionyl-2-propylindole-6-carboxylate (425 mg) in a similar manner to that of Example 2.

NMR (DMSO-d$_6$, δ): 0.94 (3H, J=8 Hz), 1.14 (3H, t, J=8 Hz), 1.49 (2H, Sextet, J=8 Hz), 3.00–3.10 (4H, m), 5.67 (2H, s), 6.27 (1H, dd, J=1, 8 Hz), 7.18 (1H, dt, J=1, 8 Hz), 7.32 (1H, dt, J=1, 8 Hz), 7.56 (1H, dd, J=1, 8 Hz), 7.83 (1H, dd, J=1, 8 Hz), 7.96 (1H, d, J=1 Hz), 8.09 (1H, d, J=8 Hz).

EXAMPLE 9

1-(2–Chlorobenzyl)-3-propionyl-2-propylindole-6-carboxamide (81 mg) was prepared from 1-2-chlorobenzyl)-3-propionyl-2-propylindole-6-carboxylic acid (100 mg) in a similar manner to that of Example 6.

mp: 151–152° C.; NMR (CDCl$_3$, δ): 1.02 (3H, t, J=8 Hz), 1.30 (3H, t, J=8 Hz), 1.62 (2H, sextet, J=8 Hz), 3.04–3.14 (4H, m), 5.50 (2H, s), 6.22 (1H, dd, J=1, 8 Hz), 7.03 (1H, dt, J=1, 8 Hz), 7.22 (1H, dt, J=1, 8 Hz), 7.45 (1H, dd, J=1, 8 Hz), 7.64 (H, dd, J=1, 8 Hz), 7.84 (1H, d, J=1 Hz), 8.06 (1H, d, J=8 Hz).

EXAMPLE 10

Methyl-(2-chlorobenzyl)-2-isobutyl-3-isobutyrylindole-6-carboxylate (258 mg) was prepared from methyl 2-isobutyl-3-isobutyrylindole-6-carboxylate (210 mg) and 2-chlorobenzyl bromide (157 mg) in a similar manner to that of Example 1.

NMR (CDCl$_3$, δ): 0.97 (6H, d, J=7 Hz), 1.31 (6H, d, J=7 Hz), 1.96–2.10 (1H, m), 3.04 (2H, d, J=7 Hz), 3.60 (1H, septet, J=7 Hz), 3.90 (3H, s), 5.53 (2H, s), 6.18 (1H, d, J=8 Hz), 7.04 (1H, t, J=8 Hz), 7.23 (1H, t, J=8 Hz), 7.46 )(1H, t, J=8 Hz), 7.94 (1H, s), 7.96 (2H, s).

EXAMPLE 11

1-(2-Chlorobenzyl)-2-isobutyl-3-isobutyrylindole-6-carboxylic acid (184 mg) was prepared from methyl 1-(2-chlorobenzyl)-2-isobutyl-3-isobutyrylindole-6-carboxylate (213 mg) in a similar manner to that of Example 2.

NMR (DMSO-d$_6$, δ): 0.88 (6H, d, J=8 Hz), 1.17 (6H, d, J=7 Hz), 1.82–1.95 (1H, m), 3.07 (2H, d, J=8 Hz), 3.57 (1H, septet, J=7 Hz), 5.68 (2H, s), 6.25 (1H, d, J=8 Hz), 7.18 (1H, t, J=8 Hz), 7.33 (1H, t, J=8 Hz), 7.57 (1H, d, J=8 Hz), 7.85 (1H, d, J=8 Hz), 7.95 (1H, s), 8.00 (1H, d, J=8 Hz).

EXAMPLE 12

1-(2-Chlorobenzyl)-2-isobutyl-3-isobutyrylindole-6-carboxamide (143 mg) was prepared from 1-(2-chlorobenzyl)-2-isobutyl-3-isobutyrylindole-6-carboxylic acid (160 mg) in a similar manner to that of Example 6.

NMR (DMSO-d$_6$, δ): 0.86 (6H, d, J=8 Hz), 1.17 (6H, d, J=7 Hz), 1.80–1.94 (1H, m), 3.02 (2H, d, J=8 Hz), 3.57 (1H, septet, J=7 Hz), 5.62 (2H, s), 6.16 (1H, d, J=8 Hz), 7.18 (1H, t, J=8 Hz), 7.30–7.35 (2H, m), 7.57 (1d, d, J=8 Hz), 7.82 (1H, d, J=8 Hz), 7.94 (1H, s), 7.96 (1H, d, J=8 Hz), 8.00 (1H, s).

EXAMPLE 13

Methyl 1-(2-chlorobenzyl)-2-ethyl-3-propylindole-6-carboxylate (278 mg) was prepared from methyl 2-ethyl-3-propionylindole-6-carboxylate (215 mg and 2-chlorobenzyl bromide (0.24 ml) in a similar manner to that of Example 1.

NMR (CDCl$_3$, δ): 1.22 (3H, t, J=7 Hz), 1.30 (3H, t, J=7 Hz), 3.05–3.20 (4H, m), 3.90 (3H, s), 5.50 (2H, s), 6.22 (1H, d, J=8 Hz), 7.02 (1H, t, J=8 Hz), 7.20 (1H, t, J=8 Hz), 7.46 (1H, d, J=8 Hz), 7.92 (1H, s), 7.95 (1H, d, J=8 Hz), 8.04 (1H, d, J=8 Hz).

EXAMPLE 14

1-(2-Chlorobenzyl)-2-ethyl-3-propionylindole-6-carboxylic acid (417 mg) was prepared from methyl 1-(2-Chlorobenzyl)-2-ethyl-3-propionylindole-6-carboxylate (453 mg) in a similar manner to that of Example 2.

NMR (DMSO-d$_6$, δ): 1.09 (3H, t, J=7 Hz), 1.17 (3H, t, J=7 Hz), 3.08 (2H, t, J=7 Hz), 3.11 (2H, t, J=7 Hz), 5.68 (2H, s), 6.24 (1H, d, J=8 Hz), 7.18 (1H, t, J=8 Hz), 7.31 (1H, t, J=8 Hz), 7.57 (1H, d, J=8 Hz), 7.83 (1H, d, J=8 Hz), 7.95 (1H, s), 8.13 (1H, d, J=8 Hz).

EXAMPLE 15

1-(2-Chlorobenzyl)-2-ethyl-3-propionylindole-6-carboxamide (242 mg) was prepared from 1-(2-chlorobenzyl)-2-ethyl-3-propionylindole-6-carboxylic acid (252 mg) in a similar manner to that of Example 3.

NMR (CDCl$_3$, δ): 1.23 (3H, t, J=7 Hz), 1.29 (3H, t, J=7 Hz), 3.08–3.18 (4H, m), 5.49 (2H, s), 6.19 (1H, d, J=8 Hz), 7.02 (1H, t, J=8 Hz), 7.2 (1H, t, J=8 Hz), 7.46 (1H, d, J=8 Hz) 7.62 (1H, d, J=8 Hz), 7.83 (1H, s), 8.09 (1H, d, J=8 Hz).

EXAMPLE 16

Methyl 2-acetyl-1-(2-chlorobenzyl)-3-isobutylindole-6-carboxylate (71.4 mg) was prepared from methyl 2-acetyl-3-isobutylindole-6-carboxylate (58 mg) and 2-chlorobenzyl bromide (0.04 ml) in a similar manner to that of Example 1.

NMR (CDCl$_3$, δ): 1.02 (6H, d, J=7 Hz), 2.02 (1H, m), 2.59 (3H, s), 3.01 (2H, d, J=7 Hz), 3.90 (3H, s), 5.84 (2H, s), 6.19 (1H, d, J=8 Hz), 6.99 (1H, t, J=8 Hz), 7.15 (1H, t, J=8 Hz), 7.40 (1H, d, J=8 Hz), 7.75 (1H, d, J=8 Hz), 7.83 (1H, d, J=8 Hz), 7.98 (1H, s).

EXAMPLE 17

2-Acetyl-1-(2-chlorobenzyl)-3-isobutylindole-6-carboxylic aced (45.3 mg) was prepared from methyl 2-acetyl-1-(2-chlorobenzyl)-3-isobutylindole-6-carboxylate (67 mg) in a similar manner to that of Example 2.

NMR (CDCl$_3$, δ): 1.02 (6H, d, J=7 Hz), 2.03 (1H, m), 2.62 (3H, s), 3.03 (2H, d, J=7 Hz), 5.76 (2H, s), 6.19 (1H, d, J=8 Hz), 7.00 (1H, t, J8 Hz), 7.14 (1H, t, J=8 Hz), 7.41 (1H, d, J=8 Hz), 7.77 (1H, d, J=8 Hz), 7.86 (1H, d, J=8 Hz), 8.02 (1H, s).

EXAMPLE 18

2-Acetyl-1-(2-chlorobenzyl)-3-isobutylindole-6-carboxamide (33.4 mg) was prepared from. 2-acetyl-1-(2-chlorobenzyl)-3-isobutylindole-6-carboxylic acid (41.7 mg) in a similar manner to that of Example 3.

NMR (CDCl$_3$, δ): 1.01 (6H, d, J=7 Hz), 2.02 (1H, m), 2.62 (3H, s), 3.03 (2H, d, J=7 Hz), 5.54 (2H, s), 6.22 (1H, d, J=8 Hz), 6.99 (1H, t, J=8 Hz), 7.16 (1H, t, J=8 Hz), 7.41 (1H, d, J=8 Hz), 7.54 (1H, d, J=8 Hz), 7.78 (1H, d, J=8 Hz), 7.79 (1H, s).

EXAMPLE 19

Methyl 1-(2-chlorobenzyl)-3-ethyl-2-propionylindole-6-carboxylate (66 mg) was prepared from methyl 3-ethyl-2-propionylindole-6-carboxylate (88 mg) and 2-chlorobenzyl bromide (0.051 ml) in a similar manner to that of Example 1.

NMR (CDCl$_3$, δ): 1.16 (3H, t, J=7 Hz), 1.38 (3H, t, J=7 Hz), 2.95 (2H, q, J=7 Hz), 3.14 (2H, q, J=7 Hz), 3.90 (3H, s), 5.72 (2H, s), 6.23 (1H, d, J=8 Hz), 6.98 (1H, t, J=8 Hz), 7.14 (1H, t, J=8 Hz), 7.39 (1H, d, J=8 Hz), 7.77 (1H, d, J=8 Hz), 7.85 (1H, s), 7.97 (1H, s).

EXAMPLE 20

1-(2-Chlorobenzyl)-3-ethyl-2-propionylindole-6-carboxylic acid (48.7 mg) was prepared from methyl 1-(2-chlorobenzyl)-3-ethyl-2propionylindole-6-carboxylate (59.4 mg) in a similar manner to that of Example 2.

NMR (CDCl$_3$, δ): 1.16 (3H, t, J=7 Hz), 1.37 (3H, t, J=7 Hz), 2.94 (2H, q, J=7 Hz), 3.15 (2H, q, J=7 Hz), 5.72 (2H, s), 6.25 (1H, d, J=8 Hz), 6.99 (1H, t, J=8 Hz), 7.15 (1H, t, J=8 Hz), 7.40 (1H, d, J=8 Hz), 7.78 (1H, d, J=8 Hz), 7.87 (1H d, J=8 Hz), 8.01 (1H, s).

EXAMPLE 21

1-(2-Chlorobenzyl)-3-ethyl-2-propionylindole-6-carboxamide (40.4 mg) was prepared from 1-(2-chlorobenzyl)-3-ethyl-2-propionylindole-6-carboxylic acid (46 mg) in a similar manner to that of Example 3.

NMR (CDCl$_3$, δ): 1.16 (3H, t, J=7 Hz), 1.38 (3H, t, J=7 Hz), 2.96 (2H, q, J=7 Hz), 3.14 (2H, q, J=7 Hz), 5.72 (2H, s), 6.25 (1H, d, J=8 Hz), 7.00 (1H, t, J=8 Hz), 7.14 (1H, t, J=8 Hz), 7.39 (1T, d, J=8 Hz), 7.56 (1H, d, J=8 Hz), 7.79 (1H, s), 7.80 (1H, d, J=8 Hz).

EXAMPLE 22

The following compounds described in 1) to 6) were prepared by reacting the compound (I-2) obtained in Example 2 or Example 34-19), and a suitable amine (IV) in a similar manner to that of Example 3.

(1) 3-Acetyl-1-(2-chlorobenzyl)-N,N-dimethyl-2-propylindole-6-carboxamide mp: 150–153° C.; NMR (CDCl$_3$, δ): 1.03 (3H, t, J=7 Hz), 1.63 (2H, m), 2.72 (3H, s), 2.98 (6H, br s), 3.09 (2H, m), 5.44 (2H, s), 6.26 (1H, dd, J=1, 8 Hz), 7.03 (1H, dt, J=1, 8 Hz), 7.20 (1H, dt, J=1, 8 Hz), 7.29 (1H, s), 7.35 (1H, d, J=8 Hz), 7.43 (1H, dd, J=1, 8 Hz), 8.03 (1H, d, J=8 Hz).

(2) 3-Acetyl-1-(2-chlorobenzyl)-N-cyclopropylmethyl-2-propylindole-6-carboxamide mp: 158–162° C.; NMR (CDCl$_3$, δ): 0.28 (2H, m), 0.55 (2H, m), 1.03 (3H, t, J=7 Hz), 1.05 (1H, m), 1. 60 (2H, m), 2.72 (3H, s), 3.04 (2H, m), 3.31 (2H, m), 5.49 (2H, s), 6.22 (1H, d, J=8 Hz), 6.28 (1H, m), 7.03 (1H, t, J=8 Hz), 7.22 (1H, t, J=8 Hz), 7.45 (1H, d, J=8 Hz), 7.61 (1H, dd, J=1, 8 Hz), 7.82 (1H, d, J=1 Hz), 8.05 (1H, d, J=8 Hz).

(3) 3-Acetyl-1-(2-chlorobenzyl)-N-(2-pyridylmethyl)-2-propylindole-6-carboxamide mp: 172–175° C.; NMR (CDCl$_3$, δ): 1.02 (3H, t, J=7 Hz), 1.63 (2H, m), 2.73 (3H, s), 3.07 (2H, m), 4.75 (2H, d, J=5 Hz), 5.51 (2H, s), 6.22 (1H, d, J=8 Hz), 7.02 (1H, t, J=8 Hz), 7.15–7.27 (2H, m), 7.33 (1H, d, J=8 Hz), 7.44 (1H, d, J=8 Hz), 7.58–7.76(3H, s), 7.88 (1H, s), 8.07 (1H, d, J=8 Hz), 8.56 (1H, m).

(4) 3-Acetyl-1-(2-chlorobenzyl)-6-(morpholinocarbonyl)-2-propylindole

NMR (CDCl$_3$ δ): 1.03 (3H, t, J=7 Hz), 1.63 (2H, m), 2.73 (3H, s), 3.09 (2H, m), 3.63 (8H, br s), 5.44 (2H, s), 6.23 (1H, d, J=8 Hz), 7.06 (1H, t, J=8 Hz), 7.2–7.4 (3H, m), 7.46 (1H, d, J=8 Hz), 8.06 (1H, d, J=8 Hz).

(5) 3-Acetyl-1-(2-chlorobenzyl)-N-phenylsulfonyl-2-propylindole-6-carboxamide mp: 206–208° C.; NMR (CDCl$_3$, δ): 0.99 (3H, t, J=7 Hz), 1.54 (2H, m), 2.72 (3H, s), 3.02 (2H, m), 5.43 (2H, s), 6.13 (1H, d, J=8 Hz), 7.00 (1H, t, J=8 Hz), 7.21 (1H, t, J=8 Hz), 7.43 (1H, d, J=8 Hz), 7.5–7.7 (4H, m), 7.77 (1H, s), 8.08 (1H, d, J=9 Hz), 8.13–8.18 (2H, m), 8.81 (1H br s).

(6) 1-(2-chlorobenzyl)-3-formyl-N-phenylsulfonyl-2-propylindole-6-carboxamide mp 242–245° C.; NMR (CDCl$_3$, δ): 0.87 (3H, t, J=7 Hz), 1.49 (2H, m), 3.07 (2H, t, J=7 Hz), 5.66 (2H, s), 6.32 (1H, d, J=8 Hz), 7.18 (1H, t, J=8 Hz), 7.33 (1H, t, J=8 Hz), 7.55–7.75 (4H, m), 7.88 (1H, m), 7.96 (1H, s), 7.98 (1H, d, J=8 Hz), 8.09 (1H, s), 8.23 (1H, d, J=8 Hz).

(7) 1-(2-Chlorobenzyl)-3-formyl-2-propyl-N-(1H-tetrazol-5-yl)indole-6-carboxamide mp 275° C. (dec.); NMR (DMSO-$d_6$, $\delta$): 0.90 (3H, t, J=7 Hz), 1.54 (2H, m), 3.13 (2H, t, J=7 Hz), 5.69 (2H, s), 6.38 (1H, d, J=8 Hz), 7.19 (1H, t, J=8 Hz), 7.33 (1H, t, J=8 Hz), 7.60 (1H, d, J=8 Hz), 8.03 (1H, d, J=8 Hz), 8.31 (1H, s), 8.32 (7H, d, J=8 Hz), >10 (1H, s).

EXAMPLE 23

1-Hydroxybenzotriazole (68 mg) and 1-(3-dimethylaminopropyl)-3-ethylcarbodiimide hydrochloride (72 mg) were added to a solution of 1-(2-chlorobenzyl)-3-isobutyryl-2-propylindole-6-carboxylic acid (100 mg) in dimethylformamide (3 ml), and the mixture was stirred at 20° C. overnight, then hydroxylamine hydrochloride (35 mg) and diisopropylethylamine (0.088 ml) were added. After stirred at 20° C. for 2 hours, the reaction mixture was partitioned between ethyl acetate and water. The organic phase was washed with 1N hydrochloric acid and brine, dried over sodium sulfate, and evaporated in vacuo. The residue was purified by preparative thin layer chromatography with 10% methanol in chloroform and recrystallization from ethyl acetate to give 1-(2-chlorobenzyl)-3-isobutyryl-2-propylindole-6-carbohydroxamic acid (67 mg) as pale red crystals.

mp: 185–186° C.; NMR (CDCl$_3$, $\delta$): 1.00 (3H, t, J=8 Hz), 1.28 (6H, d, J=8 Hz), 1.60 (2H, sextet, J=8 Hz), 3.02–3.06 (2H, m), 3.53 (2H, septet, J=8 Hz), 5.47 (2H, s), 6.20 (1H, dd, J=1, 8 Hz), 7.03 (1H, t, J=8 Hz), 7.20 (1H, t, J=8 Hz), 7.46 (1H, d, J=8 Hz), 7.57 (1H, d, J=8 Hz), 7.77 (1H, s), 7.97 (1H, d, J=8 Hz).

EXAMPLE 24

The following compounds described in 1) to 2) were prepared by reacting the compound (1-2) obtained in Example 5 and a suitable amine (IV) in a similar manner to that of (1) 1-(2-Chlorobenzyl)-3-isobutyryl-O-methyl-2-propylindole-6-carbohydroxamic acid NMR (CDCl$_3$, $\delta$): 1.00 (3H, t, J=8 Hz), 1.30 (6H, d, J=8 Hz), 1.54–1.66 (2H, m), 3.00–3.06 (2H, m), 3.53 (1H, septet, J=8 Hz), 3.86 (3H, s), 5.49 (2H, s), 6.22 (1H, dd, J=1, 8 Hz), 7.03 (1H, dt, J=1, 8 Hz), 7.23 (1H, dt, J=1, 8 Hz), 7.46 (1H, dd, J=1, 8 Hz), 7.56 (1H, dd, J=1, 8 Hz), 7.75 (1H, d, J=1 Hz), 7.96 (1H, d, J=8 Hz), 8.82 (1H, s).

(2) 1-(2-Chlorobenzyl)-3-isobutyl-2-propyl-N-(2-pyridylmethyl)indole-6-carboxamide NMR (CDCl$_3$, $\delta$): 1.00 (3H, t, J=8 Hz), 1.30 (6H, d, J=8 Hz), 1.62 (2H, sextet, J=8 Hz), 3.03–3.07 (2H, m), 3.57 (1H, septet, J=8 Hz), 4.66 (2H, d, J=6 Hz), 5.50 (2H, s), 6.24 (1H, dd, J=1, 8 Hz), 7.02 (1H, dt, J=1, 8 Hz), 7.18–7.24 (2H, m), 7.33 (1H, d, J=8 Hz), 7.45 (1H, d, J=8 Hz), 7.62–7.68 (2H, m), 7.72 (1H, dd, J=1, 8 Hz), 7.88 (1H, d, J=1 Hz), 7.98 (1H, d, J=8 Hz), 8.56 (1H, d, J=6 Hz).

EXAMPLE 25

The following compounds described in 1) to 2) were prepared by reacting the compound (II) obtained in Preparation 8 (2) and a suitable halide (III) in a similar manner to that of example 1.

(1) 1-(4-Chloro-2-fluorobenzyl)-3-isobutyryl-2-propylindole-6-carboxamide mp: 200–202° C.; IR (KBr): 3380, 3195, 1650, 1620 cm$^{-1}$; NMR (CDCl$_3$, $\delta$): 1.03 (3H, t, J=7 Hz), 1.30 (6H, d, J=7 Hz), 1.52–1.65 (2H, m), 3.06–3.10 (2H, m), 3.49–3.59 (1H, m), 5.47 (2H, s), 6.34 (1H, ddd, J=8, 8, 1 Hz), 6.94 (1H, dd, J=8, 1 Hz), 7.19 (1H, d, J=8 Hz), 7.60 (1H, d, J=8 Hz), 7.89 (1H, s), 7.97 (1H, d, J=8 Hz); MASS (m/z): 415 (M$^+$+1), 76 (bp).

(2) 3-Isobutyryl-(2-methoxycarbonylbenzyl)-2-propylindole-6-carboxamide mp: 170–172° C.; IR (KBr): 3420, 1720, 1650 cm$^{-1}$; NMR (CDCl$_3$, $\delta$): 1.00 (3H, t, J=7 Hz), 1.33 (6H, d, J=7 Hz), 1.56–1.69 (2H, m), 3.00–3.06 (2H, m), 3.54–3.63 (1H, m), 4.02 (3H, s), 5.91 (2H, s), 6.69 (1H, d, J=7.5 Hz), 7.24–7.36 (1H, m,), 7.63 (1H, dd, J=8, 1 Hz), 7.80 (1H, s), 7.99 (1H, d, J=8 Hz), 8.12–8.16 (1H, m); MASS (m/z): 421 (M$^+$+1).

EXAMPLE 26

A mixture of 3-isobutyryl-2-propylindole-6-carboxamide (100 mg), 4-chlorobenzyl bromine (113 mg) and potassium carbonate (152 mg) in dimethylformamide (2 ml) was heated at 60° C. or 2 hours, and partitioned between ethyl acetate and water. The organic layer was washed with water and brine, and dried over magnesium sulfate. After evaporation of solvent, the residue was crystallized from a mixture of ethyl acetate and hexane. The crude crystals were recrystallized from a mixture of ethyl acetate and hexane to give 1-(4-chlorobenzyl)-3-isobutyryl-2-propylindole-6-carboxamide (97 mg) as colorless crystals.

mp: 183–184° C. NMR (CDCl$_3$, $\delta$): 1.01 (3H, t, J=7 Hz), 1.29 (6H, d, J=7 Hz), 1.50–1.64 (2H, m), 3.06–3.12 (2H, m), 3.55 (2H, septet, J=7 Hz), 3.42 (2H, s), 6.87 (2H, d, J=3 Hz), 7.25 (2H, d, J=8 Hz), 7.60 (1H, dd, J=1, 8 Hz), 7.27 (1H, d, J=1 Hz), 7.95 (1H, d, J=8 Hz).

EXAMPLE 27

The following compounds described in 1) to 8) were prepared by reacting the compound (II) obtained in preparation 8 (2) or Preparation 15 (3), and a suitable halide (III) in a similar manner to that of Example 26.

(1) 1-Benzyl-3-isobutyryl-2-propylindole-6-carboxamide mp: 164–166° C.; NMR (CDCl$_3$, $\delta$): 1.00 (3H, t, J=7 Hz), 1.29 (6H, d, J=7 Hz), 1.60 (2H, septet, J=7 Hz), 3.09–3.13 (2H, m), 3.55 (2H, septet, J=7 Hz), 5.46 (2H, s), 6.96–6.98 (2H, m), 7.24–7.32 (2H, m), 7.61 (1H, d, J=8 Hz), 7.91 (1H, s), 7.95 (1H, d, J=8 Hz).

(2) 1-(3-Chlorobenzyl)-3-isobutyryl-2-propylindole-6-carboxamide mp: 164–166° C.; NMR (CDCl$_3$, $\delta$): 1.00 (3H, t, J=7 Hz), 1.30 (6H, d, J=7 Hz), 1.50–1.65 (2H, m), 3.06–3.12 (2H, m), 3.55 (2H, septet, J=7 Hz), 5.42 (2H, s), 6.78 (1H, dd, J=1, 8 Hz), 6.96 (1H, d, J=1 Hz), 7.18–7.27 (2H, m), 7.60 (1H, d, J=8 Hz), 7.88 (1H, s), 7.95 (1H, d, J=8 Hz).

(3) 3-Isobutyryl-2-propyl-1-(2-trifluororomethlbenzyl)indole-6-carboxamide mp: 86–87° C.; NMR (CDCl$_3$, $\delta$): 0.99 (3H, t, J=7 Hz), 1.30 (6H, d, J=7 Hz), 1.52–1.65 (2H, m), 2.98–3.04 (2H, m), 3.56 (2H, septet, J=7 Hz), 5.62 (2H, s), 6.33 (1H, d, J=8 Hz), 7.30 (1H, 7, J=1 Hz), 7.38 (1H, t, J=1 Hz), 7.64 (1H, d, J=8 Hz), 7.75 (1H, d, J=8 Hz), 7.84 (1H, s), 7.98 (1H, d, J=8 Hz).

(4) 3-Isobutyryl-1-(2-phenylbenzyl)-2-propylindole-6-carboxamide mp: 162–164° C.; NMR (CDCl$_3$, $\delta$): 0.89 (3H, t, J=7 Hz), 1.27 (6H, d, J=7 Hz), 1.36–1.50 (2H, m), 2.90–2.96 (2H, m), 3.53 (2H, septet, J=7 Hz), 5.32 (2H, s), 6.48 (1H, d, J=8 Hz), 7.10–7.16 (1H, m), 7.30–7.34 (2H, m), 7.42–7.84 (3H, m), 7.52–7.55 (2H, m), 7.60 (1H, d, J=8 Hz), 7.84 (1H, s), 7.93 (1H, d, J=8 Hz).

(5) 1-[(5-Chlorothien-2-yl)methyl]-3-isobutyryl-2-propylindole-6-carboxamide mp: 178–180° C.; NMR (CDCl$_3$, δ): 1.07 (3H, t, J=7 Hz), 1.27 (6H, d, J=7 Hz), 1.65 (2H, sextet, J=7 Hz), 3.15–3.20 (2H, m), 3.54 (2H, septet, J=7 Hz), 5.46 (2H, s), 6.59 (1H, d, J=2 Hz), 6.72 (2H, d, J=2 Hz), 7.60 (1H, d, J=8 Hz), 7.92 (1H, d, J=8 Hz), 8.04 (1H, s).

(6) 3-Isobutyryl-1-phenylethyl-2-propylindole-6-carboxamide mp: 180–181° C.; NMR (CDCl$_3$, δ): 1.02 (3H, t, J=7 Hz), 1.26 (6H, d, J=7 Hz), 1.61 (2H, septet, J=7 Hz), 2.88–2.92 (2H, m), 3.10 (2H, t, J=7 Hz), 3.52 (2H, septet, J=7 Hz), 4.42 (2H, t, J=7 Hz), 7.05–7.09 (2H, m), 7.22–7.32 (3H, m), 7.52 (1H, d, J=8 Hz), 7.92 (1H, d, J=8 Hz), 7.96 (1H, s).

(7) 1-(2-Chlorobenzyl)-3-methoxyacetyl-2-propylindole-6-carboxamide mp: 165–167° C.; NMR (DMSO-d$_6$, δ): 0.92 (3H, t, J=8 Hz), 1.46 (2H, sextet, J=8 Hz), 3.01–3.05 (2H, m), 3.42 (3H, s), 4.68 (2H, s), 5.62 (2H, s), 6.22 (1H, d, J=8 Hz), 7.16 (1H, t, J=8 Hz), 7.28 (1H, br s), 7.32 (1H, t, J=8 Hz), 7.56 (1H, d, J=8 Hz), 7.92 (1H, d, J=8 Hz), 7.93 (1H, br s), 8.01 (1H, s).

(8) 1-(6-Chloro-3,4-methylenedioxybenzyl)-3-methoxyacetyl-2-propylindole-6-carboxamide mp 204–206° C.; NMR (DMSO-d$_6$, δ): 0.95 (3H, t, J=8 Hz), 1.50 (2H, sextet, J=8 Hz), 3.02–3.06 (2H, m), 3.40 (3H, s), 4.70 (2H, s), 5.51 (1H, s), 5.98 (2H, s), 7.23 (1H, s), 7.32 (1H, br s), 7.80 (1H, d, J=8 Hz), 7.93 (1H, d, J=8 Hz), 7.96 (1H, br s), 8.02 (1H, s).

EXAMPLE 28

The following compounds described in 1) to 16) were prepared by reacting the compound (II) obtained in Preparation 2, Preparation 6 (1), Preparation 9, Preparation 10, Preparation 12, Preparation 13 (4) or Preparation 14 (5) and a suitable halide (III) in a similar manner to that of Example 1.

(1) Methyl 1-(2fluorobenzyl-3-isobutyryl-2-propylindole-6-carboxylate mp: 120–121.5° C.; IR (KBr): 1710, 1700, 1660 cm$^{-1}$; NMR (CDCl$_3$, δ): 1.02 (3H, t, J=7 Hz), 1.29 (6H, d, J=7 Hz), 1.55–1.64 (2H, m), 3.06–3.12 (2H, m), 3.51–3.61 (1H, m), 3.92 (3H, s), 5.50 (2H, s), 6.43 (1H, t, J=7.5 Hz), 6.95 (1H, t, J=7 Hz), 7.10–7.17 (1H, m), 7.22–7.28 (1H, m), 7.95 (2H, s), 8.02 (1H, s); MASS (m/z): 396 (M$^+$+1), 76 (bp).

(2) Methyl (1-(2-bromobenzyl)-3-isobutyryl-2-propylindole-6-carboxylate mp 90–92° C.; IR (KBr): 1705, 1650 cm$^{-1}$; NMR (CDCl$_3$, δ): 1.02 (3H, t, J=7 Hz), 1.30 (6H, d, J=7 Hz), 1.56–1.67 (2H, m), 3.04 (2H, t, J=7 Hz), 3.51–3.61 (1H, m), 3.92 (3H, s), 5.50 (2H, s), 6.43 (1H, t, J=7.5 Hz), 6.95 (1H, t, J=7.5 Hz), 7.10–7.17 (1H, m), 7.22–7.28 (1H, m), 7.95 (2H, s), 7.97 (2H, s); MASS (m/z): 458 (M$^+$+1+2), 458 (M$^+$+1), 76 (bp).

(13) Methyl 1-(2-iodobenzyl)-3-isobutyryl-2-propylindole-6-carboxylate

IR (KBr): 1710, 1650, 1430 cm$^{-1}$; NMR (CDCl$_3$, δ): 1.03 (3H, t, J=7 Hz), 1.30 (6H, d, J=7 Hz), 1.53–1.67 (2H, m), 2.98–3.05 (2H, m), 3.53–3.62 (1H, m), 3.93 (3H, s), 5.37 (2H, s), 6.16 (1H, t, J=7.2 Hz), 6.99 (1H, t, J=7.5 Hz), 7.12 (1H, t, J=7.5 Hz), 7.90–7.97 (4H, m); MASS (m/z): 504 (M$^+$+1).

(4) Methyl 3-isobutyryl-1-(2-methylbenzyl)-2-propylindole-6-carboxylate mp: 99–102° C.; IR (KBr): 1705, 1650, 1285 cm$^{-1}$; NMR (CDCl$_3$, δ): 1.00 (3H, t, J=7 Hz), 1.30 (6H, d, J=7 Hz), 1.54–1.69 (2H, m), 2.50 (3H, s), 3.00–3.06 (2H, m), 3.51–3.65 (1H, m), 3.89 (3H, s), 5.39 (2H, s), 6.17 (1H, t, J=7.5 Hz), 6.98 (1H, t, J=7.5 Hz), 7.18 (1H, t, J=7.5 Hz), 7.25 (1H, d, J=7.5 Hz), 7.92 (1H, s), 7.96 (2H, s); MASS (m/z): 392 (M$^+$+1).

(5) Methyl 3-isobutyryl-1-(2-methoxybenzyl)-2-propylindole-6-carboxylate mp: 103–105° C.; IR (KBr): 1710, 1650 cm$^{-1}$; NMR (CDCl$_3$, δ): 1.01 (3H, t, J=7 Hz), 1.30 (6H, d, J=7 Hz), 1.56–1.68 (2H, m), 3.05–3.10 (2H, m), 3.53–3.62 (1H, m), 3.90 (3H, s), 3.98 (3H, s), 5.44 (2H, s), 6.27 (1H, d, J=7.5 Hz), 6.74 (1H, t, J=7.5 Hz), 6.94 (1H, d, J=7.5 Hz), 7.25 (1H, t, J=7.5 Hz), 7.95 (2H, s), 8.00 (1H, d, J=7.5 Hz); MASS (m/z): 408 (M$^+$+1), 76 (bp).

(6) Methyl 1-(2-cyanobenzyl)-3-isobutyryl-2-propylindole- 6-carboxylate mp: 159–161° C.; IR (KBr): 2220, 1730, 1660 cm$^{-1}$; NMR (CDCl$_3$, δ): 1.04 (3H, t, J=7 Hz), 1.30 (6H, d, J=7 Hz), 1.52–1.65 (2H, m), 3.03–3.08 (2H, m), 3.53–3.60 (1H, m), 3.92 (3H, s), 5.66 (2H, s), 6.44–6.49 (1H, m), 7.38–7.43 (2H, m), 7.76–7.80 (1H, m), 7.95 (1H, s), 7.98 (2H, s); MASS (m/z): 403 (M$^+$+1), 76 (bp).

(7) Methyl 3-isobutyryl-1-(2-nitrobenzyl)-2-propylindole-6-carboxylate mp: 165.5–166.5° C.; IR (KBr): 1705, 1650, 1530, 1520 cm$^{-1}$; NMR (CDCl$_3$, δ): 1.00 (3H, t, J=7 Hz), 1.31 (6H, d, J=7 Hz), 1.56–1.65 (2H, m), 3.03 (2H, t, J=7 Hz), 3.54–3.65 (1H, m), 3.90 (3H, s), 5.89 (2H, s), 6.27 (1H, d, J=7.5 Hz), 7.40–7.51 (2H, m), 7.89 (1H, s), 8.00 (2H, s), 8.30 (1H, d, J=7.5 Hz); MASS (m/z): 423 (M$^+$+1), 76 (bp).

(8) Methyl 1-(2,6-dichlorobenzyl)-3-isobutyryl-2-propylindole-6-carboxylate mp: 129.5–132° C.; IR (KBr): 1710, 1660, 1430 cm$^{-1}$; NMR (CDCl$_3$, δ): 0.96 (3H, t, J=7 Hz), 1.27 (6H, d, J=7 Hz), 1.38–1.50 (2H, m), 3.15–3.20 (2H, m), 3.47–3.60 (1H, m), 3.92 (3H, s), 5.70 (2H, s), 7.17–7.39 (3H, m), 7.88 (2H, s), 8.03 (1H, s); MASS (m/z): 446 (M$^+$+1).

(9) Methyl 1-(2-chloro-fluorobenzyl)-3-isobutyryl-2-propylindole-6-carboxylate mp: 140–141° C.; IR (KBr): 705, 1649, 1488, 1279 cm$^{-1}$; NMR (CDCl$_3$, δ): 1.03 (3H, t, J=7 Hz), 1.40 (6H, d, J=7 Hz), 1.52–1.66 (2H, m), 3.01–3.06 (2H, m), 3.52–3.60 (1H, m), 3.93 (3H, s), 5.48 (2H, s), 6.20–6.25 (1H, m), 6.79 (1H, ddd, J=7.5, 7.5, 1 Hz), 7.21–7.25 (1H, m), 7.94 (1H, s), 7.97 (2H, s); MASS (m/z): 430 (M$^+$+1), 76 (bp).

(10) Methyl 1-(4-bromo-2-fluorobenzyl)-3-isobutyryl-2-propylindole-6-carboxylate mp: 110–111.5° C.; IR (KBr): 1705, 1649, 1488, 1279 cm$^{-1}$; NMR (CDCl$_3$, δ): 1.03 (3H, t, J=7 Hz), 1.29 (6H, d, J=7 Hz), 1.53–1.65 (2H, m), 3.05–3.10 (2H, m), 3.51–3.60 (1H, m), 3.94 (3H, s), 5.44 (2H, s), 6.28 (1H, d, J=7.5 Hz), 7.10 (1H, dd, J=7.5, 1 Hz), 7.35 (1H, d, J=7.5 Hz), 7.96 (1H, s); MASS (m/z) 476 (M$^+$+1), 474 (M$^+$), 76 (bp).

(11) Methyl 3-benzoyl-1-(2-chlorobenzyl)-2-propylindole-6-carboxylate NMR (CDCl$_3$, δ): 0.94 (3H, t, J=8 Hz), 1.56–1.70 (2H, m), 2.93–2.98 (2H, m), 3.87 (3H, s), 5.55 (2H, s), 6.33 (1H, ddd, J=1, 8 Hz), 7.08 (1H, d, J=1, 8 Hz), 7.2 (1H, d, J=8 Hz), 7.22–7.28 (1H, m), 7.46–7.52 (3H, m), 7.57–7.63 (1H, m), 7.72–7.82 (3H, m), 7.93 (1H, d, J=1 Hz).

(12) Methyl 1-(2-chlorobenzyl)-3-cyano-2-propylindole-6-carboxylate mp: 132–133° C.; IR (KBr): 2215, 1709, 1284 cm$^{-1}$; NMR (CDCl$_3$, δ): 1.01 (3H, t, J=7 Hz), 1.70 (2H, sextet, J=7 Hz), 2.89 (2H, t, J=7.5 Hz), 3.92 (3H, s), 5.49 (2H, s), 6.24 (1H, d, J=7.5 Hz), 7.08 (1H, t, J=7.5 Hz), 7.22–7.28 (1H, m), 7.47 (1H, d, J=7.5 Hz), 7.77 (1H, d, J=7.5 Hz), 9.95–8.00 (2H, m); MASS (m/z) 367 (M$^+$1), 76 (bp).

(13) Methyl 1-(2-chlorobenzyl)-2-ethyl-3-isobutyrylindole-6-carboxylate

NMR (CDCl$_3$, δ): 1.22 (3H, t, J=7 Hz), 1.31 (6H, d, J=7 Hz), 3.08 (2H, q, J=7 Hz), 3.56 (1H, m), 3.91 (3H, s), 5.50 (2H, s), 6.23 (1H, d, J=8 Hz), 7.04 (1H, t, J=8 Hz), 7.22 (1H, t, J=8 Hz), 7.46 (1H, d, J=8 Hz,), 7.93–7.98 (3H, m).

(14) Methyl 1-(2-chlorobenzyl)-3-isobutyryl-2-methylindole-6-carboxylate

NMR (CDCl$_3$, δ): 1.32 (6H, d, J=7 Hz), 2.71 (3H, s), 3.56 (1H, m), 3.92 (3H, s), 5.52 (2H, s), 6.24 (1H, d, J=8 Hz), 7.05 (1H, t, J=8 Hz), 7.23 (1H, t, J=8 Hz), 7.46 (1H, d, J=8 Hz), 7.92–8.05 (3H, m).

(15) Methyl 1-(2-chlorobenzyl)-3-isobutyryl-2-methoxymethylindole-6-carboxylate

NMR (CDCl$_3$, δ): 1.29 (6H, d, J=7 Hz) 3.31 (3H, s), 3.55 (1H, m, 3.89 (3H, s), 4.91 (2H, s), 5.63 (2H, s), 6.23 (1H, d, J=8 Hz), 7.02 (1H, t, J=8 Hz), 7.19 (1H, t, J=8 Hz), 7.44 (1H, d, J=8 Hz), 7.95–8.02 (3H, m).

(16) Methyl 1-2-chlorobenzyl)-3-isobutyrylindole-6-carboxylate

NMR (CDCl$_3$, δ): 1.26 (6H, d, J=7 Hz), 3.28 (1H, m), 3.93 (3H, s), 5.52 (2H, s), 6.77 (1H, d, J=8 Hz), 7.18 (1H, t, J=8 Hz), 7.29 (1H, t, J=8 Hz), 7.48 (1H, d, J=8 Hz), 7.89 (1H, s), 8.02 (1H, d, J=8 Hz), 8.10 (1H, s), 8.49 (1H, d, J=8 Hz).

EXAMPLE 29

The following compounds described in 1) to 2) were prepared from the compound (II) obtained in Preparation 1 (5) and Preparation 2 in a similar manner to that of Example 26.

(1) Methyl 3-isobutyryl-2-propyl-1-(2-pyridylmethyl)indole-6-carboxylate

NMR (CDCl$_3$, δ): 1.01 (3H, t, J=7 Hz), 1.30 (6H, d, J=7 Hz), 1.60 (2H, sextet, J=7 Hz), 3.12–3.16 (2H, m), 3.56 (2H, septet, J=7 Hz), 3.90 (3H, s), 5.58 (2H, s), 6.58 (1H, d, J=8 Hz), 7.22 (1H, dd, J=5, 8 Hz), 7.55 (1H, dt, J=1, 8 Hz), 7.94 (2H, s), 8.02 (1H s), 8.63 (1H, dd, J=1, 5 Hz).

(2) Methyl 3-acetyl-1-(6-chloro-3,4-methylenedioxybenzyl)-2-propylindole-6-carboxylate mp: 210–212° C.; NMR (CDCl$_3$, δ): 1.04 (3H, t, J=7 Hz), 1.63 (2H, sextet, J=7 Hz), 2.37 (3H, s), 3.04–3.08 (2H, m), 3.92 (3H, s), 5.40 (2H, s), 5.70 (1H, s), 5.90 (2H, s), 6.92 (1H, s), 7.95 (1H, s), 7.97 (1H, d, J=8 Hz), 8.04 (1H, d, J=8 Hz).

EXAMPLE 30

To a solution of methyl 3-acetyl-1-(2-chlorobenzyl)-2-ethylindole-6-carboxylate (110 mg) in tetrahydrofuran, (5 ml) was added 1M solution of boron in tetrahydrofuran (0.6 ml) in one portion at 0° C. The mixture was stirred at 20° C. for 1 hour, then quenched with water and extracted with ethyl acetate. The organic chase was washed with brine, dried over magnesium sulfate and evaporated in vacuo. The residue was chromatographed or silica gel eluting with a mixture of hexane and ethyl acetate (2:1) to give methyl 1-(2-chlorobenzyl)-2,3-diethylindole-6-carboxylate (42 mg) as colorless crystals.

mp: 86–88° C.; IR (KBr): 1710, 1240 cm$^{-1}$; NMR (CDCl$_3$, δ): 1.13 (3H, t, J=7 Hz), 1.30 (3H, t, J=7 Hz), 2.69 (2H, t, J=7 Hz), 2.79 (2H, q, J=7 Hz), 3.90 (3H, s), 5.44 (2H, s), 6.17 (1H, d, J=8 Hz), 7.00 (1H, t, J=8 Hz), 7.19 (1H, t, J=8 Hz), 7.42 (1H, d, J=7.5 Hz), 7.60 (1H, d, J=8 Hz), 7.80 (1H, d, J=8 Hz), 7.88 (1H, s); MASS (m/z): 356 (M$^+$+1).

EXAMPLE 31

Methyl 1-(2-chlorobenzyl)-2-propylindole-6-carboxylate 400 mg) was prepared from methyl 2-propylindole-6-carboxylate (350 mg) and 2-chlorobenzyl bromide (364 mg) in a similar manner to that of Example 1.

NMR (CDCl$_3$, δ): 0.99 (3H, t, J=8 Hz), 1.74 (2H, sextet, J=8 Hz), 2.60 (2H, t, J=8 Hz), 3.87 (3H, s), 5.43 (2H, s), 6.16 (1H, d, J=8 Hz), 6.43 (1H, s), 7.00 (1H, t, J=8 Hz), 7.18 (1H, t, J=8 Hz), 7.43 (1H, d, J=8 Hz), 7.60 (1H, d, J=8 Hz), 7.80 (1H, d, J=8 Hz), 7.90 (1H, s).

EXAMPLE 32

To a stirred solution of dimethylformamide (3 ml) and phosphorous oxychloride (0.056 ml) was added methyl 2-propylindole-6-carboxylate (187 mg), and the mixture was stirred at 0° C. for 20 minutes. The resulting mixture was poured into ammonia water (3 ml) and extracted with ethyl acetate. The combined organic phase was washed with brine, then dried over sodium sulfate and evaporated in vacuo. The residue was chromatographed on silica gel to give methyl 1-(2-chlorobenzyl)-3-formyl-2-propylindole-6-carboxylate (153 mg) as colorless oil.

NMR (CDCl$_3$, δ): 1.00 (3H, t, J=7 Hz), 1.66 (2H, m), 3.01 (2H, t, J=7 Hz), 3.50 (3H, s), 5.48 (2H, s), 6.29 (1H, d, J=8 Hz), 7.06 (1H, t, J=8 Hz), 7.24 (1H, t, J=8 Hz), 7.47 (1H, d, J=8 Hz), 7.91 (1H, s), 8.01 (1H, d, J=8 Hz), 8.37 (1H, d, J=8 Hz), >10 (1H, s).

EXAMPLE 33

Methyl 1-(2-chlorobenzyl)-3-phenylacetyl-2-propylindole-6-carboxylate (230 mg) was prepared from methyl 1-(2-chlorobenzyl)-2-propylindole-6-carboxylate (380 mg) and phenylacetyl chloride (189 mg) in a similar manner to that of Preparation 1 (5).

NMR (CDCl$_3$, δ): 0.97 (3H, t, J=8 Hz), 1.55–1.67 (2H, m), 3.02–3.07 (2H, m), 3.91 (3H, s), 4.42 (2H, s), 5.52 (2H, s), 6.24 (1H, d, J=8 Hz), 7.05 (1H, t, J=8 Hz), 7.20–7.40 (6H, m), 7.46 (1H, d, J=8 Hz), 7.97 (1H, s), 7.99 (1H, d, J=8 Hz), 8.11 (1H, d, J=8 Hz).

EXAMPLE 34

The following compounds described in 1) to 21) were prepared from the compound (I-1) obtained in Example 28, Example 29, Example 30, Example 32 or Example 33 in a similar manner to that of Example 2.

(1) 1-(2-Fluorobenzyl)-3-isobutyryl-2-propylindole-6-carboxylic acid mp: 212–213° C.; IR (KBr): 1685, 1650 cm$^{-1}$; NMR (CDCl$_3$, δ): 1.03 (3H, t, J=7 Hz), 1.30 (6H, d, J=7 Hz), 1.55–1.68 (2H, m), 3.09–3.14 (2H, m), 3.52–3.62 (1H, m), 5.50 (2H, s), 6.47 (1H, t, J=7.5 Hz), 6.97 (1H, t, J=7.5 Hz), 7.15 (1H, t, J=7.5 Hz), 7.24–7.30 (1H, m), 7.95–8.04 (2H, m), 8.08 (1H, s); MASS (m/z): 380 (M$^+$–1).

(2) 1-(2-Bromobenzyl)-3-isobutyryl-2-propylindole-6-carboxylic acid mp: 193–194° C.; IR (KBr): 1690, 1670 cm$^{-1}$; NMR (CDCl$_3$, δ): 1.03 (3H, t, J=7 Hz), 1.31 (6H, d, J=7 Hz), 1.57–1.65 (2H, m), 3.01–3.07 (2H, m), 3.52–3.61 (1H, m), 5.49 (2H, s), 6.22 (1H, t, J=7.5 Hz), 7.07–7.18 (2, m), 7.66 (1H, t, J=7.5 Hz), 7.97–8.01 (3H, m); MASS (m/z): 442 ($M^+$), 440 ($M^+$–2).

3) 1-(2-Iodobenzyl)-3-isobutyryl-2-propylindole-6-carboxylic acid mp: 210° C.; IR (KBr): 1710, 1640, 1435, 1200 $cm^{-1}$; NMR (CDCl$_3$, δ): 1.04 (3H, t, J=7 Hz), 1.31 (6H, d, J=7 Hz), 1.55–1.68 (2H, m), 3.00–3.06 (2H, m), 3.53–3.62 (1H, m), 5.38 (2H, s), 6.18 (1H, d, J=7.5 Hz), 6.99 (1H, t, J=7.5 Hz), 7.14 (1H, t, J=7.5 Hz), 7.94 (1H, d, J=7.5 Hz,), 7.97–8.03 (1H, m); MASS (m/z): 488 ($M^+$–1), 61 (bp).

(4) 3-Isobutyryl-1-(2-methylbenzyl)-2-propylindole-6-carboxylic acid mp: 186–188° C.; IR (KBr): 1690 $cm^{-1}$; NMR (CDCl$_3$, δ): 1.01 (3H, t, J=7 Hz), 1.31 (6H, d, J=7 Hz), 1.56–1.69 (2H, m), 2.50 (3H, s), 3.02–3.09 (2H, m), 3.52–3.67 (1H, m), 5.39 (2H, s), 6.17 (1H, d, J=7.5 Hz), 6.98 (1H, t, J=7.5 Hz), 7.17 (1H, t, J=7.5 Hz), 7.25 (1H, d, J=7.5 Hz), 7.97 (1H, s), 8.00 (2H, s); MASS (m/z): 378 ($M^+$+1), 76 (bp).

(5) 3-Isobutyryl-1-(2-methoxybenzyl)-2-propylindole-6-carboxylic acid mp: 190–191° C.; IR (KBr): 1685, 1650, 1250 $cm^{-1}$; NMR (CDCl$_3$, δ): 1.03 (3H, t, J=7 Hz), 1.30 (6H, d, J=7 Hz), 1.58–1.68 (2H, m), 3.07–3.13 (2H, m), 3.54–3.63 (1H, m), 3.93 (3H, s), 5.45 (2H, s), 6.30 (1H, d, J=7.5 Hz), 6.75 (1H, t, J=7.5 Hz), 6.94 (1H, d, J=7.5 Hz), 7.24 (1H, t, J=7.5 Hz), 7.94–8.02 (2H, m), 8.05 (1H, s); MASS (m/z): 394 ($M^+$+1), 76 (bp).

(6) 1-(2-Cyanobenzyl)-3-isobutyryl-2-propylindole-6-carboxylic acid mp: 213.5–215° C.; IR (KBr): 2220, 1717 $cm^{-1}$; NMR (CDCl$_3$, δ): 1.04 (3H, t, J=7 Hz), 1.31 (6H, d, J=7 Hz), 1.53–1.67 (2H, m), 3.04–3.09 (2H, m), 3.52–3.62 (1H, m), 5.69 (2H, s), 6.47–6.50 (1H, m), 7.39–7.44 (2H, m), 7.77–7.80 (1H, m), 7.99–8.04 (3H, m); MASS (m/z): 389 ($M^+$–1), 76 (bp).

(7) 3-Isobutyryl-1-(2-nitrobenzyl)-2-propylindole-6-carboxylic acid mp 214–215° C.; IR (KBr): 1695, 1655, 1545 $cm^{-1}$; NMR (CDCl$_3$, δ): 1.02 (3H, t, J=7 Hz), 1.32 (6H, d, J=7 Hz), 1.57–1.65 (2H, m), 3.03 (2H, t, J=7 Hz), 3.54–3.63 (1H, m), 5.89 (2H, s), 6.28 (1H, d, J=7.5 Hz), 7.39–7.51 (2H, m), 7.92 (1H, s), 8.02 (2H, s), 8.30 (1H, d, J=7.5 Hz); MASS (m/z) 409 ($M^+$+1).

(8) 1-(2,ε-Dichlorobenzyl)-3-isobutyryl-2-propylindole-6-carboxylic acid mp: 241.5–243° C. (dec.); IR (KBr): 1675, 1650 $cm^{-1}$; NMR (CDCl$_3$, δ): 0.99 (3H, t, J=7 Hz), 1.28 (6H, d, J=7 Hz), 1.39–1.52 (2H, m), 3.17–3.22 (2H, m), 3.50–3.59 (1H, m), 5.71 (2H, s), 7.24–7.28 (1H, M), 7.37–7.40 (2H, m), 7.94 (2H, q, J=7.5 Hz), 8.10 (1H, s). MASS (m/z) 432 ($M^+$+1), 76 (bp).

(9) 1-(2-Chloro-4-fluorobenzyl)-3-isobutyryl-2-propylindole-6-carboxylic acid mp: 243–244° C.; IR (KBr): 1676, 1648, 1491 $cm^{-1}$; NMR (CDCl$_3$, δ): 1.03 (3H, t, J=7 Hz), 1.30 (6H, d, J=7 Hz), 1.60 (2H, sextet, J=7 Hz), 3.01–3.07 (2H, m), 3.53–3.62 (1H, m), 5.49 (2H, s), 6.20–6.26 (1H, m), 6.79 (1H, ddd, J=7.5, 7.5, 1 Hz), 7.23 (1H, dd, J=7.5, 1 Hz), 7.96 (1H, s), 7.99 (1H, d, J=7.5 Hz); MASS (m/z): 414 ($M^+$–1).

(10) 1-(4-Bromo-2-fluorobenzyl)-3-isobutyryl-2-propylindole-6-carboxylic acid mp: 210–211° C.; IR (KBr): 1677, 1646, 1486 $cm^{-1}$; NMR (CDCl$_3$, δ): 1.04 (3H, t, J=7 Hz), 1.30 (6H, d, J=7 Hz), 1.55–1.67 (2H, m), 3.07–3.12 (2H, m), 3.52–3.60 (1H, m), 5.46 (2H, s), 6.32 (1H, t, J=7.5 Hz), 7.11 (1H, d, J=7.5 Hz), 7.35 (1H, d, J=7.5 Hz), 7.96–8.03 (3H, m); MASS (m/z) 460 ($M^+$), 458 ($M^+$–2).

(11) 3-Benzoyl-1-(2-chlorobenzyl)-2-propylindole-6-carboxylic acid

NMR (DMSO-d$_6$, δ): 0.95 (3H, t, J=8 Hz), 1.66 (2H, sextet, J=8 Hz), 2.98 (2H, t, J=8 Hz), 5.55 (2H, s), 6.35 (1H, dd, J=1, 8 Hz), 7.09 (1H, dt, J=1, 8 Hz), 7.20–7.27 (2H, m), 7.48 (1H, t, J=8 Hz), 7.57–7.62 (1H, m), 7.72–7.82 (3H, m), 7.98 (1H, s).

(12) 1-(2-Chlorobenzyl)-3-cyano-2-propylindole-6-carboxylic acid mp: 239.5–241° C.; IR (KBr): 2224, 1671, 1287, 1264 $cm^{-1}$; NMR (CDCl$_3$, δ): 1.00 (3H, t, J=7 Hz), 1.70 (2H, sextet, J=7 Hz), 2.89 (2H, t, J=7 Hz), 5.50 (2H, s), 5.25 (1H, d, J=7.5 Hz), 7.18 (1H, ddt, J=7.5, 7.5, 1 Hz), 7.25 (1H, ddd, J=7.5, 7.5, 1 Hz), 7.47 (1H, d, J=7.5 Hz), 7.78 (1H, dd, J=7.5, 1 Hz), 7.99 (1H, d, J=1 Hz), 8.01 (1H, d, J=7.5 Hz).

(13) 1-(2-Chlorobenzyl)-2-ethyl-3-isobutyrylindole-6-carboxylic acid NMR (CDCl$_3$, δ): 1.22 (3H, t, J=7 Hz), 1.31 (6H, d, J=7 Hz), 3.12 (2H, q, J=7 Hz), 3.57 (1H, m), 5.51 (2H, s), 6.23 (1H, d, J=8 Hz), 7.04 (1H, t, J=8 Hz), 7.22 (1H, t, J=8 Hz), 7.47 (1H, d, J=8 Hz), 7.95–9.05 (3H, m).

(14) 1-(2-Chlorobenzyl)-3-isobutyryl-2-methylindole-6-carboxylic acid

NMR (CDCl$_3$, δ): 1.31 (6H, d, J=7 Hz), 2.72 (3H, s), 3.56 (1H, m), 5.51 (2H, s), 6.25 (1H, d, J=8 Hz), 7.05 (1H, t, J=8 Hz), 7.23 (,1H, t, J=8 Hz), 7.46 (1H, d, J=8 Hz), 8.05 (3H, s).

(15) 1-(2-Chlorobenzyl)-3-isobutyryl-2-methoxymethylindole-6-carboxylic acid

NMR (CDCl$_3$, δ): 1.32 (6H, d, J=7 Hz), 3.35 (3H, s), 3.58 (1H, m), 4.94 (2H, s), 5.68 (2H, s), 6.28 (1H, d, J=8 Hz), 7.03 (1H, t, J=8 Hz), 7.20 (1H, t, J=8 Hz), 7.45 (1H, d, J=8 Hz), 8.0–8.05 (3H, m).

(16) 1-(2-Chlorobenzyl)-3-isobutyrylindole-6-carboxylic acid

NMR (CDCl$_3$, δ): 1.25 (6H, d, J=7 Hz), 3.30 (1H, m), 5.52 (2H, s), 6.79 (1H, d, J=8 Hz), 7.18 (1H, t, J=8 Hz), 7.28 (1H, t, J=8 Hz), 7.47 (1H, d, J=8 Hz), 7.91 (1H, s), 8.03 (1H, d, J=8 Hz), 8.12 (1H, s), 8.48 (1H, d, J=8 Hz).

(17) 3-Isobutyryl-2-propyl-1-(2-pyridylmethyl)indole-6-carboxylic acid

NMR (DMSO-d$_6$, δ): 0.92 (3H, t, J=7 Hz), 1.16 (6H, d, J=7 Hz), 1.46 (2H, sextet, J=7 Hz), 3.12–3.17 (2H, m), 3.52 (2H, septet, J=7 Hz), 5.72 (2H, s), 7.16 (1H, d, J=8 Hz), 7.29 (1H, dd, J=5, 8 Hz), 7.76 (1H, t, J=8 Hz), 7.81 (1H, d, J=8 Hz), 7.96 (1H, t, J=8 Hz), 8.06 (1H, s), 8.48 (1H, d, J=5 Hz).

(18) 1-(2-Chlorobenzyl)-2,3-diethylindole-6-carboxylic acid mp: 258–259° C. (dec.); IR (KBr): 1675, 1290 $cm^{-1}$; NMR (CDCl$_3$, δ): 1.14 (3H, t, J=7 Hz), 1.30 (3H, t, J=7 Hz), 2.71 (2H, q, J=7 Hz), 2.80 (2H, q, J=7 Hz), 5.45 (2H, s), 6.18 (1H, d, J=7.5 Hz), 7.00 (1H, t, J=7.5 Hz), 7.19 (1H, t, J=7.5 Hz), 7.42 (1H, d, J=7.5 Hz), 7.62 (1H, d, J=7.5 Hz), 7.84 (1H, d, J=7.5 Hz), 7.91 (1H, s); MASS (m/z) 340 ($M^+$–1).

(19) 1-(2-Chlorobenzyl)-3-formyl-2-propylindole-6-carboxylic acid

NMR (CDCl$_3$, δ): 1.01 (3H, t, J=7 Hz), 1.67 (2H, m), 3.03 (2H, t, J=7 Hz), 5.50 (2H, s), 6.40 (1H, d, J=8 Hz), 7.08 (1H, t, J=8 Hz), 7.24 (1H, t, J=8 Hz), 7.48 )(1H, d, J=8 Hz), 7.98 (1H, s), 8.07 (1H, d, J=8 Hz), 8.40 (1H, d, J=8 Hz).

(20) (2-Chlorobenzyl)-3-phenylacetyl-2-propylindole-6-carboxylic acid

NMR (DMSO-d$_6$, δ): 0.90 (3H, t, J=8 Hz), 1.45 (2H, sextet, J=8 Hz), 3.04–3.08 (2H, m), 4.43 (2H, s), 5.68 (2H, s), 6.27 (1, d, J=8 Hz), 7.18 (1H, t, J=8 Hz), 7.23–7.35 )6H, m), 7.58 (1H, d, J=8 Hz), 7.85 (1H, d, J=8 Hz), 7.98 (1H, s), 8.19 (1H, d, J=8 Hz).

(21) 3-Acetyl-1-(6-chloro-3,4-methylenedioxybenzyl)-2-proponylindole-6-carboxylic acid mp: 238–239° C.; NMR (CDCl$_3$–CD$_3$OD=1:1, δ): 1.06 (3H, t, J=8 Hz), 1.65 (2H, sextet, J=8 Hz), 2.76 (3H, s), 3.08–3.14 (2H, m), 5.48 (2H, s), 5.74 (1H, s) 5.92 (2H, s), 6.96 (1H, s), 7.99 (1H, d, J=8 Hz), 8.02 (1H, s), 8.08 (1H, d, J=8 Hz).

EXAMPLE 35

Methyl 3-acetyl-1-(2-chlorobenzyl)-2-ethylindole-6-carboxylate (170 mg) was prepared from methyl 3-acetyl-2-ethylindole-6-carboxylate (100 mg) and 2-chlorobenzyl bromide (0.06 ml) in a similar manner to that of Example 1.

This product was used immediately without purification in the below-mentioned Example 36.

EXAMPLE 36

3-Acetyl-(2-chlorobenzyl)-2-ethylindole-6-carboxylic acid (137 mg) was prepared from methyl 3-acetyl-1-(2-chlorobenzyl)-2-ethylindole-6-carboxylate (170 mg) in a similar manner to that of Example 2.

NMR (DMSO-d$_6$, δ): 1.11 (3H, t, J=7 Hz), 2.67 (3H, s), 3.11 (2H, q, J=7 Hz), 5.68 (2H, s), 6.26 (1H, d, J=8 Hz), 7.19 (1H, t, J=8 Hz), 7.32 (1H, t, J=8 Hz), 7.58 (1H, d, J=8 Hz), 7.83 (1H, d, J=8 Hz), 7.94 (1H, s), 8.13 (1H, d, J=8 Hz).

EXAMPLE 37

The following compounds described in 1) to 19) were prepared from the compound (I-2) obtained in Example 34 and Example 36 in a similar manner to that of Example 3.

(1) 1-(2-Fluorobenzyl)-3-isobutyryl-2-propylindole-6-carboxyamide mp: 198° C.; IR (KBr): 3200, 1650, 1610 cm$^{-1}$; NMR (CDCl$_3$, δ): 1.03 (3H, t, J=7 Hz), 1.30 (6H, d, J=7 Hz), 1.55–1.64 (2H, m), 3.06–3.12 (2H, m), 3.50–3.60 (1H, m), 5.50 (2H, s), 6.42 (1H, t, J=7.5 Hz), 6.95 (2H, t, J=7.5 Hz), 7.09–7.17 (1H, m), 7.22–7.28 (1H, m), 7.61 (1H, t, J=7.5 Hz), 7.90 (1H, s), 7.96 (1H, t, J=7.5 Hz); MASS (m/z): 381 (M$^+$+1).

(2) 1-(2-Bromobenzyl)-3-isobutyryl-2-propylindole-6-carboxamide mp: 173–174° C.; IR (KBr): 3400, 1660, 1630 cm$^{-1}$; NMR (CDCl$_3$, δ): 1.03 (3H, t, J=7 Hz), 1.30 (6H, d, J=7 Hz), 1.57–1.68 (2H, m), 3.00–3.06 (2H, m), 3.51–3.61 (1H, m), 5.46 (2H, s), 6.20 (1H, t, J=7.5 Hz), 7.05–7.18 (2H, m), 7.60–7.66 (1H, m), 7.83 (1H, s), 7.99 (1H, t, J=7.5 Hz); MASS (m/z): 443 (M$^+$+2), 441 (M$^+$), 76 (bp).

(3) 1-(2-Iodobenzyl)-3-isobutyryl-2-propylindole-6-carboxamide mz : 186–187° C.; IR (KBr): 3400, 1665, 1640 cm$^{-1}$; NMR (CDCl$_3$, δ): 1.03 (3H, t, J=7 Hz), 1.30 (6H, d, J=7 Hz), 1.54–1.67 (2H, m), 2.99–3.05 (2H, m), 3.51–3.60 (1H, m), 5.39 (2H, s), 6.15 (1H, d, J=7.5 Hz), 6.99 (1H, t, J=7.5 Hz), 7.11 (1H, t, J=7.5 Hz), 7.64 (1H, d, J=7.5 Hz), 7.82 (1H, s), 7.92 (1H, d, J=7 Hz), 7.99 (1H, s); MASS (m/z): 489 (M$^+$+1), 76 (bp).

(4) 3-Isobutyryl-1-(2-methylbenzyl)-2-propylindole-6-carboxamide mp: 190–191° C.; IR (KBr): 3395, 1650, 1625, 1410 cm$^{-1}$; NMR (CDCl$_3$, δ) 1.00 (3H, 1, J=7 Hz), 1.31 (6H, d, J=7 Hz), 1.54–1.68 (2H, m), 2.49 (3H, s), 3.00–3.07 (2H, m), 3.52–3.61 (1H, m), 5.38 (2H, s), 6.14 (1H, J=7.5 Hz), 6.98 (1H, t, J=7.5 Hz), 7.17 (1H, t, J=7.5 Hz), 7.24 (1H, d, J=7.5 Hz), 7.60 (1H, d, J=7.5 Hz), 7.82 (1H, s), 7.99 (1H, d, J=7.5 Hz); MASS (m/z): 377 (M$^+$+1), 76 (bp).

(5) 3-Isobutyryl-1-(2-methoxybenzyl)-2-propylindole-6-carboxamide mp: 174–175° C.; IR (KBr): 3370, 1655, 1650, 1625cm$^{-1}$; NMR (CDCl$_3$, δ): 1.01 (3H, t, J=7 Hz), 1.30 (6H, d, J=7 Hz), 1.57–1.69 (2H, m), 3.05–3.10 (2H, m), 3.52–3.61 (1H, m), 3.97 (3H, s), 5.43 (2H, s), 6.24 (1H, d, J=7.5 Hz), 6.74 (2H, t, J=7.5 Hz), 6.93 (1H, d, J=7.5 Hz), 7.24 (1H, t, J=7.5 Hz), 7.59 (1H, d, J=7.5 Hz), 7.88 (1H, s), 7.97 (1H, d, J=7.5 Hz); MASS (m/z): 393 (M$^+$+1), 76 (bp).

(6) 1-(2-Cyanobenzyl)-3-isobutyryl-1-propylindole-6-carboxamide mp: 143–144° C.; IR (KBr): 3377, 3190, 2227, 1645 cm$^{-1}$; NMR (CDCl$_3$, δ): 1.04 (3H, t, J=7 Hz), 1.30 (6H, d, J=7 Hz), 1.52–1.65 (2H, m), 3.02–3.08 (2H, m), 3.50–3.59 (1H, m), 5.68 (2H, s), 6.45–6.49 (1H, m), 7.38–7.43 (2H, m), 7.65 (1H, d, J=7.5 Hz), 7.74–7.78 (1H, m), 7.87 (1H, s), 7.99 (1H, d, J=7.5 Hz); MASS (m/z): 388 (M$^+$+1), 62 (bp).

(7) 3-Isobutyryl-1-(2-nitrobenzyl)-2-propylindole-6-carboxamide mp: 181–182° C.; IR (KBr): 3190, 1670, 1610, 1535, 1400 cm$^{-1}$; NMR (CDCl$_3$, δ): 1.00 (3H, t, J=7 Hz), 1.32 (6H, d, J=7 Hz), 1.58–1.67 (2H, m), 3.02 (2H, t, J=7 Hz), 3.52–3.61 (1H, m), 5.89 (2H, s), 6.27 (1H, d, J=7.5 Hz), 7.39–7.50 (2H, m), 7.63 (1H, d, J=7.5 Hz), 7.80 (1H, s), 7.99 (1H, d, J=7.5 Hz), 8.28 (1H, d, J=7.5 Hz); MASS (m/z): 408 (M$^+$+1), 76 (bp).

(8) 1-(2,6-Dichlorobenzyl)-3-isobutyryl-2-propylindole-6-carboxamide mp: 207.5–209° C.; IR (KBr): 3395, 1650, 1615 cm$^{-1}$; NMR (CDCl$_3$, δ): 0.98 (3H, t, J=7 Hz), 1.28 (6H, d, J=7 Hz), 1.39–1.50 (2H, m), 3.16–3.21 (2H, m), 3.49–3.58 (1H, m,), 5.70 (2H, s), 7.22–7.25 (1H, m), 7.35–7.39 (2H, m)), 7.60 (1H, d, J=7.5 Hz), 7.86–7.90 (2H, m), 7.99 (1H, d, J=7.5 Hz); MASS (m/z): 431 (M$^+$+1), 76 (bp).

(9) 1-(2-Chloro-4-fluorobenzyl)-3-isobutyryl-2-propylindole-6-carboxamide mp: 192–193° C.; IR (KBr): 3336, 3180, 1650, 1494, 1411 cm$^{-1}$; NMR (CDCl$_3$, δ): 1.03 (3H, t, J=7 Hz), 1.30 (6H, d, J=7 Hz), 1.53–1.65 (2H, m), 3.01–3.07 (2H, m), 3.50–3.60 (1H, m), 5.47 (2H, s), 6.20 (1H, dd, J=8, 7.5 Hz), 6.78 (1H, ddd, J=7.5, 7.5, 1 Hz), 7.23 (1H, dd, J=8, 1 Hz), 7.63 (1H, d, J=7.5 Hz), 7.85 (1H, s), 7.99 (1H, d, J=8 Hz); MASS (m/z): 415 (M$^+$+1), 76 (bp).

(10) 1-(4-Bromo-2-fluorobenzyl)-3-isobutyryl-2-propylindole-6-carboxamide mp: 197–198.5° C.; IR (KBr): 3377, 3189, 1652, 1617, 1487, 1408 cm$^{-1}$; NMR (CDCl$_3$, δ): 1.04 (3H, t, J=7 Hz), 1.30 (6H, d, J=7 Hz), 1.53–1.64 (2H, m), 3.05–3.11 (2H, m), 3.48–3.60 (1H, m), 5.44 (2H, s), 6.29 (1H, t, J=7.5 Hz), 7.09 (1H, t, J=7.5 Hz), 7.33 (1H, dd, J=7.5, 1 Hz), 7.62 (1H, d, J=7.5 Hz), 7.90 (1H, d, J=1 Hz), 7.97 (1H, d, J=7.5 Hz); MASS (m/z): 461 (M$^+$+2), 459 (M$^+$), 76 (bp).

(11) 1-(2-Chlorobenzyl-3-cyano-2-propylindole-6-carboxamide mp: 222–223.5° C.; IR (KBr): 3443, 3183, 2215, 1679, 1394 cm$^{-1}$; NMR (CDCl$_3$, δ): 1.02 (3H, t, J=7 Hz), 1.70 (2H, sextet, J=7 Hz), 2.89 (2H, t, J=7.5 Hz), 5.50 (2H, s), 6.21 (1H, d, J=7.5 Hz), 7.08 (1H, t, J=7.5 Hz), 7.24 (1H, ddd, J=7.5, 7.5, 1 Hz), 7.47 (1H, d, J=7.5 Hz), 7.61 (1H, d, J=7.5 Hz), 7.77 (1H, d, J=7.5 Hz), 7.89 (1H, d, J=1 Hz); MASS (m/z): 352 (M$^+$+1), 76 (bp).

(12) 1-(2-Chlorobenzyl)-2-ethyl-3-isobutyrylindole-6-carboxamide mp: 178–180.5° C.; NMR (CDCl$_3$, δ): 1.22 (3H, t, J=7 Hz), 1.30 (6H, d, J=7 Hz), 3.09 (2H, q, J=7 Hz), 3.56 (1H, m), 5.51 (2H, s), 6.22 (1H, d, J=8 Hz), 7.04 (1H, t, J=8 Hz), 7.22 (1H, t, J=8 Hz), 7.44 (1H, d, J=8 Hz), 7.63 (1H, d, J=8 Hz), 7.82 (1H, s), 7.98 (1H, d, J=8 Hz).

(13) 1-(2-Chlorobenzyl)-3-isobutyryl-2-methylindole-6-carboxamide mp: 212–215° C.; NMR (CDCl$_3$, δ): 1.30 (6H, d, J=7 Hz), 2.69 (3H, s), 3.53 (1H, m), 5.48 (2H, s), 6.21 (1H, d, J=8 Hz), 7.04 (1H, t, J=8 Hz), 7.23 (1H, t, J=8 Hz), 7.45 (1H, d, J=8 Hz), 7.62 (1H, d, J=8 Hz), 7.87 (1H, s), 8.03 (1H, d, J=8 Hz).

(14) 1-(2-Chlorobenzyl)-3-isobutyryl-2-methoxymethylindole-6-carboxamide mp: 204–206° C.; NMR (CDCl$_3$, δ): 1.32 (6H, d, J=7 Hz), 3.34 (3H, s), 3.57 (1H, m), 4.92 (2H, s), 5.65 (2H, s), 6.24 (1H, d, J=8 Hz), 7.03 (1H, t, J=8 Hz), 7.21 (1H, t, J=8 Hz), 7.44 (1H, d, J=8 Hz), 7.67 (1H, d, J=8 Hz), 7.83 (1H, s), 8.02 (1H, d, J=8 Hz).

(15) 1-(2-Chlorobenzyl)-3-isobutyrylindole-6-carboxamide mp: 235–237° C.; NMR (DMSO-d$_6$, δ): 1.16 (6H, d, J=7 Hz), 3.40 (1H, m), 5.67 (2H, s), 6.70 (1H, d, J=8 Hz), 7.2–7.4 (3H, m), 7.56 (1H, d, J=8 Hz), 7.80 (1H, d, J=8 Hz), 7.96 (1H, br s), 6.04 (1H, s), 8.27 (1H, d, J=8 Hz), 8.64 (1H, s).

(16) 3-Isobutyryl-2-propyl-1-(2-pyridylmethyl)indole-6-carboxamide

NMR (DMSO-d$_6$, δ): 0.90 (3H, t, J=7 Hz), 1.17 (6H, d, J=7 Hz), 1.46 (2H, sextet, J=7 Hz), 3.08–3.15 (2H, m), 3.52 (2H, septet, J=7 Hz), 5.66 (2H, s), 7.08 (1H, d, J=8 Hz), 7.28–7.32 (2H, m), 7.78 (1H, d, J=8 Hz), 7.92 (1H, d, J=8 Hz), 8.09 (1H, s), 8.50 (1H, d, J=5 Hz).

(17) 1-(2-Chlorobenzyl)-2,3-diethylindole-6-carboxamide mp: 185–187.5° C.; IR (KBr): 3400, 1650, 1610 cm$^{-1}$; NMR (CDCl$_3$, δ) 1.15 (3H, t, J=7 Hz), 1.29 (3H, t, J=7 Hz), 2.69 (2H, q, J=7 Hz), 2.80 (2H, q, J=7 Hz), 5.44 (2H, s), 6.17 (1H, d, J=7.5 Hz), 7.00 (1H, t, J=7.5 Hz), 7.18 (1H, t, J=7.5 Hz), 7.41 (1H, d, J=7.5 Hz), 7.47 (1H, d, J=7.5 Hz), 7.62 (1H, d, J=7.5 Hz), 7.76 (1H, s); MASS (m/z): 341 (M$^+$+1), 76 (bp).

(18) 3-Acetyl-1-(2-chlorobenzyl)-2-ethylindole-6-carboxamide mp: 217–220° C.; NMR (CDCl$_3$, δ) 1.22 (3H, t, J=7 Hz), 2.73 (3H, s), 3.12 (2H, q, J=7 Hz), 5.49 (2H, s), 6.20 (1H, d, J=8 Hz), 7.02 (1H, t, J=8 Hz), 7.22 (1H, t, J=8 Hz), 7.43 (1H, d, J=8 Hz), 7.63 (1H, d, J=8 Hz), 7.83 (1H, s), 8.08 (1H, d, J=8 Hz).

(19) 1-(2-Chlorobenzyl)-3-formyl-2-propylindole-6-carboxamide mp: 245° C. (dec.); NMR (DMSO-D$_6$, δ): 0.92 (3H, t, J=7 Hz), 1.63 (2H, m), 3.11 (2H, t, J=7 Hz), 5.64 (2H, s), 6.32 (1H, d, J=8 Hz), 7.21 (1H, t, J=8 Hz), 7.25–7.35 (2H, m), 7.60 (1H, d, J=8 Hz), 7.83 (1H, d, J=8 Hz), 7.95 (1H, d, J=8 Hz), 7.97 (1H, s), 8.21 (1H, d, J=8 Hz), >10 (1H, s).

EXAMPLE 38

The following compounds described in 1) to 3) were prepared from the compound (I-2) obtained in Example 34-11), Example 34-20) or Example 34-21) in a similar manner to that of Example 6.

(1) 3-Benzoyl-1-(2-chlorobenzyl)-2-propylindole-6-carboxamide

NMR (DMSO-d$_6$, δ): 0.78 (3H, t, J=8 Hz), 1.46 (2H, sextet, J=8 Hz), 2.88 (2H, t, J=8 Hz), 5.66 (2H, s), 6.33 (1H, dd, J=1, 8 Hz), 7.08 (1H, dt, J=1, 8 Hz), 7.20–7.38 (3H, m), 7.52–7.72 (7H, m), 7.88 (1H, br s), 7.99 (1H, s).

(2) 1-(2-Chlorobenzyl)-3-phenylacetyl-2-propylindole-6-carboxamide

NMR (DMSO-d$_6$, δ): 0.88 (3H, t, J=8 Hz), 1.47 (2H, sextet, J=8 Hz), 2.98–3.03 (2H, m), 4.42 (2H, s), 5.63 (2H, s), 6.20 (1H, d, J=8 Hz), 7.17 (1H, t, J=8 Hz), 7.24–7.35 (6H, m), 7.57 (1H, d, J=8 Hz), 7.82 (1H, d, J=8 Hz), 7.95 (1H, br s), 8.02 (1H, s), 8.14 (1H, d, J=8 Hz).

(3) 3-Acetyl-1-(6-chloro-3,4-methylenedioxybenzyl)-2-propylindole-6-carboxamide mp: 220–223° C.; NMR (DMSO-d$_6$, δ): 0.94 (3H, t, J=8 Hz), 1.50 (2H, sextet, J=8 Hz), 2.65 (3H, s), 3.02–3.06 (2H, m), 5.52 (2H, s), 5.66 (1H, s), 5.99 (2H, s), 7.23 (1H, s), 7.86 (1H, d, J=8 Hz), 8.01 (1H, s), 8.05 (1H, d, J=8 Hz).

EXAMPLE 39

To a solution of 3-isobutyryl-2-propyl-1-(2-pyridylmethyl)indole-6-carboxamide (80 mg) in chloroform (2 ml) was added 1M solution of hydrogen chloride in methanol (1 ml) at 25° C., and the mixture was stirred for 15 minutes. After evaporation or solvent, the residue was crystallized from a mixture of ethanol and ethyl acetate to give 3-isobutyryl-2-propyl-1-(2-pyridylmethyl)indole-6-carboxamide hydrochloride (80 mg) as colorless crystals.

mp: 230–235° C.; NMR (DMSO-d$_6$, δ): 0.92 (3H, t, J=7 Hz), 1.17 (6H, d, J=7 Hz), 1.45 (2H, sextet, J=7 Hz), 3.08–3.14 (2H, m), 3.52 (2H, septet, J=7 Hz), 5.74 (2H, s), 7.09 (1H, d, J=8 Hz), 7.46 (1H, dd, J=5, 8 Hz), 7.79 (1H, d, J=8 Hz), 7.90 (1H, d, J=8 Hz) 7.92 (1H, t, J=8 Hz), 8.12 (1H, s), 8.62 (1H, d, J=5 Hz).

EXAMPLE 40

1-(2-carboxybenzyl)-3-isobutyryl-2-propylindole-6-carboxamide (242 mg) was prepared from 3-isobutyryl-1-(2-methoxycarbonylbenzyl)-2-propylindole-6-carboxamide (265 mg) in a similar manner to that of Example 2.

mp: 268–269° C. (dec.); IR (KBr): 1740, 1690, 1625, 1620 cm$^{-1}$; NMR (DMSO-d$_6$, δ) 0.90 (3H, t, J=7 Hz), 1.19 (6H, d, J=7 Hz), 1.42–1.51 (2H, m), 2.94–3.06 (2H, m), 3.50–3.60 (1H, m), 5.96 (2H, s), 6.06–6.10 (1H, m), 7.37–7.40 (2H, m), 7.79–7.82 (1H, m), 7.91–7.95 (1H, m), 7.99 (1H, s), 8.03–8.06 (1H, m); MASS (m/z) 407 (M$^+$+1), 86 (bp).

EXAMPLE 41

1-(2-Carbamoylbenzyl)-3-isobutyryl-2-propylindole-6-carboxamide (102 mg) was prepared from 1-(2-carboxybenzyl)-3-isobutyryl-2-propylindole-6-carboxamide (164 mg) in a similar manner to that of Example 3.

mp: 273–274° C.; IR (KBr): 1690 cm$^{-1}$; NMR (DMSO-d$_6$, δ): 0.90 (3H, t, J=7 Hz), 1.19 (6H, d, J=7 Hz), 1.41–1.5 (2H, m), 2.94–2.99 (2H, m), 3.48–3.57 (1H, m), 5.79 (2H, s), 6.17 (1H, d, J=7.5 Hz), 7.22–7.35 (3H, m), 7.61–7.68 (2H, m), 7.80 (1H, d, J=7.5 Hz), 7.92–7.97 (2H, m), 8.04 (1H, s), 8.13 (1H, s); MASS (m/z): 406 (M$^+$+1), 87 (bp).

EXAMPLE 42

To a solution phosphorus oxychloride (0.031 ml) in dimethylformamide (1.2 ml) was added 1-(2-chlorobenzyl)-

2-ethyl-3-propionylindole-6-carboxamide (112 mg) at 0° C., and the mixture was stirred for 15 minutes. The resulting mixture was poured into ammonia water and ice, and then extracted with ethyl acetate. The organic phase was washed with brine, dried over sodium sulfate and evaporated in vacuo. The residue was triturated with a mixture of hexane and isopropyl ether to give 1-(2-chlorobenzyl)-2-ethyl-3-propionylindole-6-carbonitrile (93 mg) as a solid.

mp: 115–118° C.; NMR (CDCl$_3$, δ): 1.25 (3H, t, J=7 Hz), 1.30 (3H, t, J=7 Hz), 3.09 (2H, q, J=7 Hz), 3.17 (2H, q, J=7 Hz), 5.47 (2H, s), 6.21 (1H, d, J=8 Hz), 7.07 (1H, t, J=8 Hz), 7.25 (1H, t, J=8 Hz), 7.45–7.55 (3H, m), 8.09 (1, d, J=7 Hz).

EXAMPLE 43

1-(2-Chlorobenzyl)-2-ethyl-3-isobutyrylindole-6-carbonitrile (239 mg) was prepared from 1-(2-chlorobenzyl)-2-ethyl-3-isobutyrylindole-6-carboxamide (280 mg) in a similar manner to that of Example 42.

mp: 132–134° C.; NMR (CDCl$_3$, δ): 1.23 (3H, t, J=7 Hz), 1.31 (6H, d, J=7 Hz), 3.13 (2H, q, J=7 Hz), 3.50 (1H, m), 5.48 (2H, s), 6.22 (1H, d, J=8 Hz), 7.07 (1H, t, J=8 Hz), 7.27 (1H, t, J=8 Hz), 7.27 (1H, d, J=8 Hz), 7.44–7.53 (2H, m), 8.02 (1H, d, J=8 Hz).

EXAMPLE 44

To a solution of 1-(2-chlorobenzyl)-2-ethyl-3-propionylindole-6-carbonitrile (107 mg) in xylene (5 ml) was added trimethyltin azide (190 mg), and the mixture was stirred at 120° C. for 14 hours. The resulting mixture was poured into 1N HCl and extracted with ethyl acetate. The organic phase was washed with brine, dried over sodium sulfate and evaporated in vacuo. The residue was chromatographed on silica gel eluting with 20% methanol in chloroform to give 1-(2-chlorobenzyl)-2-ethyl-3-propionyl-6-(1H-tetrazol-5-yl)indole (77 mg) as a solid.

mp: 178–181° C.; NMR (CDCl$_3$, δ) 1.18 (3H, t, J=7 Hz), 1.34 (3H, t, J=7 Hz), 3.0–3.15 (4H, m), 5.42 (2H, s), 6.21 (1H, d, J=8 Hz), 6.94 (1H, t, J=8 Hz), 7.13 (1H, t, J=8 Hz), 7.33 (1H, d, J=8 Hz), 8.03 (1H, d, J=8 Hz), 8.05 (1H, s), 8.25 (1H, d, J=8 Hz).

EXAMPLE 45

1-(2-chlorobenzyl)-2-ethyl-3-isobutyryl-6-(1H-tetrazol-5-yl)-indole (109 mg) was prepared from 1-(2-chlorobenzyl)-2-ethyl-3-isobutyrylindole-6-carbonitrile (130 mg) in a similar manner to that of Example 44.

mp: 160–163° C.; NMR (CDCl$_3$, δ): 1.18 (3H, t, J=7 Hz), 1.31 (6H, d, J=7 Hz), 3.04 (2H, q, J=7 Hz), 3.52 (1H, m), 5.37 (2H, s), 6.20 (1H, d, J=8 Hz), 6.94 (1H, t, J=8 Hz), 7.11 (1H, t, J=8 Hz), 7.33 (1H, d, J=8 Hz), 8.00 (1H, d, J=8 Hz), 8.02 (1H, s), 8.13 (1H, d, J=8 Hz).

EXAMPLE 46

The following compounds described in (1) to 2) were prepared in similar manner to that of Preparation 30.

(1) Methyl 2-(3-carboxypropyl)-1-(2-chlorobenzyl)-6-carboxylate

NMR (CDCl$_3$, δ): 2.04 (2H, m), 2.45 (2H, t, J=7 Hz), 2.73 (2H, t, J=7 Hz), 3.89 (3H, s), 5.44 (2H, s), 6.14 (1H, d, J=8 Hz), 6.47 (1H, s), 7.01 (1H, t, J=8 Hz), 7.18 (1H, t, J=8 Hz), 7.44 (1H, d, J=8 Hz), 7.62 (1H, d, J=8 Hz), 7.83 (1H, d, J=8 Hz), 7.93 (1H, s).

(2) 2-(2-Carboxyethyl)-1-(2-chlorobenzyl)indole-6-carboxylate

NMR; (CDCl$_3$, δ): 2.76 (2H, t, J=7 Hz), 2.96 (2H, t, J=7 Hz), 3.88 (3H, s, 5.46 (2H, s), 6.16 (1H, d, J=8 Hz), 6.46 (1H, s), 7.01 (1H, t, J=8 Hz), 7.20 (1H, J=8 Hz), 7.43 (1H, d, J=8 Hz), 7.62 (1H, d, J=8 Hz), 7.82 (1H, d, J=8 Hz), 7.93 (1H, s).

PREPARATION 47

The Following compounds described in (1) to (2) were prepared in a similar manner to that of Preparation 31.

(1) Methyl 9-(2-chlorobenzyl)-5-oxo-5,6,7,8-tetrahydrocarbazole-2-carboxylate

NMR (CDCl$_3$, δ) 2.24 (2H, m), 2.62 (2H, t, J=7 Hz), 2.86 (2H, t, J=7 Hz), 3.90 (3H, s), 5.47 (2H, s), 6.34 (1H, d, J=8 Hz), 7.09 (1H, t, J=8 Hz), 7.25 (1H, t, J=8 Hz), 7.47 (1H, d, J=8 Hz), 7.97 (1H, s), 7.99 (1H, d, J=8 Hz), 8.33 (1H, d, J=8 Hz).

(2) Methyl 4-(2-chlorobenzyl)-1-oxo-1,2,3,4-tetrahydrocyclopent[b]indole-6-carboxylate NMR (CDCl$_3$, δ): 2.9–3.15 (4H, m), 3.91 (3H, s), 5.46 (2H, s), 6.66 (1H, d, J=8 Hz), 7.17 (1H, t, J=8 Hz), 7.29 (1H, t, J=8 Hz), 7.48 (1H , d, J=8 Hz), 7.94–8.06 (3H, m).

EXAMPLE 48

The following compounds described in (1) to (2) were prepared in a similar manner to that of Preparation 1 (5).

(1) Methyl 3-chloroacetyl-1-(2-chlorobenzyl)-2-propylindole-6-carboxylate mp: 143–145° C.; IR (KBr): 1722, 1666 cm$^{-1}$; NMR (CDCl$_3$, δ): 1.03 (3H, t, J=7 Hz), 1.55–1.66 (2H, m), 3.05–3.10 (2H, m), 3.91 (3H, s), 4.82 (2H, s), 5.53 (2H, s), 6.25 (1H, d, J=7.5 Hz), 7.05 (1H, t, J=7.5 Hz), 7.20–7.25 (1H, m), 7.49 (1H , d, J=7.5 Hz), 7.88 (1H, d, J=8 Hz), 7.98 (1H, s), 8.00 (1H, d, J=8 Hz); MASS (m/z): 418 (M$^+$–1), 76 (bp).

(2) 1-(2-Chlorobenzyl)-3-crotonoyl-2-propylindole-6-carboxamide mp: 185.5–186.5° C.; IR (KBr): 1648, 1614, 1443, 1414, 1388 cm$^{-1}$; NMR (CDCl$_3$, δ) 1.00 (3H, t, J=7 Hz), 1.64 (2H, sextet, J=7 Hz), 2.04 (3H, d, J=7 Hz), 3.00 (2H, t, J=7 Hz), 5.51 (2H, s), 6.24 (1H, d, J=8 Hz), 6.92 (1H, d, J=15 Hz), 7.00–7.06 (2H, m), 7.23 (1H, t, J=8 Hz), 7.46 (1H, d, J=7.5 Hz), 7.60 (1H, d, J=7.5 Hz), 7.83 (1H, s), 7.99 (1H, d, J=8 Hz); MASS (m/z): 395 (M$^+$+1), 74 (bp).

EXAMPLE 49

A mixture of methyl 3-chloroacetyl-1-(2-chlorobenzyl)-2-propylindole-6-carboxylate (123 mg) and morpholine (1 ml) was stirred at 50° C. for 2.5 hours. After cooled to 20° C., the reaction mixture was extracted with ethyl acetate. The organic phase was washed with 1N hydrochloric acid and water, dried over magnesium sulfate and evaporated in vacuo. The residue was chromatographed on silica gel eluting with a mixture of ethyl acetate and hexane (1:2) to give methyl 1-(2-chlorobenzyl)-3-morpholineacetyl-2-propylindole-6-carboxylate (94 mg) as colorless amorphous.

IR (KBr): 1712, 1657 cm$^{-1}$; NMR (CDCl$_3$, δ): 1.01 (3H, t, J=7 Hz), 1.60–1.65 (2H, m), 2.70–2.75 (4H, m), 3.06 (2H, t, J=7 Hz), 3.84 (4H, t, J=7 Hz), 3.90 (2H, s), 3.92 (3H, s), 5.52 (2H, s), 6.24 (1H, d, J=7.5 Hz), 7.06 (1H, t, J=7.5 Hz), 7.24 (1H, t, J=7.5 Hz), 7.48 (1H, d, J=7.5 Hz), 7.94–7.98 (3H, m); MASS (m/z): 469 (M$^+$+1).

EXAMPLE 50

To a mixture of methyl 1-(2-chlorobenzyl)-3-formyl-2-propylindole-6-carboxylate (263 mg), 2-methyl-2-butene (220 mg) and sodium dihydrogenphoshate (128 mg) in a mixture of tert-butanol (7 ml) and water (1.3 ml) was added sodium chlorite (219 mg) at 20° C. The reaction mixture was stirred at 40° C. for 2 hours. The reaction mixture was acidified with 1N hydrochloric acid at 0° C. and extracted with chloroform three times. The organic phase was dried over sodium sulfate and evaporated in vacuo. The residue was chromatographed on silica gel eluting with a mixture of ethyl acetate and hexane (1:2) to give 1-(2-chlorobenzyl)-6-methoxycarbonyl-2-propylindole-3-carboxylic acid (94 mg) as pale yellow crystals.

mp: 229–231° C. (dec.); Ir (KBr): 1715, 1658, 1441, 1275, 1227 cm$^{-1}$; NMR (CDCl$_3$, δ): 1.05 (3H, t, J=7 Hz), 1.60–1.70 (2H, m), 3.10–3.18 (2H, m), 3.93 (3H, s), 5.54 (2H, s), 6.78 (1H, d, J=7.5 Hz), 7.06 (1H, t, J=7.5 Hz), 7.21–7.25 (1H, m), 7.49 (1H, d, J=7.5 Hz), 7.95 (1H, s), 7.99 (1H, d, J=8 Hz), 8.33 (1H, d, J=8 Hz); MASS (m/z): 384 (M$^+$–1), 77 (bp).

EXAMPLE 51

To a stirred suspension of 60% sodium hydride (470 mg) in N,N-dimethylformamide (6 ml) was added a solution of methyl 2-ethylindole-6-carboxylate (1.99 g) in N,N-dimethylformamide (12 ml) at 20° C. The mixture was stirred at 20° C. for 30 minutes. To this mixture was added 2-chlorobenzylbromide (2.21 g) at 20° C. and the mixture was stirred at 20° C. for 5.5 hours. N,N-Dimethylformamide was evaporated off, and the residue was extracted with ethyl acetate. The organic phase was washed with water and brine, dried over sodium sulfate and evaporated in vacuo. The residue was chromatographed on silica gel eluting with a mixture of ethyl acetate and hexane (1:8) to give crystals which were washed with hexane to give methyl 1-(2-chlorobenzyl-2-ethylindole-carboxylate (2.71 g) as colorless crystals.

mp: 87–89° C.; IR (KBr): 1709, 1278, 1236 cm$^{-1}$; NMR (CDCl$_3$, δ): 1.35 (3H, t, J=7 Hz), 2.67 (2H, q, J=7 Hz, 3.91 (3H, s), 5.45 (2H, s), 6.17 (1H, d, J=7 Hz), 6.46 (1H, s) 7.02 (1H, dd, J=7, 7 Hz), 7.19 (1H, dd, J=7, 7 Hz), 7.44 (1H, d, J=7 Hz), 7.62 (1H, d, J=7 Hz), 7.72 (1H, d, J=7 Hz) 7.93 (1H, s); MASS (m/z) 328 (M$^+$+1), 76 (bp).

EXAMPLE 52

The following compound was prepared in a similar manner to that of Example 32.

Methyl-(2-chlorobenzyl)-2-ethyl-3-formylindole-6-carboxylate mp: 168–169° C.; IR (KBr): 1715, 1650 cm$^{-1}$; NMR (CDCl$_3$, δ) 1.27 (3H, t, J=7 Hz), 3.06 (2H, q, J=7 Hz), 3.90 (3H, s), 5.50 (2H, s), 6.18 (1H, d, J=7 Hz), 7.05 (1H, t, J=7 Hz), 7.21–7.24 (1H, m), 7.48 (1H, d, J=7.5 Hz), 7.95 (1H, s), 8.01 (1H, d, J=7 Hz), 8.28 (1H, d, J=7 Hz), 10.25 (1H, s); MASS (m/z): 356 (M$^+$+1), 76 (bp).

EXAMPLE 53

A mixture of 1-(2-chlorobenzyl)-3-isobutyryl-2-propylindole-6-carboxylic acid (100 mg), diphenylphosphoryl azide (97 mg) and triethylamine (53 mg) in tert-butanol (4 ml) was refluxed for 2 hours, and then partitioned between ethynyl acetate and diluted with hydrochloric acid. The organic layer was washed with aqueous sodium bicarbonate and brine, dried over magnesium sulfate and evaporated in vacuo. The residue was purified by silica gel thin layer chromatography with a mixture of hexane and ethyl acetate (2:1) to give 6-tert-butoxycarbonylamino-1-(2-chlorobenzyl)-3-isobutyryl-2-propylindole (125 mg) as a pale yellow oil.

NMR (CDCl$_3$, δ) 0.98 (3H, t, J=7 Hz), 1.28 (6H, d, J=7 Hz), 1.48 (9H, s), 1.52–1.64 (2H, m), 2.96–3.02 (2H, m), 3.54 (1H, septet, J=7 Hz), 5.42 (2H, s), 6.30 (1H, d, J=8 Hz), 6.52 (1H, s), 7.05 (1H, t, J=8 Hz), 7.09 (1H, d, J=8 Hz), 7.20 (1H, t, J=8 Hz), 7.36–7.45 (2H, m), 7.82 (1H, d, J=8 Hz).

EXAMPLE 54

To a solution of 6-tert-butoxycarbonylamino-2-(2-chlorobenzyl)-3-isobutyryl-2-propylindole (110 mg) in ethyl acetate (1 ml) was added 4N hydrogen chloride in ethyl acetate at 20° C., and the mixture was stirred at the same temperature for 4 hours. The precipitates were collected by filtration and washed with ethyl acetate to give 6-amino-1-(2-chlorobenzyl)-3-isobutyryl-2-propylindole hydrochloride (50 mg) as powder.

NMR: (DMSO-d$_6$, δ): 0.92 (3H, t, J=7 Hz), 1.18 (6H, d, J=7 Hz), 1.49 (2H, sextet, J=7 Hz), 3.02–3.08 (2H, m), 3.52 (1H, septet, J=7 Hz), 5.58 (2H, s), 6.24 (1H, d, J=8 Hz), 7.17–7.35 (4H, m), 7.57 (1H, d, J=8 Hz), 8.02 (1H, d, J=8 Hz).

EXAMPLE 55

To a stirred solution of 6-tert-butoxycarbonylamino-1-(2-chlorobenzyl)-3-isobutyryl-2-propylindole (581 mg) in ethyl acetate (5 ml) was added 4N hydrogen chloride in ethyl acetate (5 ml) at 20° C. The reaction mixture was stirred at 20° C. for 6.5 hours, then diluted with 1N aqueous sodium hydroxide and extracted. The organic phase was dried over magnesium sulfate and evaporated in vacuo. The residue was chromatographed on silica gel eluting with a mixture of ethyl acetate and hexane (1:6 to 1:4) to give 6-amino-1-(2-chlorobenzyl)-3-isobutyryl-2-propylindole (361 mg) as yellow oil.

NMR (CDCl$_3$, δ): 1.00 (3H, t, J=7 Hz), 1.29 (6H, d, J=7 Hz) 1.51–1.64 (2H, m), 2.98–3.03 (2H, m), 3.49–3.57 (1H, m), 5.34 (2H, s), 6.36 (1H, d, J=7.5 Hz), 6.46 (1H, s), 6.71 (1H, d, J=7.5 Hz), 7.08 (1H, t, J=7.5 Hz), 7.21 (1H, t, J=7.5 Hz), 7.45 (1H, d, J=7.5 Hz), 7.85 (1H, d, J=7.5 Hz); MASS (m/z): 369 (M$^+$+1).

EXAMPLE 56

To a stirred solution of 6-amino-1-(2-chlorobenzyl)-3-isobutyryl-2-propylindole (79 mg) and triethylamine (0.065 ml) in dichloromethane (2 ml) was added acetyl chloride (0.02 ml) at 0° C. The reaction mixture was stirred at 20° C. for 2 hours, then diluted with dichloromethane. The organic phase was washed with 1N hydrochloric acid, water, aqueous sodium bicarbonate, water and brine, dried over magnesium sulfate and evaporated in vacuo. The residue was chromatographed on silica gel eluting with a mixture of ethyl acetate and hexane (2:3) to give crystals which were recrystallized from a mixture of ethyl acetate and hexane to give 6-acetamide-1-(2-chlorobenzyl)-3-isobutyryl-2-propylindole (48 mg) as colorless crystals.

mp: 147–148° C.; IR (KBr): 1664, 1648, 1507, 1412 cm$^{-1}$; NMR (CDCl$_3$, δ): 1.00 (3H, t, J=7 Hz), 1.29 (6H, d, J=7 Hz), 1.51–1.65 (2H, m), 2.17 (3H, s), 2.99–3.05 (2H, m), 3.49–3.58 (1H, m), 5.43 (2H, s), 6.30 (1H, d, J=7.5 Hz), 7.04 (1H, t, J=7.5 Hz), 7.13–7.23 (3H, m), 7.44 (1H, d, J=7.5 Hz), 7.72 (1H, s), 7.85 (1H, d, J=7.5 Hz); MASS (m/z): 411 (M$^+$+1).

EXAMPLE 57

To a stirred solution of 6-amino-1-(2-chlorobenzyl)-3-isobutyryl-2-propylindole (100 mg) in chloroform (2 ml)

was added methylisocyanate (0.5 ml) at 0° C. The reaction mixture was stirred at 20° C. for 1 hour, then evaporated. The residue was chromatographed on silica gel eluting with a mixture of ethyl acetate and hexane (1:1) to give crystals which were recrystallized from a mixture of ethyl acetate and hexane to give 1-(2-chlorobenzyl)-3-isobutyryl-6-(3-methylureido)-2-propylindole (75 mg) as colorless crystals.

mp: 106–108.5° C.; IR (KBr): 1635, 1550, 1506 cm$^{-1}$; NMR (CDCl$_3$, δ): 1.01 (3H, t, J=7 Hz), 1.30 (6H, d, J=7 Hz), 1.53–1.65 (2H, m), 2.78 (3H, d, J=7 Hz), 3.00–3.06 (2H, m), 3.49–3.57 (1H, m), 4.61 (1H, d, J=7 Hz), 5.42 (2H, s), 6.29–6.32 (2H, m), 7.02–7.07 (2H, m), 7.22 (1H, ddd, J=7.5, 7.5, 1 Hz), 7.46 (1H, d, J=7.5 Hz), 7.88 (1H, d, J=7.5 Hz); MASS (m/z): 426 (M$^+$+1), 76 (bp).

EXAMPLE 58

To a stirred solution of 6-amino-1-(2-chlorobenzyl)-3-isobutyryl-2-propylindole (147 mg) in dichloromethane (2 ml) was added acetic formic anhydride (0.5 ml) at 0° C. The reaction mixture was stirred at 0° C. for 10 minutes, then diluted with dichloromethane. The organic phase was washed with water and brine, dried over magnesium sulfate and evaporated in vacuo. The residue was chromatographed on silica gel eluting with a mixture of ethyl acetate and hexane (1:2) to give crystals which were recrystallized from a mixture of ethyl acetate and hexane to give 1-(2-chlorobenzyl)-6-formamido-3-isobutyryl-2-propylindole (85 mg) as colorless crystals.

mp: 113–115° C.; IR (KBr): 1666, 1647, 1508 cm$^{-1}$; NMR (CDCl$_3$, δ): 1.00, 1.03 (3H, t and t, J=7 Hz), 1.28, 1.30 (6H, d and d, J=7 Hz), 1.54–1.65 (2H, m), 2.99–3.09 (2H, m), 3.47–3.57 (1H, m), 5.43 (2H, d, J=4 Hz), 6.31 (1H, d, J=7.5 Hz), 6.82–7.10 (2H, m), 7.17–7.25 (2H, m), 7.43–7.77 (2H, m), 7.90 (1H, dd, J=10, 7.5 Hz), 8.37–8.58 (1H, m); MASS (m/z): 397 (M$^+$+1).

EXAMPLE 59

A solution of 3-isobutyryl-1-(2-nitrobenzyl)-2-propylindole-6-carboxamide (316 mg) in methanol (10 ml) was hydrogenated over 10% palladium on carbon at 20° C. for 6 hours. The catalyst was filtered off and the filtrate was evaporated in vacuo. The residue was chromatographed on silica gel eluting with a mixture of methanol and chloroform 1:30) to give an oil which was dissolved in a mixture of chloroform (10 ml) and methanol (20 ml). To this solution was added 10% hydrogen chloride in methanol (0.9 ml), and the mixture was stirred at 20° C. for 1 hour and evaporated in vacuo. The residue was recrystallized from a mixture of methanol and diisopropyl ether to give 1-(2-aminobenzyl)-3-isobutyryl-2-propylindole-6-carboxamide hydrochloride (415 mg) as colorless crystals.

mp: 255–257° C.; IR (KBr): 1650, 1550, 1455 cm$^{-1}$; NMR (DMSO-d$_6$, δ): 0.95 (3H, t, J=7 Hz), 1.20 (3H, t, J=7 Hz), 1.46–1.59 (2H, m), 2.96–3.01 (2H, m), 5.67 (2H, s), 5.89 (1H, d, J=7.5 Hz), 6.87 (1H, br t, J=7 Hz), 7.19–7.34 (3H, m), 7.80 (1H, d, J=7.5 Hz), 7.92–7.98 (2H, m), 8.03 (1H, s); MASS (m/z): 378 (M$^+$+1), 86 (bp).

To a solution of 1-(2-chlorobenzyl)-3-methoxyacetyl-2-propylindole-6-carboxamide (168 mg) in a mixture of dichloromethane (10 ml) and methanol (0.5 ml) was added 1M solution of boron tribromide in dichloromethane (2.5 ml) at −53° C. The reaction mixture was warmed gradually to −12° C. during 3 hours. Then 1M solution of boron tribromide in dichloromethane (2.5 ml) was added, and the mixture was stirred for 20 minutes at −12° C. The reaction mixture was diluted with water and extracted with 10% methanol in chloroform. The organic phase was washed with aqueous sodium bicarbonate, water and brine, dried over magnesium sulfate and evaporated in vacuo. The residue was crystallized from ethyl acetate and washed with hexane to give 1-(2-chlorobenzyl)-3-hydroxyacetyl-2-propylindole-6-carboxamide (120 mg) as colorless crystals.

mp: 231–233.5° C.; IR (KBr): 3405, 3159, 1673, 1647, 1616, 1395 cm$^{-1}$; NMR (DMSO-d$_6$, δ): 0.94 (3H, t, J=7 Hz), 1.40–1.52 (2H, m), 3.05 (3H, t, J=7 Hz), 4.75 (2H, t, J=6 Hz), 4.90 (1H, t, J=6 Hz), 5.65 (2H, s), 6.22 (1H, d, J=7.5 Hz), 7.18 (1H, t, J=7.5 Hz), 7.27–7.35 (2H, m), 7.58 (1H, d, J=7.5 Hz), 7.81 (1H, d, J=7.5 Hz), 7.92 (2H, d, J=7.5 Hz), 8.01 (1H, s); MASS (m/z): 385 (M$^+$+1), 86 (bp).

EXAMPLE 61

To a stirred mixture of benzyl 3-isobutyryl-2-propylindole-6-carboxylate (207 mg) and diisopropylethylamine (295 mg) in dichloromethane (6 ml) were added 2-chlorobenzoyl chloride (299 mg) and 4-dimethylaminopyridine (12 mg) at 0° C. The reaction mixture was refluxed for 15 hours. The reaction mixture was cooled to 20° C. and washed with 1N hydrochloric acid, water, saturated sodium bicarbonate, water and brine. The organic phase was dried over sodium sulfate and evaporated in vacuo. The residue was chromatographed or silica gel eluting with a mixture of ethyl acetate and hexane (1:10) to give benzyl 1-(2-chlorobenzoyl)-3-isobutyryl-2-propylindole-6-carboxylate (330 mg) as yellow crystals.

mg: 67.5–70° C. IR (KBr) 1780, 1710, 1700, 1300 cm$^{-1}$; NMR (CDCl$_3$, δ): 0.99 (3H, t, J=7 Hz), 1.27 (6H, t, J=7 Hz), 1.74 (2H, sextet, J=7 Hz), 3.12 (2H, t, J=7 Hz), 3.39–3.48 (1H, m), 5.25 (2H, s), 7.33–7.45 (8H, m), 7.53–7.58 (2H, m), 7.80 (1H, d, J=7.5 Hz), 7.98–8.05 (1H, m); MASS (m/z): 502 (M$^+$+1).

EXAMPLE 62

A solution of benzyl 1-(2-chlorobenzoyl)-3-isobutyryl-2-propylindole-6-carboxylate (304 mg) in methanol (6 ml) was hydrogenated over 10% palladium on carbon at 20° C. for 9 hours. The catalyst was filtered off and the filtrate was evaporated in vacuo. The residue was chromatographed on silica gel eluting with a mixture of methanol and chloroform (1:30) to give crystals which were recrystallized from a mixture of ethyl acetate and hexane to give 1-(2-chlorobenzoyl)-3-isobutyryl-2-propylindole-6-carboxylic acid (189 mg) as colorless crystals.

IR (KBr): 1710, 1695, 1980, 1315 cm$^{-1}$; NMR (CDCl$_3$, δ): 0.95 (3H, t, J=7Hz), 1.27 (6H, t, J=7 Hz), 1.64–1.75 (2H, m), 3.03–3.09 (1H, m), 3.40–3.49 (1H, m), 7.48–7.52 (2H, m), 7.58–7.67 (3H, m), 7.92 (2H, AB, J=8, 7.5 Hz)

EXAMPLE 63

To a stirred solution of 1-(2-chlorobenzyl)-3-formylindole-6-carboxamide (47 mg) in dimethylformamide (1.6 ml) was added chromic anhydride (125 mg) and sulfuric acid (0.05 ml), and the mixture was stirred at 20° C. for 5 hours. The resulting mixture was evaporated in vacuo and the residue was chromatographed on silica gel eluting with a mixture of chloroform and methanol (9:1) to give 6-carbamoyl-1-(2-chlorobenzyl)indole-3-carboxylic acid (8.3 mg) as a solid.

mp: 240° C. (dec.); NMR (DMSO-d$_6$, δ): 5.64 (2H, s), 6.71 (1H, d, J=8 Hz), 7.26 (1H, t, J=8 Hz), 7.28 (1H, br s), 7.36 (1H, t, J=8 Hz), 7.56 (1H, d, J=8 Hz), 7.78 (1H, d, J=8 Hz), 7.92 (1H, br s), 8.06 (1H, s), 8.07 (1H, d, J=8 Hz), 8.20 (1H, s).

EXAMPLE 64

To a solution of 1-(2-chlorobenzyl)-2-(1-hydroxypropyl)-3-isobutyrylindole-6-carboxamide (19 mg) in acetone (3 ml) was added Jone's reagent until the red color existed continuously. The reaction was quenched by 2-propanol, then the mixture was diluted with ethyl acetate and washed with aqueous sodium bicarbonate and brine. The organic phase was dried over sodium sulfate and evaporated in vacuo. The residue was triturated with diisopropyl ether to give 1-(2-chlorobenzyl)-3-isobutyryl-2-propionylindole-6-carboxamide (9.3 mg).

mp: 145–147° C.; NMR (CDCl$_3$, δ): 1.15 (3H, t, J=7 Hz), 1.33 (6H, d, J=7 Hz), 2.60 (2H, q, J=7 Hz), 3.47 (1H, m), 5.46 (2H, s), 6.50 (1H, d, J=8 Hz), 7.09 (1H, t, J=8 Hz), 7.21 (1H, t, J=8 Hz), 7.42 (1H, d, J=8 Hz), 7.70 (1H, d, J=8 Hz), 7.88 (1H, s), 7.98 (1H, s).

EXAMPLE 65

The following compound was prepared in a similar manner to that of Preparation 45.

3-Chloro-1-(2-chlorobenzyl)-2-propylindole-6-carboxamide mp: 163–166° C.; NMR (CDCl$_3$, δ): 0.95 (3H, t, J=7 Hz), 1.58 (2H, m), 2.73 (2H, t, J=7 Hz), 5.43 (2H, s), 6.19 (1H, d, J=8 Hz), 7.01 (1H, t, J=8 Hz), 7.18 (1H, t, J=8 Hz), 7.43 (1H, d, J=8 Hz), 7.54 (1H, d, J=8 Hz), 7.67 (1H, d, J=8 Hz), 7.82 (1H, s).

EXAMPLE 66

To a stirred solution of methyl 1-(2-bromobenzyl)-2-propylindole-6-carboxamide (52 mg) in a mixture of dichloromethane (3 ml) and pyridine (1 ml) was added pyridinium bromide perbromide (50 mg), and the mixture was stirred at 0° C. for 1.5 hours. The resulting mixture was diluted with ethyl acetate and washed with diluted hydrochloric acid, aqueous sodium bicarbonate and brine, then dried over sodium sulfate and evaporated in vacuo. The residue was triturated with a mixture of hexane and diisopropyl ether to give 3-bromo-1-(2-bromobenzyl)-2-propylindole-6-carboxamide (33 mg) as a solid.

mp: 122–125° C.; NMR (CDCl$_3$, δ): 0.98 (3H, t, J=7 Hz), 1.57 (2H, m), 2.73 (2H, t, J=7 Hz), 5.42 (2H, s) 6.15 (1H, d, J=8 Hz), 7.0–7.16 (2H, m), 7.5–7.65 (3H, m), 7.79 (1H, s).

EXAMPLE 67

The following compounds described in (1) to (2) were prepared in a similar manner to that of Example 42.

(1) 1-(2-Chlorobenzyl)-3-isobutyryl-2-propylindole-6-carbonitrile mp: 130–131° C.; NMR (CDCl$_3$, δ): 1.03 (3H, t, J=7 Hz), 1.30 (6H, d, J=7 Hz), 1.56–1.68 (2H, m), 3.06–3.12 (2H, m), 3.51 (1H, septet, J=7 Hz), 5.46 (2H, s), 6.23 (1H, d, J=8 Hz), 7.08 (1H, t, J=8 Hz), 7.27 (1H, t, J=8 Hz), 7.46–7.52 (3H, m), 8.01 (1H, d, J=8 Hz).

(2) 9-(2-Chlorobenzyl)-8-oxo-5,6,7,8-tetrahydrocarbazole-2-carbonitrile mp: 173–176° C.; NMR (CDCl$_3$, δ): 2.29 (2H, m), 2.69 (2H, t, J=7 Hz), 3.08 (2H, t, J=7 Hz), 5.94 (2H, s), 6.30 (1H, d, J=8 Hz), 7.02 (1H, t, J=8 Hz), 7.19 (1H, t, J=8 Hz), 7.38 (1H, d, J=8 Hz), 7.42 (1H, d, J=8 Hz), 7.54 (1H, s), 7.78 (1H, d, J=8 Hz).

EXAMPLE 68

To a solution of 1-(2-chlorobenzyl)-3-isobutyryl-2-propylindole-6-carbonitrile (70 mg) in a mixture of methanol (2 ml) and tetrahydrofuran (2 ml) was added sodium borohydride (21 mg) at 25° C. After stirred at 25° C. for 2 hours, the reaction mixture was partitioned between ethyl acetate and 1N hydrochloric acid. The organic layer was washed with water and brine, dried over magnesium sulfate, and evaporated in vacuo. The residue was crystallized from diisopropyl ether to give 1-(2-chlorobenzyl)-3-(1-hydroxy-2-methylpropyl)-2-propylindole-6-carbonitrile (28 mg) as pale yellow crystals.

mp: 126–127° C. NMR (CDCl$_3$, δ): 0.76 (3H, d, J=7 Hz), 0.98 (3H, t, J=7 Hz), 1.22 (3H, d, J=7 Hz), 1.50–1.64 (2H, m), 1.87 (1H, d, J=2 Hz), 2.32–2.44 (2H, m), 2.63–2.80 (2H, m), 4.58 (1H, dd, J=2, 8 Hz), 5.38 (2H, s), 6.15 (1H, d, J=8 Hz), 7.05 (1H, t, J=8 Hz), 7.22 (1H, t, J=8 Hz), 7.32 (1H, d, J=8 Hz), 7.38 (1H, s), 7.46 (1H, d, J=8 Hz), 7.91 (1H, d, J=8 Hz).

EXAMPLE 69

The following compound was prepared in a similar manner to that of Example 68.

1-(2-Chlorobenzyl)-2-ethyl-3-(1-hydroxy-2-methylpropyl)-indole-6-carboxamide mp: 169–172° C.; NMR (CDCl$_3$, δ): 0.78 (3H, d, J=7 Hz), 1.17 (3H, t, J=7 Hz), 1.23 (3H, d, J=7 Hz), 2.41 (1H, m), 2.74 (2H, m), 4.60 (1H, m), 5.43 (2H, s), 6.14 (1H, d, J=8 Hz), 6.98 (1H, t, J=8 Hz), 7.17 (1H, t, J=8 Hz), 7.4–7.5 (2H, m), 7.76 (1H, s), 7.85 (1H, d, J=8 Hz).

EXAMPLE 7

To a suspension of 3-acetyl-1-(2-chlorobenzyl)-2-propylindole-6-carboxamide (36.5 mg) in ethanol (5 ml) was added hydroxylamine hydrochloride (70 mg) and sodium acetate (200 mg), and the mixture was heated in a sealed tube at 100° C. The reaction was evaporated in vacuo, then the residue was diluted with ethyl acetate and washed with water and brine. The organic phase was dried over sodium sulfate and evaporated in vacuo. The residue was triturated with diisopropyl ether to give 1-(2-chlorobenzyl)-3-(1-hydroxyiminoethyl)-2-propylindole-6-carboxamide (32.7 mg).

mp: 212–216° C.; NMR (CDCl$_3$, δ): 0.94 (3H, t, J=7 Hz), 1.56 (2H, m), 2.39 (3H, s), 2.80 (2H, m), 5.45 (2H, s), 6.21 (1H, d, J=8 Hz), 6.99 (1H, t, J=8 Hz), 7.20 (1H, t, J8 Hz), 7.42 (1H, d, J=8 Hz), 7.50 (1H, m), 7.70–7.78 (2H, m).

EXAMPLE 71

1-(2-Aminobenzyl)-3-isobutyryl-2-propylindole-6-carboxamide hydrochloride (111 mg) was dissolved in chloroform, and the solution was washed with 1N aqueous sodium hydroxide, dried over magnesium sulfate and evaporated in vacuo. The residue was dissolved in chloroform (3 ml), and then methyl isocyanate (1.5 ml) was added at 0° C. After stirred at 20° C. for 2 hours, the mixture was evaporated in vacuo. The residue was dissolved in a mixture of ethyl acetate and tetrahydrofuran, and the solution was washed with water and brine, dried over magnesium sulfate and evaporated in vacuo. The crystalline residue was recrystallized from a mixture of 1,4-dioxane and hexane to give 3-isobutyryl-1-[2-(3-methylureido)benzyl]-2-propylindole-6-carboxamide (74 mg) as colorless crystals.

mp: 222–223° C.; IR (KBr) 1648, 1617, 1557 cm$^{-1}$; NMR (DMSO-d$_6$, δ): 0.91 (3H, t, J=7 Hz), 1.18 (6H, d, J=7 Hz), 1.42–1.50 (2H, m), 2.71 (3H, d, J=5 Hz), 2.92–3.00 (2H, m), 3.50–3.56 (1H, m), 5.48 (2H, s), 5.99 (1H, d, J=8 Hz), 6.34–6.39 (1H, m), 6.86 (1H, t, J=7.5 Hz), 7.18 (1H, t, J=7.5

Hz), 7.28 (1H, s), 7.55 (1H, t, J=7.5 Hz), 7.78 (1H, d, J=7.5 Hz), 7.92–7.97 (3H, m), 8.21 (1H, s); MASS (m/z): 435 (M$^+$+1), 86 (bp).

EXAMPLE 72

To a solution of methyl 1-(2-chlorobenzyl)-2-propylindole-6-carboxylate (200 mg) in trifluoroacetic acid (2 ml) was added concentrated nitric acid (0.3 ml) at 0° C. After stirred at 0° C. for 30 minutes, the reaction mixture was partitioned between ethyl acetate and water. The organic layer was washed with aqueous sodium bicarbonate, water and brine, dried over magnesium sulfate, and evaporated in vacuo. The residue was purified by preparative thin layer chromatography on silica gel eluting with a mixture of ethyl acetate and hexane (1:3) to give methyl 1-(2-chlorobenzyl)-3-nitro-2-propylindole-6-carboxylate (73 mg) as pale yellow crystals.

NMR (CDCl$_3$, δ): 1.04 (3H, t, J=7 Hz), 1.68 (2H, sextet, J=7 Hz), 3.14–3.18 (2H, m), 3.91 (3H, s), 5.13 (2H, s), 6.32 (1H, d, J=8 Hz), 7.08 (1H, t, J=8 Hz), 7.27 (1H, t, J=8 Hz), 7.48 (1H, d, J=8 Hz), 7.98 (1H, s), 8.08 (1H, d, J=8 Hz), 8.43 (1H, d, J=8 Hz).

EXAMPLE 73

The following compounds described in (1) to (44) were prepared in a similar manner to that of Example 1.

(1) Methyl 1-(2-chlorobenzyl)-2-(3-methoxycarbonylpropyl)-indole-6-carboxylate

NMR (CDCl$_3$, δ): 2.04 (2H, m), 2.88 (2H, t, J=7 Hz), 2.69 (2H, t, J=7 Hz), 3.62 (3H, s), 3.89 (3H, s), 5.43 (2H, s), 6.14 (1H, d, J=8 Hz), 6.46 (1H, s), 7.01 (1H, t, J=8 Hz), 7.18 (1H, t, J=8 Hz), 7.42 (1H, d, J=8 Hz), 7.59 (1H, d, J=8 Hz), 7.80 (1H, d, J=8 Hz), 7.90 (1H, s).

(2) Methyl 1-(2-chlorobenzyl)-2-(2-methoxycarbonylethyl)-indole-6-carboxylate

NMR (CDCl$_3$, δ): 2.77 (2H, m), 2.98 (2H, m), 3.69 (3H, s), 3.88 (3H, s), 5.45 (2H, s), 6.16 (1H, d, J=8 Hz), 6.41 (1H, s), 7.02 (1H, t, J=8 Hz), 7.19 (1H, t, J=8 Hz), 7.42 (1H, d, J=8 Hz), 7.60 (1H, d, J=8 Hz), 7.81 (1H, d, J=8 Hz), 7.91 (1H, s)

(3) Methyl 1-(2-chlorobenzyl)-3-isobutyryl-2-propylindole-7-carboxylate

NMR (CDCl$_3$, δ): 1.02 (3H, t, J=7 Hz), 1.79 (6H, d, J=7 Hz), 1.63 (2H, m), 3.01 (2H, m), 3.52 (1H, m), 3.56 (3H, s), 5.61 (2H, s), 6.08 (1H, d, J=8 Hz), 6.98 (1H, t, J=8 Hz), 7.17 (1H, t, J=8 Hz), 7.2–7.45 (3H, m), 8.12 (1H, d, J=8 Hz).

(4) Methyl 1-(2-chlorobenzyl)-3-isobutyryl-2-propylindole-5-carboxylate

NMR (CDCl$_3$, δ): 1.03 (3H, t, J=8 Hz), 1.34 (6H, d, J=8 Hz), 1.62 (2H, sextet, J=8 Hz), 3.06–3.10 (2H, m), 3.64 (1H, septet, J=8 Hz), 3.96 (3H, s), 5.47 (2H, s), 6.26 (1H, d, J=8 Hz), 7.06 (1H, t, J=8 Hz), 7.20 (1H, t, J=8 Hz), 7.25 (1H, d, J=8 Hz), 7.47 (1H, dd, J=1, 8 Hz), 7.92 (1H, d, J=8 Hz), 8.68 (1H, d, J=1 Hz).

(5) Methyl 1-(6-chloro-3,4-methylenedioxybenzyl)-3-isobutyryl-2-propylindole-5-carboxylate NMR (CDCl$_3$, δ): 1.05 (3H, t, J=8 Hz), 1.32 (6H, d, J=8 Hz), 1.62 (2H, sextet, J=8 Hz), 3.06 (2H, t, J=8 Hz), 3.63 (1H, septet, J=8 Hz), 3.96 (3H, s), 5.36 (2H, s), 5.74 (1H, s), 5.88 (2H, s), 6.92 (1H, s), 7.20 (1H, d, J=10 Hz), 7.82 (1H, d, J=10 Hz), 8.76 (1H, s).

(6) Methyl 1-(2-chlorobenzyl)-2-propylindole-4-carboxylate

NMR (CDCl$_3$, δ): 1.01 (3H, t, J=7 Hz), 1.78 (2H, m), 2.67 (2H, t, J=7 Hz), 3.99 (3H, s), 5.42 (2H, s), 6.18 (1H, d, J=8 Hz), 7.01 (1H, t, J=8 Hz), 7.03 (1H, s), 7.11 (1H, t, J=8 Hz), 7.18 (1H, t, J=8 Hz), 7.30 (1H, d, J=8 Hz), 7.43 (1H, d, J=8 Hz), 7.89 (1H, d, J=8 Hz).

(7) Methyl 9-(2-chlorobenzyl)-8-oxo-5,6,7,8-tetrahydrocarbazole-2-carboxylate

NMR (CDCl$_3$, δ): 2.27 (2H, m), 2.67 (2H, t, J=7 Hz), 3.11 (2H, t, J=7 Hz), 3.90 (3H, s), 5.95 (2H, s), 6.25 (1H, d, J=8Hz), 6.98 (1H, t, J=8 Hz), 7.15 (1H, t, J=8 Hz), 7.40 (1H, d, J=8 Hz), 7.74 (1H, d, J=8 Hz), 7.84 (1H, d, J=8 Hz), 7.99 (1H, s).

(8) Methyl 9-(6-chloro-3,4-methylenedioxybenzyl)-8-oxo-5,6,7,3-tetrahydrocarbazole-2-carboxylate NMR (CDCl$_3$, δ): 2.18 (2H, m), 2.63 (2H, t, J=7 Hz), 3.07 (2H, t, J=7 Hz), 3.84 (3H, s), 5.68 (1H, s), 5.63 (2H, s), 5.96 (2H, s), 7.18 (1H, s), 7.84 (1H, d, J=8 Hz), 7.92 (1H, d, J=8 Hz), 8.03 (1H, s).

(9) Methyl 1-(4-bromo-2-chlorobenzyl)-3-isobutyryl-2-propylindole-6-carboxylate mp: 65–567° C.; IR (KBr): 1715, 1705, 1656, 1456, 1433 cm$^{-1}$; NMR (CDCl$_3$, δ): 1.03 (3H, t, J=7 Hz), 1.30 (6H, d, J=7 Hz), 1.52–1.64 (2H, m), 2.99–3.05 (2H, m), 3.51–3.60 (1H, m), 3.92 (3H, s), 5.45 (2H, s), 6.09 (1H, d, J=7.5 Hz), 7.18 (1H, d, J=7.5 Hz), 7.66 (1H, s), 7.90 (1H, s), 7.99 (2H, s); MASS (m/z): 492 (M$^+$+2).

(10) 1-(2-Acetamidobenzyl)-3-isobutyryl-2-propylindole-6-carboxamide mp: 235–236° C.; IR (KBr): 1693, 1656, 1457 cm$^{-1}$; NMR (CDCl$_3$, δ): 0.91 (3H, t, J=7 Hz), 1.18 (6H, d, J=7 Hz), 1.39–1.50 (2H, m), 2.17 (3H, s), 2.92–2.99 (2H, m), 3.50–3.59 (1H, m), 5.49 (2H, s), 6.07 (1H, d, J=7.5 Hz), 7.00 (1H, t, J=7.5 Hz), 7.21–7.29 (2H, m), 7.39 (1H, d, J=7.5 Hz), 7.79 (1H, d, J=7.5 Hz), 7.92–7.96 (3H, m), 9.85 (1H, s); MASS (m/z): 420 (M$^+$+1), 86 (bp).

(11) Methyl 1-(2-chlorobenzyl)-3-formylindole-6-carboxylate

NMR (CDCl$_3$, δ)): 3.93 (3H, 5), 5.52 (2H, S), 6.88 (1H, dd, J=1, 8 Hz), 7.21 (1H, dt, J=1, 8 Hz), 7.32 (1H, dt, J=1, 8 Hz), 7.49 (1H, dd, J=1, 8 Hz), 7.82 (1H, s), 8.02 (1H, dd, J=1, 8 Hz), 8.13 (1H, d, J=1 Hz), 8.36 (1H, d, J=8 Hz), 10.0 (1H, s).

(12) Methyl 3-acetyl-1-(2-chlorobenzyl)-2-methylindole-6-carboxylate

This compound was used immediately without purification.

(13) Methyl 1-(2-chlorobenzyl)-2-methyl-3-propionylindole-6-carboxylate

NMR (CDCl$_3$, δ): 1.31 (3H, t, J=7 Hz), 2.70 (3H, s), 3.09 (2H, q, J=7 Hz), 3.90 (3H, s), 5.50 (2H, s), 6.22 (1H, d, J=8 Hz), 7.04 (1H, t, J=8 Hz), 7.24 (1H, t, J=8 Hz), 7.46 (1H, d, J=8 Hz), 7.92–7.98 (2H, m), 8.08 (1H, d, J=8 Hz).

(14) Methyl 1-(2-chlorobenzo[b]thiophen-3-ylmethyl)-3-isobutyryl-2-methylindole-6-carboxylate NMR (DMSO-d$_6$, δ): 1.14 (6H, d, J=7 Hz), 2.72 (3H, s), 3.48 (1H, m), 3.81 (3H, s), 5.91 (2H, s), 7.3–7.5 (3H, m), 7.80 (1H, d, J=8 Hz), 7.98 (1H, d, J=8 Hz), 8.06 (1H, d, J=8 Hz), 8.19 (1H, s).

(15) Methyl 1-(benzothiazol-2-ylmethyl)-2-ethyl-3-isobutyrylindole-6-carboxylate NMR (CDCl$_3$, δ): 1.28 (3H, t, J=7 Hz), 1.30 (6H, d, J=7 Hz), 3.24 (2H, q, J=7 Hz), 3.53 (1H, m), 3.91 (3H, s), 5.82 (2H, s), 7.25–7.53 (2H, m), 7.72 (1H, m), 7.8–8.1 (3H, m), 8.18 (1H, s).

(16) Methyl 1-(benzo[b]thiophen-5-ylmethyl)-3-isobutyryl-2-propylindole-6-carboxylate NMR (CDCl₃, δ): 1.02 (3H, t, J=7 Hz), 1.32 (6H, d, J=7 Hz), 1.62 (2H, m), 3.13 (2H, m), 3.57 (1H, m), 3.87 (3H, s), 5.57 (2H, s), 7.03 (1H, d, J=8 Hz), 7.18 (1H, d, J=6 Hz), 7.29 (1H, s), 7.44 (1H, d, J=6 Hz), 7.79 (1H, d, J=8 Hz), 7.94 (2H, s), 8.02 (1H, s).

(17) Methyl 1-allyl-3-isobutyryl-2-propylindole-6-carboxylate

NMR (CDCl₃, δ): 1.07 (3H, t, J=7 Hz), 1.28 (6H, d, J=7 Hz), 1.69 (2H, m), 3.12 (2H, m), 3.54 (1H, m), 3.94 (3H, s), 4.84 (2H, m), 4.87 (1H, m), 5.22 (1H, m), 5.98 (1H, m), 7.89 (1H, d, J=8 Hz), 7.94 (1H, d, J=8 Hz), 8.04 (1H, s).

(18) Methyl 1-(2-chlorobenzyl)-3-isobutyryl-2-(1-propenyl)indole-6-carboxylate

NMR (CDCl₃, δ): 1.23 (6H, d, J=7 Hz), 1.93 (3H, d, J=7 Hz), 3.51 (1H, m), 3.89 (3H, s), 5.50 (2H, s), 6.41 (1H, m), 6.42 (1H, d, J=8 Hz), 6.73 (1H, d, J=16 Hz), 7.07 (1H, t, J=8 Hz), 7.23 (1H, t, J=8 Hz), 7.47 (1H, d, J=8 Hz), 7.89 (1H, s), 7.95 (1H, d, J=8 Hz), 8.18 (1H, d, J=8 Hz).

(19) Methyl 2-(1-acetoxypropyl)-1-(2-chlorobenzyl)-3-isobutyrylindole-6-carboxylate NMR (CDCl₃, δ): 1.04 (3H, t, J=7 Hz), 1.2–1.35 (9H, m), 1.9–2.1 (2H, m), 3.59 (1H, m), 3.89 (3H, s), 5.61 (1H, d, J=17 Hz), 5.79 (1H, d, J=17 Hz), 6.04 (1H, d, J=8 Hz), 6.71 (1H, m), 7.01 (1H, t, J=8 Hz), 7.2 (1H, t, J=8 Hz), 7.47 (1H, d, J=8 Hz), 7.87 (1H, s), 7.92 (1H, d, J=8 Hz), 7.97 (1H, d, J=8 Hz).

(20) Methyl 3-(3,3-dimethylbutanoyl)-1-(2-chlorobenzyl)indole-6-carboxylate

NMR (CDCl₃, δ): 1.09 (9H, s ), 2.69 (2H, s), 3.93 (3H, s), 5.50 (2H, s), 6.73 (1H, d, J=8 Hz), 7.17 (1H, t, J=8 Hz), 7.28 (1H, t, J=8 Hz), 7.47 (1H, d, J=8 Hz), 7.82 (1H, s), 8.00 (1H, d, J=8 Hz), 8.08 (1H, s), 8.53 (1H, d, J=8 Hz).

(21) Ethyl 1-(2-chlorobenzyl)-3-isobutyryl-2-propylindole-6-ylacetate

IR (Neat): 1730, 1655 cm⁻¹; NMR (CDCl₃, δ): 1.00 (3H, t, J=7 Hz), 1.20 (3H, t, J=7 Hz), 1.29 (6H, d, J=7 Hz), 1.55–1.65 (2H, m), 3.01–3.08 (2H, m), 3.54–3.60 (1H, m), 3.69 (2H, s), 4.11 (2H, q, J=7 Hz), 5.44 (2H, s), 6.30 (1H, d, J=7.5 Hz), 7.03–7.10 (2H, m), 7.21 (2H, d, J=7.5 Hz), 7.46 (1H, d, J=7.5 Hz), 7.89 (1H, d, J=7.5 Hz); MASS (m/z): 440 (M⁺+1), 74 (bp).

(22) Methyl 1-(6-chloro-3,4-methylenedioxybenzyl)-3-isobutyryl-2-propylindole-6-ylacetate mp: 119–120.5° C.; IR (KBr) 1744, 1735, 1732, 1644, 1508 cm⁻¹; NMR (CDCl₃, δ): 1.03 (3H, t, J=7 Hz), 1.29 (6H, d, J=7 Hz), 1.55–1.65 (2H, a), 3.00–3.07 (2H, m), 3.53–3.61 (1H, m), 3.70 (3H, s), 3.72 (2H, s), 5.33 (2H, s), 5.80 (2H, s), 5.91 (2H, s),6.93 (1H, s), 7.01 (1H, s), 7.21 (1H, d, J=7.5 Hz), 7.89 (1H, d, J=7.5 Hz); MASS (m/z): 470 (M⁺+1), 74 (bp).

(23) Methyl 1-(2-chlorobenzyl)-2-propylindole-6-carboxylate

NMR (CDCl₃, δ): 1.02 (3H, t, J=7 Hz), 1.75 (2H, m), 2.62 (2H, t, J=7 Hz), 3.87 (3H, s), 5.42 (2H, s), 6.16 (1H, d, J=8 Hz), 6.42 (1H, s), 7.01 (1H, t, J=8 Hz), 7.19 (1H, t, J=8 Hz), 7.42 (1H, t, J=8 Hz), 7.58 (1H, d, J=8 Hz), 7.79 (1H, d, J=8 Hz), 8.92 (1H, s).

(24) Methyl 1-(2-bromobenzyl)-2-propylindole-6-carboxylate

NMR (CDCl₃, δ): 0.99 (3H, t, J=7 Hz), 1.74 (2H, m), 2.59 (2H, t, J=7 Hz), 3.88 (3H, s), 5.37 (2H, s), 6.12 (1H, d, J=8 Hz), 6.42 (1H, s), 7.0–7.15 (2H, m), 7.52–7.65 (2H, m), 7.79 (1H, d, J=8 Hz), 7.89 (1H, s).

(25) Methyl 2-acetyl-1-(2-chlorobenzyl)-3-methylindole-t-carboxylate

NMR (CDCl₃, δ): 2.61 (3H, s), 2.71 (3H, s), 3.90 (3H, s), 5.82 (2H, s), 6.19 (1H, d, J=8 Hz), 6.97 (1H, t, J=8 Hz), 7.14 (1H, t, J=8 Hz), 7.41 (1H, d, J=8 Hz), 7.79 (1H, d, J=8 Hz), 7.86 (1H, d, J=8 Hz), 7.99 (1H, s).

(26) Methyl 2-chloro-1-(2-chlorobenzyl)-3-ethylindole-6-carboxylate

NMR (CDCl₃, δ): 1.29 (3H, t, J=7 Hz), 2.83 (2H, q, J=7 Hz), 3.90 (3H, s), 5.50 (2H, s), 6.29 (1H, d, J=8 Hz), 7.04 (1H, t, J=8 Hz), 7.19 (1H, t, J=8 Hz), 7.42 (1H, d, J=8 Hz), 7.61 (1H, d, J=8 Hz), 7.83 (1H, d, J=8 Hz), 7.90 (1H, s).

(27) Methyl 1-(2-chlorobenzyl)-2-propionyl-3-propylindole-6-carboxylate

NMR (CDCl₃, δ): 1.07 (3H, t, J=7 Hz), 1.17 (3H, t, J=7 Hz), 1.78 (2H, m), 2.94 (2H, q, J=7 Hz), 3.09 (2H, m), 3.89 (3H, s), 5.72 (2H, s), 6.23 (1H, d, J=8 Hz), 6.98 (1H, t, J=8 Hz), 7.15 (1H, t, J=8 Hz), 7.39 (1H, d, J=8 Hz), 7.76 (1H, d, J=8 Hz), 7.63 (1H, d, J=8 Hz), 7.96 (1H, s).

(28) Methyl 1-(2-chlorobenzyl)-2-isobutyryl-3-propylindole-6-carboxylate

NMR (CDCl₃, δ): 1.03 (3H, t, J=7 Hz), 1.11 (6H, d, J=7 Hz), 1.75 (2H, m), 3.02 (2H, m), 3.35 (1H, m), 3.89 (3H, s), 5.64 (2H, s), 6.28 (1H, d, J=8 Hz), 6.99 (1H, t, J=8 Hz), 7.16 (1H, t, J=8 Hz), 7.38 (1H, d, J=8 Hz), 7.73 (1H, d, J=8 Hz), 7.84 (1H, d, J=8 Hz), 7.96 (1H, s).

(29) Methyl 1-(2-chlorobenzyl)-3-(3-oxo-1-butenyl)indole-6-carboxylate

NMR (CDCl₃, δ): 2.38 (3H, s), 3.93 (3H, s), 5.48 (2H, s), 6.7–6.8 (2H, m), 7.17 (1H, t, J=8 Hz), 7.28 (1H, t, J=8 Hz), 7.47 (1H, d, J=8 Hz), 7.54 (1H, d, J=8 Hz), 7.74 (1H, d, J=15 Hz), 7.96 (1H, s), 8.11 (1H, s).

(30) Methyl 4-(2-chlorobenzyl)-3-oxo-1,2,3,4-tetrahydrocyclopent[b]indole-6-carboxylate NMR (CDCl₃, δ): 3.06 (2H, m), 3.17 (2H, m), 3.92 (3H, s), 5.72 (2H, s), 6.59 (1H, d, J=8 Hz), 7.06 (1H, t, J=8 Hz), 7.19 (1H, t, J=8 Hz), 7.42 (1H, d, J=8 Hz), 7.78 (1H, d, J=8 Hz), 7.87 (1H, d, J=8 Hz), 8.04 (1H, s).

(31) Methyl 4-(6-chloro-3,4-methylenedioxybenzyl)-3-oxo-1,2,3,4-tetrahydrocyclopent[b]indole-6-carboxylate NMR (CDCl₃, δ): 3.06 (3H, m), 3.14 (2H, m), 3.94 (3H, s), 5.60 (2H, s), 5.88 (2H, s), 6.11 (1H, s), 6.88 (1H, s), 7.76 (1H, d, J=8 Hz), 7.86 (1H, d, J=8 Hz), 8.09 (1H, s).

(32) 1-(2-Chlorobenzyl)-3-cyclopropanecarbonyl-2-propylindole-6-carboxamide mp: 162–163.5° C.; IR (KBr) 1675, 1612, 1444, 1383 cm⁻¹; NMR (DMSO-d₆, δ): 0.90 (3H, t, J=7 Hz), 1.08 (4H, d, J=7 Hz), 1.48 (2H, sextet, J=7 Hz), 2.65–2.72 (1H, m), 3.00 (2H, t, J=7 Hz), 5.62 (2H, s), 6.21 (1H, d, J=8 Hz), 7.18 (1H, t, J=8 Hz), 7.32 (1H, t, J=8 Hz), 7.58 (1H, d, J=8 Hz), 7.80 (1H, d, J=8 Hz), 7.93 (1H, s), 8.01 (1H, s), 8.10 (1H, d, J=7 Hz); MASS (m/z): 395 (M⁺+1), 74 (bp).

(33) 1-(6-Chloro-3,4-methylenedioxybenzyl)-3-cyclopropanecarbonyl-2-propylindole-6-carboxamide mp: 162–163.5° C.; IR (KBr) 1675, 1612, 1444, 1383 cm⁻¹; NMR (DMSO-d₆, δ): 0.90 (3H, t, J=7 Hz), 1.08 (4H, d, J=7 Hz), 1.48 (2H, sextet, J=7 Hz), 2.65–2.72 (1H, m), 3.00 (2H, t, J=7 Hz), 5.62 (2H, s), 6.21 (1H, d, J=8 Hz), 7.18 (1H, t, J=8 Hz), 7.32 (1H, J=8 Hz), 7.58 (1H, d, J=8 Hz), 7.80 (1H, d, J=8 Hz), 7.93 (1H, s), 8.01 (1H, s), 8.10 (1H, d, J=7 Hz); MASS (m/z): 395 (M⁺+1), 74 (bp).

(34) 1-(2-Chlorobenzyl) -3-cycobutanecarbonyl-2-propylindole-6-carboxamide mp: 162–165° C.; IR (KBr 1660, 1654, 1445, 1437 cm⁻¹; NMR (CDCl₃, δ): 1.02 (3H, t, J=7 Hz), 1.62 (2H, sextet, J=7 Hz), 1.95–2.14 0(2H, m), 2.35–2.52 (4H, m), 3.05–3.10 (2H, m), 4.05 (1H, quintet, J=7 Hz), 5.50 (2H, s), 6.22 (1H, d, J=7.5 Hz), 7.04 (1H, t, J=7.5 Hz), 7.21 (1H, t, J=7.5 Hz), 7.47 (1H, d, J=7.5 Hz), 7.63 (1H, d, J=7.5 Hz), 7.82 (1H, s), 7.97 (1H, d, J=7.5 Hz); MASS (m/z): 409 (M$^+$+1), 74 (bp).

(35) 1-(6-Chloro-3,4-methylenedioxybenzyl-3-cyclobutanecarbonyl-2-propylindole-6-carboxamide mp: 240–241° C.; IR (KBr) 1658, 1636, 1503, 1482, 1451 cm$^{-1}$; NMR (DMSO-d$_6$, δ): 0.94 (3H, t, J=7 Hz), 1.49 (2H, sextet, J=7 Hz), 1.79–1.90 (1H, m), 1.96–2.07 (1H, m), 2.24–2.33 (4H, m), 3.03 (2H, t, J=7 Hz), 4.07 (1H, quintet, J=7 Hz), 5.51 (2H, s), 5.65 (1H, s), 6.00 (2H, s), 7.24 (1H, s), 7.31 (1H, br s), 7.79 (1H, d, J=7.5 Hz), 7.94 (1H, br s), 7.95 (1H, d, J=7.5 Hz), 8.00 (1H, s); MASS (m/z): 453 (M$^+$+1), 85 (bp).

(36) 1-(2-Chlorobenzyl)-3-cyclopentanecarbonyl-2-propylindole-6-carboxamide mp: 201.5–202.5° C. IR (KBr): 1654, 1607, 1447, 1437, 1387 cm$^{-1}$; NMR (CDCl$_3$, δ): 1.02 (3H, t, J=7 Hz), 1.59–1.82 (6H, m), 1.99–2.07 (4H, m), 3.02–3.09 (2H, m), 3.79 (1H, quintet, J=7 Hz), 5.52 (2H, s), 6.23 (1H, d, J=7.5 Hz), 7.05 (1H, t, J=7.5 Hz), 7.22 (1H, t, J=7.5 Hz), 7.47 (1H, d, J=7.5 Hz), 7.63 (1H, d, J=7.5 Hz), 7.86 (1H, s), 8.04 (1H, d, J=7.5 Hz); MASS (m/z): 423 (M$^+$+1), 74 (bp).

(37) 1-(6-Chloro-3,4-methylenedioxybenzyl)-3-cyclopentanecarbonyl-2-propylindole-6-carboxamide mp: 236–237° C.; IR (KBr): 1662, 1506, 1477 cm$^{-1}$; NMR (DMSO-d$_6$, δ): 0.93 (3H, t, J=7 Hz), 1.40–1.50 (2H, m), 1.61–1.68 (4H, m), 1.81–1.95 (4H, m), 3.00 (2H, t, J=7 Hz), 3.73–3.82 (1H, m), 5.50 (2H, s), 5.64 (1H, s), 6.00 (2H, s), 7.24 (1H, s), 7.30 (1H, br s), 7.80 (1H, d, J=7.5 Hz), 7.95 (1H, br s), 8.00 (1H, d, J=7.5 Hz), 8.01 (1H, s); MASS (m/z): 467 (M$^+$+1), 85 (bp).

(38) 1-(2-chlorobenzyl)-3-cyclohexanecarbonyl-2-propylindole-6-carboxamide mp: 208–210° C.; IR (KBr): 1686, 1625, 1609, 1444, 1410 cm$^{-1}$; NMR (DMSO-d$_6$, δ): 0.90 (3H, t, J=7 Hz), 1.19–1.30 (1H, m), 1.39–1.49 (6H, m), 1.67–1.93 (5H, m), 2.99 (2H, t, J=7 Hz), 3.18–3.27 (1H, m), 5.61 (2H, s), 6.19 (1H, d, J=7.5 Hz), 7.18 (1H, t, J=7.5 Hz), 7.29 (1H, s), 7.32 (1H, t, J=7.5 Hz), 7.58 (1H, d, J=7.5 Hz), 7.80 (1H, d, J=7.5 Hz), 7.90 (2H, d, J=7.5 Hz), 8.00 (1H, s); MASS (m/z): 437 (M$^+$+1), 85 (bp).

(39) 1-(6-Chloro-3,4-methylenedioxybenzyl)-3-cyclohexanecarbonyl-2-propylindole-6-carboxamide mp: 209–211° C.; IR (KBr) 1623, 1611, 1506, 1391 cm$^{-1}$; NMR (DMSO-d$_6$, δ): 0.93 (3H, t, J=7 Hz), 1.20–1.28 (1H, m), 1.39–1.51 (6H, m), 1.68–1.92 (5H, m), 2.96–3.01 (2H, m), 3.19–3.27 (1H, m), 5.52 (2H, s), 5.64 (1H, s), 6.00 (2H, s), 7.24 (1H, s), 7.31 (1H, br s), 7.85 (2H, AB, J=7.5, 7.5 Hz), 7.96 (1H, br s), 8.01 (1H, s); MASS (m/z): 431 (M$^+$+1), 85 (bp).

(40) 1-(2-Chlorobenzyl)-3-(3-methyl-2-butenoyl)-2-propylindole e-6-carboxamide mp: 187–188° C.; IR (KBr): 1680, 1648, 1614, 1598, 1446, 1384 cm$^{-1}$; NMR (DMSO-d$_6$, δ): 0.90 (3H, t, J=7 Hz), 1.49 (2H, sextet, J=7 Hz), 2.01 (3H, s), 2.10 (3H, s), 2.99 (2H, t, J=7 Hz), 5.61 (2H, s), 6.19 (1H, d, J=7.5 Hz), 6.66 (1H, s), 7.19 (1H, t, J=7.5 Hz), 7.29 (1H, br s), 7.32 (1H, t, J=7.5 Hz), 7.58 (1H, d, (J=7.5 Hz), 7.78 (1H, d, J=7.5 Hz), 7.90 (1H, br s), 7.97 (2H, d, J=7.5 Hz); MASS (m/z): 409 (M$^+$+1), 85 (bp).

(41) 1-(6-Chloro-3,4-methylenedioxybenzyl)-3-(3-methyl-2-butenoyl)-2-propylindole-6-carboxamide mp: 227–229° C.; IR (KBr): 1654, 1606, 1505, 1482, 1449, 1388 cm$^{-1}$; NN (DMSO-d$_6$, δ): 0.94 (3H, t, J=7 Hz), 1.50 (2H, sextet, J=7 Hz), 2.01 (3H, s), 2.09 (3H, s), 3.00 (2H, t, J=7 Hz), 5.50 (2H, s), 5.67 (1H, s), 6.00 (2H, s), 6.66 (1H, s), 7.25 (1H, s), 7.30 (1H, br s), 7.77 (1H, d, J=7.5 Hz), 7.91–7.99 (3H, m); MASS (m/z): 453 (M$^+$+1), 85 (bp).

(42) 1-(2-Chlorobenzyl)-3-(3-methoxybutanoyl)-2-propylindole-6-carboxamide mp: 155–157° C.; IR (KBr): 1656, 1610, 1447, 1437, 1389 cm$^{-1}$; NMR (CDCl$_3$, δ): 1.03 (3H, t, J=7 Hz), 1.34 (3H, d, J=7 Hz), 1.63 (2H, sextet, J=7 Hz), 3.01–3.09 (3H, m), 3.41 (3H, s), 3.47 (1H, dd, J=16, 7 Hz), 4.14 (1H, sextet, J=7 Hz), 5.51 (2H, s), 6.22 (1H, dd, J=7.5, 1 Hz), 7.05 (1H, ddd, J=7.5, 7.5, 1 Hz), 7.23 (1H, ddd, J=7.5, 7.5, 1 Hz), 7.46 (1H, dd, J=7.5, 1 Hz), 7.62 (1H, dd, J=7.5, 1 Hz), 7.76 (1H, d, J=1 Hz), 8.09 (1H, d, J=7.5 Hz); MASS (m/z): 427 (M$^+$+1), 74 (bp).

(43) 1-(6-Chloro-3,4-methylenedioxybenzyl)-3-(3-methoxybutanoyl)-2-propylindole-6-carboxamide mp: 190–192.5° C.; IR (KBr): 1654, 1652, 1608, 1505, 1482 cm$^{-1}$; NMR (CDCl$_3$, δ): 1.04 (3H, t, J=7 Hz), 1.33 (3H, d, J=7 Hz), 1.62 (2H, sextet, J=7 Hz), 3.00–3.09 (3H, m), 3.40 (3H, s), 3.45 (1H, dd, J=16, 7 Hz), 4.12 (1H, sextet, J=7 Hz), 5.40 (2H, s), 5.70 (1H, s), 5.90 (2H, s), 6.91 (1H, s), 7.61 (1H, d, J=7.5 Hz), 7.88 (1H, s), 8.08 (1H, d, J=7.5 Hz); MASS (m/z): 471 (M$^+$+1), 74 (bp).

(44) 3-Acetyl-6-chloro-1-(2-chlorobenzyl)indole

NMR (CDCl$_3$, δ): 2.49 (3H, s), 5.41 (2H, s), 6.75 (1H, d, J=8 Hz), 7.18 (1H, t, J=8 Hz), 7.19 (1H, t, J=8 Hz), 7.2–7.33 (3H, m), 7.48 (1H, d, J=8 Hz), 7.72 (1H, s), 8.33 (1H, d, J=8 Hz).

EXAMPLE 74

The following compounds described in (1) to (43) were prepared in a similar manner to that of Example 2.

(1) 9-(2-Chlorobenzyl)-5-oxo-5,6,7,8-tetrahydrocarbazole-2-carboxylic acid

NMR (CDCl$_3$, δ): 2.24 (2H, m), 2.63 (2H, t, J=7 Hz), 2.88 (2H, t, J=7 Hz), 5.47 (2H, s), 6.36 (1H, d, J=8 Hz), 7.09 (1H, t, J=8 Hz), 7.26 (1H, t, J=8 Hz), 7.47 (1H, d, J=8 Hz), 8.02 (1H, s), 8.04 (1H, d, J=8 Hz), 8.37 (1H, d, J=8 Hz).

(2) 4-(2-Chlorobenzyl)-1-oxo-1,2,3,4-tetrahydrocyclopent-[b]indole-6-carboxylic acid NMR (DMSO-d$_6$, δ): 2.87 (2H, m), 3.03 (2H, m), 5.64 (2H, s), 6.93 (1H, d, J=8 Hz), 7.29 (1H, t, J=8 Hz), 7.37 (1H, t, J=8 Hz), 7.58 (1H, d, J=8 Hz), 7.78 (1H, d, J=8 Hz), 7.83 (1H, d, J=8 Hz), 8.05 (1H, s).

(3) 1-(2-Chlorobenzyl)-3-isobutyryl-2-propylindole-7-carboxylic acid

NMR (CDCl$_3$, δ): 1.03 (3H, t, J=7 Hz), 1.29 (6H, d, J=7 Hz), 1.64 (2H, m), 3.03 (2H, m), 3.56 (1H, m), 5.75 (2H, s), 6.04 (1H, d, J=8 Hz), 6.96 (1H, t, J=8 Hz), 7.12 (1H, t, J=8 Hz), 7.29 (1H, t, J=8 Hz), 7.33 (1H, d, J=8 Hz), 7.67 (1H, d, J=8 Hz) 8.19 (1H, d, J=8 Hz).

(4) 1-(2-Chlorobenzyl)-3-isobutyryl-2-propylindole-5-carboxylic acid

NMR (DMSO-d$_6$, δ): 0.90 (3H, t, J=8 Hz), 1.19 (6H, d, J=8 Hz), 1.62 (2H, sextet, J=8 Hz), 3.02 (2H, t, J=8 Hz), 3.51 (1H, septet, J=8 Hz), 5.64 (2H, s), 6.28 (1H, d, J=8 Hz), 7.18 (1H, t, J=8 Hz), 7.32 (1H, t, J=8 Hz), 7.50 (1H, d, J=8 Hz), 7.56 (1H, d, J=8 Hz), 7.78 (1H, d, J=8 Hz), 8.58 (1H, s).

(5) 1-(6-Chloro-3,4-methylenedioxybenzyl)-3-isobutyryl-2-propylindole-5-carboxylic acid NMR (CDCl$_3$, δ): 1.04 (3H, t, J=7 Hz), 1.32 (6H, d, J=7 Hz), 1.62 (2H, sextet, J=7 Hz), 3.06–3.12 (2H, m), 3.66 (1H, septet, J=7 Hz), 5.36 (2H, s), 5.74 (1H, s), 5.90 (2H, s), 6.93

(1H, s), 7.23 (1H, d, J=8 Hz), 7.96 (1H, dd, J=1, 8 Hz), 8.76 (1H, d, J=1 Hz).

(6) 1-(2-Chlorobenzyl)-2-propylindole-4-carboxylic acid

NMR (CDCl$_3$, δ): 1.03 (3H, t, J=7 Hz), 1.80 (2H, m), 2.67 (2H, t, J=7 Hz), 5.43 (2H, s), 6.19 (1H, d, J=8 Hz), 7.03 (1H, t, J=8 Hz), 7.1–7.25 (3H, m), 7.34 (1H, d, J=8 Hz), 7.41 (1H, d, J=8 Hz), 7.99 (1H, d, J=8 Hz).

(7) 9-(2-Chlorobenzyl)-8-oxo-5,6,7,8-tetrahydrocarbazole-2-carboxylic acid

NMR (CDCl$_3$, δ): 2.28 (2H, m), 2.68 (2H, t, J=7 Hz), 3.13 (2H, t, J=7 Hz), 5.95 (2H, s), 6.27 (1H, d, J=8 Hz), 6.99 (1H, t, J=8 Hz), 7.16 (1H, t, J=8 Hz), 7.42 (H, d, J=8 Hz), 7.77 (1H, d, J=8 Hz), 7.87 (1H, d, J=8 Hz), 8.03 (1H, s).

(8) 9-(6-Chloro-3,4-methylenedioxybenzyl)-6-oxo-5,6,7,8-tetrahydrocarbazole-2-carboxylic acid NMR (DMSO-d$_6$, δ): 2.19 (2H, m), 2.63 (2H, t, J=7 Hz), 3.06 (2H, t, J=7 Hz), 5.70 (1H, s), 5.82 (2H, s), 5.96 (2H, s), 7.16 (1H, s), 7.73 (1H, d, J=8 Hz), 7.88 (1H, d, J=8 Hz), 7.98 (1H, s).

(9) 1-(4-Chromo-2-chlorobenzyl)-3-isobutyryl-2-propylindole-6-carboxylic acid mp: 234–235° C.; IR (KBr): 1677, 1648, 1418 cm$^{-1}$; NMR (CDCl$_3$, δ): 1.04 (3H, t, J=7Hz), 1.30 (6H, d, J=7 Hz), 1.54–1.64 (2H, m), 3.02–3.08 (2H, m), 3.50–3.61 (1H, m), 5.44 (2H, s), 6.10 (1H, t, J=8 Hz), 7.18 (1H, dd, J=8, 1 Hz), 7.65 (1H, d, J=1 Hz), 7.94–6.05 (3H, m); MASS (m/z): 476 (M$^+$).

(10) 1-(2-Chlorobenzyl)-3-morpholinoacetyl-2-propylindole-6-carboxylic acid

IR (KBr): 1652, 1441, 1115 cm$^{-1}$; NMR (CDCl$_3$, δ): 1.02 (3H, t, J=7 Hz), 1.60 (2H, sextet, J=7 Hz), 2.74 (4H, t, J=6.5 Hz), 3.03–3.09 (2H, m), 3.86 (4H, t, J=6.5 Hz), 3.93 (2H, s), 5.52 (2H, s), 6.25 (1H, d, J=7.5 Hz), 7.05 (1H, t, J=7.5 Hz), 7.22 (1H, t, J=7.5 Hz), 7.47 (1H, d, J=7.5 Hz), 7.90–8.01 (3H, m); MASS (m/z): 455 (M$^+$-1).

(11) 1-(2-Chlorobenzyl)-3-(N,N-dimethylcarbamoyl)-2-propylindole-6-carboxylic acid IR (KBr): 1704, 1596, 1219 cm$^{-1}$; NMR (CDCl$_3$, δ): 0.93 (3H, t, J=7 Hz), 1.52–1.63 (2H, m), 2.80–2.90 (2H, m), 3.13 (6H, s) 5.48 (2H, s), 6.30 (1H, d, J=7.5 Hz), 7.04 (1H, t, J=7.5 Hz), 7.20 (1H, t, J=7.5 Hz), 7.44 (1H, d, J=7.5 Hz), 7.50 (1H, d, J=7.5 Hz), 7.91 (1H, d, J=7.5 Hz), 7.96 (1H, s); MASS (m/z): 399 (M$^+$-1).

(12) 1-(2-Chlorobenzyl)-3-morpholinocarbonyl-2-propylindole-6-carboxylic acid

IR (KBr): 3410, 1615, 1540, 1444, 1400 cm$^{31\ 1}$; NMR (DMSO-d$_6$, δ): 0.84 (3H, t, J=7 Hz), 1.39–1.49 (2H, m), 2.76–2.84 (2H, m), 3.56 (6H, br s), 3.68 (2H, br s), 5.52 (2H, s), 6.24 (1H, d, J=7.5 Hz), 7.16 (1H, t, J=7.5 Hz ), 7.29 (1H, t, J=7.5 Hz ), 7.40 (1H, d, J=7.5 Hz), 7.54 (1H, d, J=7.5 Hz), 7.79 (1H, s), 7.81 (1H, s); MASS (m/z): 439 (M$^+$-1), 99 (bp).

(13) 1-(2-Chlorobenzyl)-2-propylindole-3,6-dicarboxylic acid mp: 241–2432° C. (dec.); IR (KBr) 1669, 1525, 1443, 1385 cm$^{-1}$; NMR (DMSO-d$_6$, δ): 0.90 (3H, t, J=7 Hz), 1.44–1.55 (2H, m), 3.12 (2H, t, J=7 Hz), 5.56 (2H, s), 6.22 (1H, d, J=7.5 Hz), 7.17 (1H, t, J=7.5 Hz), 7.30 (1H, t, J=7.5 Hz), 7.57 (1H, d, J=7.5 Hz), 7.79 (1H, s), 8.06 (1H, d, J=7.5 Hz); MASS (m/z): 370 (M$^+$-1), 99 (bp).

(14) 1-(2-Chlorobenzyl)-2-ethyl-3-formylindole-6-carboxylic acid mp: 241–242° C. (dec.); IR (KBr): 1675, 1650, 1295 cm$^{-1}$; NMR (CDCl$_3$, δ): 1.29 (3H, t, J=7 Hz), 3.09 (2H, q, J=7 Hz), 5.52 (2H, s), 6.30 (1H, d, J=7.5 Hz), 7.08 (1H, t, J=7.5 Hz), 7.25 (1H, t, J=7.5 Hz), 7.49 (1H, d, J=7.5 Hz), 7.97 (1H, s), 8.03 (1H, d, J=7.5 Hz), 8.35 (1H, d, J=7.5 Hz), 10.25 (1H, s); MASS (m/z): 340 (M$^+$-1).

(15) 1-(2-Chlorobenzyl)-3-formylindole-6-carboxylic acid

NMR (DMSO-d$_6$, δ): 5.73 (2H, s), 6.96 (1H, d, J=8 Hz), 7.23–7.4 (2H, m), 7.56 (1H, d, J=8 Hz), 7.89 (1H, d, J=8 Hz), 8.15 (1H, s), 8.21 (1H, s), 8.54 (1H, s), 10.0 (1H, s).

(16) 3-Acetyl-1-(2-chlorobenzyl)-2-methylindole-6-carboxylic acid

NMR (CDCl$_3$, δ): 2.71 (3H, s), 2.76 (3H, s), 5.50 (2H, s), 6.22 (1H, d, J=8 Hz), 7.05 (1H, t, J=8 Hz), 7.22 (1H, t, J=8 Hz), 7.47 (1H, d, J=8 Hz), 7.95–8.15 (3H, m), 8.08 (1H, d, J=8 Hz).

(17) 1-(2-Chlorobenzyl)-2-methyl-3-propionylindole-6-carboxylic acid

NMR (DMSO-d$_6$, δ): 1.14 (3H, t, J=7 Hz), 2.69 (3H, s), 3.04 (2H, q, J=7 Hz), 5.67 (2H, s), 6.24 (1H, d, J=8 Hz), 7.18 (1H, d, J=8 Hz), 7.22 (1H, t, J=8 Hz), 7.58 (1H, d, J=8 Hz), 7.83 (1H, d, J=8 Hz), 7.99 (1H, s), 8.16 (1H, d, J=8 Hz).

(18) 1-(2-Chlorobenzo[b]thiophen-3-ylmethyl)-3-isobutyryl-2-methylindole-6-carboxylic acid NMR (CDCl$_3$, δ): 1.25 (6H, d, J=7 Hz), 2.71 (3H, s), 3.50 (1H, m), 5.61 (2H, s), 6.99 (1H, d, J=8 Hz), 7.12 (1H, t, J=8 Hz), 7.28 (1H, t, J=8 Hz), 7.68 (1H, d, J=8 Hz), 7.95–8.02 (2H, m), 8.23 (1H, s).

(19) 1-(Benzothiazol-2-ylmethyl)-2-ethyl-3-isobutyrylindole-6-carboxylic acid

NMR (CDCl$_3$, δ): 1.28 (3H, t, J=7 Hz), 1.30 (6H, d, J=7 Hz), 3.24 (2H, q, J=7 Hz), 3.58 (1H, m), 5.86 (2H, 5), 7.39 (1H, t, J=8 Hz), 7.52 (1H, t, J=8 Hz), 7.87 (1H, d, J=8 Hz), 7.9–8.06 (3H, m), 8.20 (1H, s).

(20) 1-(Benzo[b]thiophen-5-ylmethyl)-3-isobutyryl-2-propylindole-6-carboxylic acid NMR (CDCl$_3$, δ): 1.02 (3H, t, J=7 Hz), 1.32 (6H, d, J=7 Hz), 1.63 (2H, m), 3.14 (2H, m), 3.57 (1H, m), 5.58 (2H, s), 7.04 (1H, d, J=8 Hz), 7.19 (1H, d, J=6 Hz), 7.31 (1H, s), 7.43 (1H, d, J=6 Hz), 7.81 (1H, d, J=8 Hz), 7.9–8.02 (2H, m), 8.08 (1H, s).

(21) 1-(2,4-Dichlorobenzyl)-3-isobutyryl-2-propylindole-6-carboxylic acid

NMR (DMSO-d$_6$, δ): 0.92 (3H, t, J=7 Hz), 1.18 (6H, d, J=7 Hz), 1.46 (2H, sextet, J=7 Hz), 3.02–3.07 (2H, m), 3.54 (2H, septet, J=7 Hz), 5.68 (2H, s), 6.27 (1H, d, J=8 Hz), 7.28 (1H, dd, J=2, 8 Hz), 7.76 (1H, d, J=2 Hz), 7.84 (1H, d, J=8 Hz), 7.96 (1H, s), 8.01 (1H, d, J=8 Hz).

(22) 3-Isobutyryl-2-propyl-1-(3-pyridylmethyl)indole-6-carboxylic acid

NMR (CDCl$_3$, δ): 1.04 (3H, t, J=7 Hz), 1.30 (6H, d, J=7 Hz), 1.63 (2H, sextet, J=7 Hz), 3.15 (2H, t, J=7 Hz), 3.57 (2H, septet, J=7 Hz), 5.51 (2H, s), 7.19–7.28 (2H, m), 7.95–8.01 (2H, m), 8.04 (1H, s), 8.52–8.56 (2H, m).

(23) 3-Isobutyryl-2-propyl-1-(1-naphthylmethyl)indole-6-carboxylic acid

NMR (DMSO-d$_6$, δ): 0.86 (3H, t, J=7 Hz), 1.22 (6H, d, J=7 Hz), 1.52 (2H, sextet, J=7 Hz), 3.05–3.10 (2H, m), 3.60 (1H, septet, J=7 Hz), 6.15 (1H, d, J=8 Hz), 6.17 (2H, s), 7.28 (1H, t, J=8 Hz), 7.64 (1H, t, J=8 Hz), 7.72 (1H, t, J=8 Hz), 7.84 (2H, d, J=8 Hz), 7.92 (1H, s), 8.12 (1H, d, J=8 Hz), 8.15 (1H, d, J=8 Hz), 8.36 (1H, d, J=8 Hz).

(24) 3-Isobutyryl-2-propyl-1-(2-naphthylmethyl)indole-6-carboxylic acid

NMR (DMSO-d$_6$, δ): 0.92 (3H, t, J=7 Hz), 1.19 (6H, d, J=7 Hz), 1.48 (2H, sextet, J=7 Hz), 3.14–3.18 (2H, m), 3.57

(1H, septet, J=7 Hz), 5.81 (2H, s), 7.20 (1H, d, J=8 Hz), 7.45–7.52 (3H, m), 7.76–7.90 (4H, m), 8.02 (1H, d, J=8 Hz), 8.08 (1H, s).

(25) 1-Allyl-3-isobutyryl-2-propylindole-6-carboxylic acid

NMR (CDCl$_3$, δ): 1.08 (3H, t, J=7 Hz), 1.28 (6H, d, J=7 Hz), 1.69 (2H, m), 3.13 (2H, m), 3.56 (1H, m), 4.88 (2H, m), 4.90 (1H, m), 5.23 (1H, m), 5.98 (1H, m), 7. 94 (1H, d, J=8 Hz), 8.02 (1H, d, J=8 Hz), 8.13 (1H, s).

(26) 1-(2-Chlorobenzyl)-3-isobutyryl-2-(1-propenyl) indole-6-carboxylic acid

NMR (CDCl$_3$, δ): 1.26 (6H, d, J=7 Hz), 1.93 (3H, d, J=7 Hz), 3.51 (1H, m), 5.50 (2H, s), 5.92 (1H, m), 6.44 (1H, d, J=6 Hz), 6.74 (1H, d, J=16 Hz), 7.09 (1H, t, J=8 Hz), 7.23 (1H, t, J=8 Hz), 7.48 (1H, d, J=8 Hz), 7.92 (1H, s), 8.02 (1H, d, J=8 Hz), 8.21 (1H, d, J=8 Hz).

(27) 1-(2-Chlorobenzyl)-2-(1-hydroxypropyl)-3-isobutyrylindole-6-carboxylic acid NMR (CDCl$_3$, δ): 0.92 (3H, t, J=7 Hz), 1.29 (3H, d, J=7 Hz), 1.36 (3H, d, J=7 Hz), 1.52 (1H, m), 1.88 (1H, m) , 3.70 (1H, m), 4.73 (1H, m), 5.51 (1H, d, J=17 Hz), 5.69 (1H, d, J=17 Hz), 6.44 (1H, d, J=8 Hz), 7.09 (1H, t, J=8 Hz), 7.23 (1H, t, J=8 Hz), 7.45 (1H, d, J=8 Hz), 7.9–8.1 (3H, m).

(28) 1-(2-Chlorobenzyl)-3-(3,3-dimethylbutanoyl)indole-6-carboxylic acid

NMR (CDCl$_3$, δ): 1.08 (9H, s), 2.70 (2H, s), 5.52 (2H, s), 6.77 (1H, d, J=8 Hz), 7.17 (1H, t, J=8 Hz), 7.29 (1H, t, J=8 Hz), 7.47 (1H, d, J=8 Hz), 7.86 (1H, s), 8.03 (1H, d, J=8 Hz), 8.12 (1H, s), 8.53 (1H, d, J=8 Hz).

(29) 1-(6-Chloro-3,4-methylenedioxybenzyl)-3-methoxyacetyl-2-propylindole-6-carboxylic acid NMR (CDCl$_3$, δ): 0.96 (3H, t, J=7 Hz), 1.45–1.58 (2H, m), 3.10 (2H, t, J=7 Hz), 3.40 (3H, s), 4.69 (2H, s), 5.55 (2H, s), 5.76 (1H, s), 5.98 (2H, s), 7.23 (1H, s), 7.82 (1H, d, J=8 Hz), 7.94 (1H, s), 7.96 (1H, d, J=8 Hz).

(30) 1-(2-Chlorobenzyl)-3-ethoxyacetyl-2-propylindole-6-carboxylic acid

NMR (DMSO-d$_6$, δ): 0.94 (3H, t, J=7 Hz), 1.17 (3H, t, J=7 Hz), 1.48 (2H, sextet, J=7 Hz), 3.08 (3H, t, J=7 Hz), 3.62 (2H, q, J7 Hz), 4.74 (2H, s), 5.68 (2H, s), 6.28 (1H, d, J=8 Hz), 7.18 (1H, t, J=8 Hz), 7.32 (1H, t, J=8 Hz), 7.56 (1H, d, J=8 Hz), 7.82 (1H, d, J=8 Hz), 7.96 (1H, s), 7.98 (1H, d, J=8 Hz).

(31) 1-(2-Chlorobenzyl)-3-isobutyryl-2-propylindole-6-ylacetic acid

IR (KBr): 1715, 1650 cm$^{-1}$; NMR (CDCl$_3$, δ): 1.00 (3H, t, J=7 Hz), 1.30 (6H, d, J=7 Hz), 1.54–1.66 (2H, m), 3.00–3.08 (2H, m), 3.50–3.62 (1H, m), 3.71 (2H, s), 5.47 (2H, s), 6.30 (1H, d, J=7.5 Hz), 7.01–7.08 (2H, m), 7.19–7.25 (2H, m), 7.45 (1H, d, J=7.5 Hz), 7.89 (1H, d, J=7.5 Hz); MASS (m/z): 412 (M$^+$+1), 74 (bp).

(32) 1-(6-Chloro-3,4-methylenedioxybenzyl)-3-isobutyryl-2-propylindole-6-ylacetic acid mp: 81–83° C.; IR (KBr): 1715, 1650 cm$^{-1}$; NMR (CDCl$_3$, δ): 1.02 (3H, t, J=7 Hz), 1.29 (6H, d, J=7Hz), 1.54–1.67 (2H, m), 3.01–3.07 (2H, m), 3.51–3.60 (1H, m), 3.75 (2H, s), 5.33 (2H, s), 5.79 (1H, s), 5.89 (2H, s), 6.91 (1H, s), 7.12 (1H, s), 7.21 (1H, d, J=7.5 Hz), 7.89 (1H, d, J=7.5 Hz); MASS (m/z): 456 (M$^+$+1), 74 (bp).

(33) 1-(2-Chlorobenzyl)-2-propylindole-6-carboxylic acid

NMR (CDCl$_3$, δ): 1.02 (3H, t, J=7 Hz), 1.74 (2H, m), 2.61 (2H, t, J=7 Hz), 5.42 (2H, s), 6.19 (1H, d, J=8 Hz), 6.46 (1H, s), 7.02 (1H, t, J=8 Hz), 7.18 (1H, t, J=8 Hz), 7.43 (1H, d, J=8 Hz), 7.61 (1H, d, J=8 Hz), 7.85 (1H, d, J=8 Hz), 7.95 (1H, s).

(34) 1-(2-Chlorobenzyl)-2-propylindole-6-carboxylic acid

NMR (CDCl$_3$, δ): 1.00 (3H, t, J=7 Hz), 1.73 (2H, m), 2.61 (2H, t, J=7 Hz), 5.37 (2H, s), 6.12 (1H, d, J=8 Hz), 6.46 (1H, s), 7.0–7.18 (2H, m), 7.61 (1H, d, J=8 Hz), 7.85 (1H, d, J=8 Hz), 7.96 (1H, s).

(35) 2-Acetyl-1-(2-chlorobenzyl)-3-methylindole-6-carboxylic acid

NMR (CDCl$_6$, δ): 2.62 (3H, s), 2.69 (3H, s), 5.82 (2H, s), 6.10 (1H, d, J=8 Hz), 7.09 (1H, t, J=8 Hz), 7.24 (1H, t, J=8 Hz), 7.51 (1H, d, J=8 Hz), 7.72 (1H, d, J=8 Hz), 7.93 (1H, d, J=8 Hz), 7.96 (1H, s).

(36) 2-Chloro-1-(2-chlorobenzyl)-3-ethylindole-6-carboxylic acid

NMR (CDCl$_3$, δ): 1.30 (3H, t, J=7 Hz), 2.84 (2H, q, J=7Hz), 5.50 (2H, s), 6.29 (1H, d, J=8 Hz), 7.06 (1H, t, J=8 Hz), 7.19 (1H, t, J=8 Hz), 7.43 (1H, d, J=8 Hz), 7.63 (1H, d, J=8 Hz), 7.88 (1H, d, J=8 Hz), 7.93 (1H, s).

(37) 1-(2-Chlorobenzyl)-2-propionyl-3-propylindole-6-carboxylic acid

NMR (CDCl$_3$, δ): 1.06 (3H, t, J=7 Hz), 1.14 (3H, t, J=7 Hz), 1.76 (2H, m), 2.94 (2H, q, J=7 Hz), 3.09 (2H, m), 5.72 (2H, s), 6.27 (1H, d, J=8 Hz), 6.99 (1H, t, J=8 Hz), 7.14 (1H, t, J=8 Hz), 7.39 (1H, d, J=8 Hz), 7.78 (1H, d, J=8 Hz), 7.87 (1H, d, J=8 Hz), 8.02 (1H, s).

(38) 1-(2-Chlorobenzyl)-2-isobutyryl-3-propylindole-6-carboxylic acid

NMR (CDCl$_3$, δ): 1.03 (3H, t, J=7 Hz), 1.11 (6H, d, J=7 Hz), 1.76 (2H, m), 3.03 (2H, m), 3.34 (1H, m), 5.64 (2H, s), 6.30 (1H, d, J=8 Hz), 7.01 (1H, t, J=8 Hz), 7.14 (1H, t, J=8 Hz), 7.39 (1H, d, J=8 Hz), 7.78 (1H, d, J=8 Hz), 7.88 (1H, d, J=8 Hz), 8.02 (1H, s).

(39) 1-(2-Chlorobenzyl)-3-(3-oxo-1-butenyl)indole-6-carboxylic acid

NMR (DMSO-d$_6$, δ): 2.32 (3H, s), 5.67 (2H, s), 6.76 (1H, d, J=15 Hz), 6.86 (1H, d, J=8 Hz), 7.28 (1H, t, J=8 Hz), 7.37 (1H, t, J=8 Hz), 7.54 (1H, d, J=8 Hz), 7.79 (1H, d, J=8 Hz), 7.83 (1H, d, J=15 Hz), 8.08 (1H, d, J=8 Hz), 8.11 (1H, s), 8.21 (1H, s).

(40) 4-(2-Chlorobenzyl)-3-oxo-1,2,3,4-tetrahydrocyclopent[b]-indole-6-carboxylic acid NMR (CDCl$_3$, δ): 3.07 (2H, m), 3.17 (2H, m), 5.72 (2H, s), 6.58 (1H, d, J=8 Hz), 7.06 (1H, t, J=8 Hz), 7.18 (1H, t, J=8 Hz), 7.40 (1H, d, J=8 Hz), 7.78 (1H, d, J=8 Hz), 7.89 (1H, d, J=8 Hz), 8.09 (1H, s)

(41) 4-(6-Chloro-3,4-methylenedioxybenzyl)-3-oxo-1,2,3,4-tetrahydrocyclopent[b]indole-6-carboxylic acid NMR (CDCl$_3$, δ): 3.07 (2H, m), 3.16 (2H, m), 5.61 (2H, s), 5.88 (2H, s), 6.10 (1H, s), 6.88 (1H, s), 7.78 (1H, d, J=8 Hz), 7.88 (1H, d, J=8 Hz), 8.12 (1H, s).

(42) 1-(2-Chlorobenzyl)-3-nitro-2-propylindole-6-carboxylic acid

NMR (DMSO-d$_6$, δ): 0.95 (3H, t, J=7 Hz), 1.55 (2H, sextet, J=7 Hz), 3.18–3.22 (2H, m), 5.78 (2H, s), 6.52 (1H, d, J=8 Hz), 7.22 (1H, t, J=8 Hz), 7.33 (1H, t, J=8 Hz), 7.58 (1H, d, J=8 Hz), 7.97 (1H, d, J=8 Hz), 8.08 (1H, s) 8.27 (1H, d, J=8 Hz).

(43) 1-(2-Chloro-4-carboxybenzyl)-3-isobutyryl-2-propylindole-6-carboxamide

NMR (DMSO-d$_6$, δ): 0.90 (3H, t, J=7 Hz), 1.18 (6H, d, J=7 Hz), 1.46 (2H, sextet, J=7 Hz), 3.00–3.05 (2H, m), 3.55 (1H, septet, J=7 Hz), 5.68 (2H, s), 6.33 (1H, d, J=8 Hz), 7.30 (1H, s), 7.72 (1H, dd, J=2, 8 Hz), 7.92 (1H, s), 7.95–7.99 (2H, m), 8.03 (1H, d, J=8 Hz).

EXAMPLE 75

The following compounds described in (1) to (41) were prepared in a similar manner to that of Example 3.

(1) 9-(2-Chlorobenzyl)-5-oxo-5,6,7,8-tetrahydrocarbazole-2-carboxamide mp: 295° C. (dec.);

NMR (DMSO-$d_6$, δ): 2.13 (2H, m), 2.48 (2H, t, J=7 Hz), 2.92 (2H, t, J=7 Hz), 5.62 (2H, s), 6.41 (1H, d, J=8 Hz), 7.21 (1H, t, J=8 Hz), 7.27 (1H, br s), 7.33 (1H, t, J=8 Hz), 7.57 (1H, d, J=8 Hz), 7.79 (1H, d, J=8 Hz), 7.92 (1H, br s), 8.02 (1H, s), 8.08 (1H, d, J=8 Hz).

(2) 4-(2-Chlorobenzyl)-1-oxo-1,2,3,4-tetrahydrocyclopent[b]-indole-6-carboxamide mp: >300° C.; NMR (DMSO-$d_6$, δ): 2.88 (2H, m), 2.97 (2H, m), 5.61 (2H, s), 6.81 (1H, d, J=8 Hz), 7.27 (1H, t, J=8 Hz), 7.36 (1H, br s), 7.38 (1H, t, J=8 Hz), 7.57 (1H, d, J=8 Hz), 7.76 (1H, d, J=8 Hz), 7.79 (1H, d, J=8 Hz), 7.96 (1H, br s), 8.05 (1H, s).

(3) 1-(2-Chlorobenzyl)-3-isobutyryl-2-propylindole-7-carboxamide mp: 181–183° C.; NMR (CDCl$_3$, δ): 1.03 (3H, t, J=7 Hz), 1.27 (6H, d, J=7 Hz,), 1.61 (2H, m), 3.02 (2H, m), 3.53 (1H, m), 5.34 (1H, br s), 5.46 (1H, br s), 5.69 (2H, s), 5.99 (1H, d, J=8 Hz), 6.96 (1H, t, J=8 Hz), 7.14 (1H, t, J=8 Hz), 7.15–7.25 (2H, m), 7.37 (1H, d, J=8 Hz), 8.07 (1H, m).

(4) 1-(2-Chlorobenzyl)-3-isobutyryl-2-propylindole-5-carboxamide

NMR (CDCl$_3$, δ): 1.03 (3H, t, J=8 Hz), 1.32 (6H, d, J=8 Hz), 1.64 (2H, sextet, J=8 Hz), 3.06 (2H, t, J=8 Hz), 3.62 (1H, septet, J=8 Hz), 5.46 (2H, s), 6.26 (1H, d, J=8 Hz), 7.05 (1H, t, J=8 Hz), 7.20 (1H, t, J=8 Hz), 7.2 (1H, d, J=8 Hz), 7.47 (1H, d, J=8 Hz), 7.65 (1H, d, J=8 Hz), 8.55 (1H, s).

(5) 1-(6-Chloro-3,4-methylenedioxybenzyl)-3-isobutyryl-2-propylindole-5-carboxamide NMR (CDCl$_3$, δ): 1.05 (3H, t, J=7 Hz), 1.32 (6H, d, J=7 Hz), 1.60–1.72 (2H, m), 3.04–3.10 (2H, m), 3.59 (1H, septet, J=7 Hz), 5.38 (2H, s), 5.74 (1H, s), 5.92 (2H, s), 6.92 (1H, s), 7.22 (1H, d, J=8 Hz), 7.66 (1H, dd, J=1, 8 Hz), 8.50 (1H, d, J=1 Hz).

(6) 1-(2-Chlorobenzyl)-2-propylindole-4-carboxamide mp: 198–200° C.;

NMR (CDCl$_3$, δ): 1.02 (3H, t, J=7 Hz), 1.76 (2H, m), 2.66 (2H, t, J=7 Hz), 5.41 (2H, s), 6.18 (1H, d, J=8 Hz), 6.85 (1H, s), 7.1–7.3 (3H, m), 7.43 (1H, d, J=8 Hz), 7.52 (1H, d, J=8 Hz).

(7) 9-(2-Chlorobenzyl)-8-oxo-5,6,7,8-tetrahydrocarbazole-2-carboxamide mp: 255° C. (dec.); NMR (DMSO-$d_6$, δ): 2.18 (2H, m), 2.56 (2H, t, J=7 Hz), 3.07 (2H, t, J=7 Hz), 5.88 (2H, s), 6.08 (1H, d, J=8 Hz), 7.11 (1H, t, J=8 Hz), 7.25 (1H, t, J=8 Hz), 7.36 (1H, br s), 7.52 (1H, d, J=8 Hz), 7.72 (1H, d, J=8 Hz), 7.85 (1H, d, J=8 Hz), 8.02 (2H, m).

(8) 9-(6-Chloro-3,4-methylenedioxybenzyl)-8-oxo-5,6,7,8-tetrahydrocarbazole-2-carboxamide mp: 270° C. (dec.);

NMR (DMSO-$d_6$, δ): 2.17 (2H, m), 2.58 (2H, t, J=7 Hz), 3.08 (2H, t, J=7 Hz), 5.52 (1H, s), 5.78 (2H, s), 5.96 (2H, s), 7.17 (1H, s), 7.40 (1H, br s), 7.71 (1H, d, J=8 Hz), 7.86 (1H, d, J=8 Hz), 7.96 (1H, s), 8.01 (1H, br s).

(9) 1-(4-Bromo-2-chlorobenzyl)-3-isobutyryl-2-propylindole-6-carboxamide mp: 199–201° C.; IR (KBr): 3382, 1654, 1619, 1488, 1404 cm$^{-1}$; NMR (CDCl$_3$, δ): 1.04 (3H, t, J=7 Hz), 1.30 (6H, d, J=7 Hz), 1.54–1.66 (2H, m), 3.00–3.05 (2H, m), 3.50–3.60 (1H, m), 5.45 (2H, s), 6.09 (1H, t, J=7.5 Hz), 7.17 (1H, dd, J=7.5, 2 Hz), 7.62 (1H), dd, J=7.5, 2 Hz), 7.65 (1H, d, J=2 Hz), 7.83 (1H, s), 7.99 (1H, d, J=7.5 Hz); MASS (m/z): 477 (M$^+$+2).

(10) 1-(2-Chlorobenzyl)-3-morpholinoacetyl-2-propylindole-6-carboxamide

IR (KBr): 1654, 1616, 1452 cm$^{-1}$; NMR (CDCl$_3$, δ): 1.02 (3H, t, J=7 Hz), 1.58–1.68 (2H, m), 2.73 (4H, t, J=6.5 Hz), 3.05–3.10 (2H, m), 3.84 (4H, t, J=6.5 Hz), 3.89 (2H, s), 5.51 (2H, s), 6.23 (1H, d, J=7.5 Hz), 7.05 (1H, t, J=7.5 Hz), 7.22 (1H, t, J=7.5 Hz), 7.46 (1H, d, J=7.5 Hz), 7.64 (1H, d, J=7.5 Hz), 7.84 (1H, s), 7.98 (1H, d, J=7.5 Hz); MASS (m/z): 454 (M$^+$+1).

(11) Methyl 1-(2-chlorobenzyl)-3-(N,N-dimethylcarbamoyl)-2-propylindole-6-carboxylate IR (KBr): 1703, 1610 cm$^{-1}$; NMR (CDCl$_3$, δ): 0.94 (3H, t, J=7 Hz), 1.56–1.63 (2H, m,2.76–2.87 (2H, m), 3.11 (6H, br s), 3.90 (3H, s), 5.49 (2H, s), 6.29 (1H, d, J=7.5 Hz), 7.04 (1H, t, J=7.5 Hz), 7.21 (1H, t, J=7.5 Hz), 7.45 (1H, d, J=7.5 Hz), 7.49 (1H, d, J=7.5 Hz), 7.86 (1H, d, J=7.5 Hz), 7.90 (1H, s); MASS (m/z): 413 (M$^+$+1).

(12) Methyl 1-(2-chlorobenzyl)-3-(morpholinocarbonyl)-2-propylindole-6-carboxylate IR (KBr): 1(715, 1617, 1277, 1227 cm$^{-1}$; NMR (CDCl$_3$, δ): 0.85 (3H, t, J=7 Hz), 1.56–1.63 (2H, m), 2.82–2.90 (2H, m), 3.69 (6H, br s), 3.77 (2H, br s), 3.90 (3H, s), 5.48 (2H, s), 6.29 (1H, d, J=7.5 Hz), 7.04 (1H, t, J=7.5 Hz), 7.21 (1H, ddd, J=7.5, 7.5, 2 Hz), 7.45 (1H, d, J=7.5 Hz), 7.54 (1H, d, J=7.5 Hz), 7.88 (1H, s), 7.91 (1H, d, J=2 Hz); MASS (m/z): 455 (M$^+$+1), 76 (bp).

(13) 6-Carbamoyl-1-(2-chlorobenzyl)-N,N-dimethyl-2-propylindole-3-carboxamide mp: 213–214° C.; IR (KBr): 1676, 1601 cm$^{-1}$; NMR (CDCl$_3$, δ): 0.93 (3H, t, J=7 Hz), 1.52–1.62 (2H, m), 2.76–2.86 (2H, m), 3.12 (6H, br s), 5.47 (2H, s), 6.27 (1H, d, J=7.5 Hz), 7.03 (1H, t, J=7.5 Hz), 7.20 (1H, t, J=7.5 Hz), 7.44 (1H, d, J=7.5 Hz), 7.49–7.54 (2H, m), 7.78 (1H, s); MASS (m/z): 398 (M$^+$+1), 76 (bp).

(14) 1-(2-Chlorobenzyl)-3-(morpholinocarbonyl)-2-propylindole-6-carboxamide mp: 229–230° C.; IR (KBr): 3448, 3359, 3326, 1675, 1606 cm$^{-1}$; NMR (CDCl$_3$, δ): 0.95 (3H, t, J=7 Hz), 1.57–1.62 (2H, m), 2.82–2.89 (2H, m), 3.69 (6H, br s), 3.78 (2H, br s), 5.49 (2H, s), 6.28 (1H, d, J=7.5 Hz), 7.04 (1H, t, J=7.5 Hz), 7.21 (1H, t, J=7.5 Hz), 7.45 (1H, d, J=7.5 Hz), 7.55 (2H, s), 7.80 (1H, s); MASS (m/z): 440 (M$^+$+1), 76 (bp).

(15) 1-(2-Chlorobenzyl)-2-propylindole-3,6-dicarboxamide mp:296° C. (dec.); IR (KBr): 3376, 3188, 1644, 1613 cm$^{-1}$; NMR (DMSO-$d_6$, δ): 0.88 (3H, t, J=7 Hz), 1.40–1.51 (2H, m), 2.98 (2H, t, J=7 Hz), 5.57 (2H, s), 6.17 (1H, d, J=7.5 Hz), 7.14–7.35 (6H, m), 7.58 (1H, d, J=7.5 Hz), 7.73 (1H, d, J=7.5 Hz), 7.83–7.89 (1H, m), 7.95 (1H, s); MASS (m/z): 370 (M$^+$+1), 86 (bp).

(16) 1-(2-Chlorobenzyl)-2-ethyl-3-formylindole-6-carboxamide mp: 260–261° C.; IR (KBr): 3400, 1685, 1635, 1615, 1390 cm$^{-1}$;

NMR (CDCl$_3$, δ): 1.29 (3H, t, J=7 Hz), 3.08 (2H, q, J=7 Hz), 5.52 (2H, s), 6.29 (1H, d, J=7.5 Hz), 7.07 (1H, t, J=7.5 Hz), 7.24 (1H, t, J=7.5 Hz), 7.49 (1H, d, J=7.5 Hz), 7.69 (1H, d, J=7.5 Hz), 7.86 (1H, s), 8.35 (1H, d, J=7.5 Hz), 10.24 (1H, s); MASS (m/z): 341 (M$^+$+1).

(17) 1-(2-Chlorobenzoyl)-3-isobutyryl-2-propylindole-6-carboxamide mp: 125–126.5° C.; IR (KBr): 1700, 1650 cm$^{-1}$; NMR (CDCl$_3$δ): 0.90 (3H, t, J=7 Hz), 1.28 (6H, d, J=7 Hz), 1.61–1.74 (2H, m), 2.98–3.05 (2H, m), 3.40–3.49 (1H, m), 7.48–7.53 (3H, m), 7.59–7.65 (2H, m), 7.79 (2H, AB, J=8, 7.5 Hz); MASS (m/z): 411 (M$^+$+1), 76 (bp).

(18) 1-(2-Chlorobenzyl)-3-formylindole-6-carboxamide mp: 237–240° C.; NMR (DMSO-d$_6$, δ): 5.68 (2H, s), 6.86 (1H, d, J=8 Hz), 6.25–6.4 (3H, m), 7.58 (1H, d, J=8 Hz), 7.84 (1H, d, J=8 Hz), 7.98 (1H, br s), 8.14 (1H, s), 8.17 (1H, d, J=8 Hz), 8.46 (1H, s), 9.98 (1H, s).

(19) 3-Acetyl-1-(2-chlorobenzyl)-2-methylindole-6-carboxamide mp: 272–276° C.; NMR (DMSO-d$_6$, δ): 2.63 (3H, s), 2.65 (3H, s), 5.61 (2H, s), 6.17 (1H, d, J=8 Hz), 7.18 (1H, t, J=8 Hz), 7.27 (1H, br s), 7.32 (1H, t, J=8 Hz), 7.57 (1H, d, J=8 Hz), 7.80 (1H, d, J=8 Hz), 7.94 (1H, br s), 8.03 (1H, s), 8.11 (1H, s).

(20) 1-(2-Chlorobenzyl)-2-methyl-3-propionylindole-6-carboxamide mp: 215–217° C.;

NMR (DMSO-d$_6$, δ): 1.14 (3H, t, J=7 Hz), 2.64 (3H, s), 3.04 (2H, q, J=7 Hz), 5.62 (2H, s), 6.18 (1H, d, J=8 Hz), 7.18 (1H, t, J=8 Hz), 7.29 (1H, br s), 7.32 (1H, t, J=8 Hz), 7.57 (1H, d, J=8 Hz), 7.79 (1, d, J=8 Hz), 8.02 (1H, s), 8.10 (1H, d, J=8 Hz).

(21) 1-(2-Chlorobenzo[b]thiophen-3-ylmethyl)-3-isobutyryl-2-methylindole-6-carboxamide mp: 255° C. (dec.); NMR (DMSO-d$_6$, δ): 1.13 (6H, d, J=7 Hz), 2.63 (3H, s), 3.47 (1H, m), 5.84 (2H, s), 7.2–7.42 (4H, m), 7.48 (1H, d, J=8 Hz), 7.89 (1H, br s), 7.95–8.0 (2H, m), 8.23 (1H, s).

(22) 1-(Benzothiazol-2-ylmethyl)-2-ethyl-3-isobutyrylindole-6-carboxamide mp: 188–190.5° C. (dec.); NMR (CDCl$_3$, δ): 1.28 (3H, t, J=7 Hz), 1.29 (6H, d, J=7 Hz), 3.27 (2H, q, J=7 Hz), 3.53 (1H, m), 5.82 (2H, s), 7.36 (1H, t, J=8 Hz), 7.49 (1H, t, J=8 Hz), 7.66 (1H, d, J=8 Hz), 7.74 (1H, d, J=8 Hz), 7.97 (1H, d, J=8 Hz), 8.02 (1H, d, J=8 Hz), 8.07 (1H, s).

(23) 1-(Benzo[b]thiophen-5-ylmethyl)-3-isobutyryl-2-propylindole-6-carboxamide mp: 189–192° C. (dec.); NMR (CDCl$_3$, δ): 1.02 (3H, t, J=7 Hz), 1.31 (6H, d, J=7 Hz), 1.62 (2H, m), 3.14 (2H, m), 3.57 (1H, m), 5.58 (2H, s), 7.02 (1H, d, J=8 Hz), 7.18 (1H, d, J=6 Hz), 7.29 (1H, s), 7.43 (1H, d, J=6 Hz), 7.60 (1H, d, J=8 Hz), 7.79 (1H, d, J=8 Hz), 7.92 (1H, s), 7.97 (1H, d, J=8 Hz).

(24) 1-(2,4-Dichlorobenzyl)-3-isobutyryl-2-propylindole-6-carboxamide mp: 191–192° C.; NMR (DMSO-d$_6$, δ): 0.92 (3H, t, J=7 Hz), 1.18 (6H, d, J=7 Hz), 1.45 (2H, sextet, J=7 Hz), 3.00–3.05 (2H, m), 3.55 (2H, septet, J=7 Hz), 5.60 (2H, s), 6.18 (1H, d, J=8 Hz), 7.28 (1H, dd, J=2, 8 Hz), 7.31 (1H, s), 7.76 (1H, d, J=2 Hz), 7.82 (1H, d, J=8 Hz), 7.92 (1H, br s), 7.94 (1H, s), 7.98 (1H, d, J=8 Hz)

(25) 3-Isobutyryl-2-propyl-1-(3-pyridylmethyl)indole-6-carboxamide mp: 230–235° C.; NMR (CDCl$_3$, δ): 1.02 (3H, t, J=7 Hz), 1.30 (6H, d, J=7 Hz), 1.60 (2H, sextet, J=7 Hz), 3.08–3.16 (2H, m), 3.56 (2H, septet, J=7 Hz), 5.48 (2H, s), 7.19–7.24 (2H, m), 7.61 (1H, d, J=8 Hz), 7.92 (1H, s), 7.96 (1H, d, J=8 Hz), 8.38 (1H, d, J=2 Hz), 8.52 (1H, dd, J=, 5 Hz).

(26) 3-Isobutyryl-2-propyl-1-(1-naphthylmethyl)indole-6-carboxamide mp: 202–203° C.; NMR (CDCl$_3$, δ): 0.96 (3H, t, J=7 Hz), 1.34 (6H, d, J=7 Hz), 1.61–1.68 (2H, m), 3.08 (2H, dd, J=7, 8 Hz), 3.61 (1H, septet, J=7 Hz), 5.90 (2H, s), 6.28 (1H, d, J=8 Hz), 7.21 (1H, t, J=8 Hz), 7.58–7.69 (3H, m), 7.76 (1H, d, J=8 Hz), 7.78 (1H, s), 7.94 (1H, d, J=8 Hz), 8.00 (1H, d, J=8 Hz), 8.08 (1H, d, J=8 Hz).

(27) 3-Isobutyryl-2-propyl-!-(2-naphthylmethyl)indole-6-carboxamide mp: 199–190° C.; NMR (CDCl$_3$, δ): 0.98 (3H, t, J=7 Hz), 1.30 (6H, d, J=7 Hz), 1.55–1.68 (2H, m), 3.14–3.18 (2H, m), 3.58 (1H, septet, J=7 Hz), 5.58 (2H, s), 7.15 (1H, dd, J=1, 8 Hz), 7.28 (1H, s), 7.42–7.48 (2H, m), 7.60–7.66 (2H, m), 7.78 (2H, d, J=8 Hz), 7.93 (1H, d, J=1 Hz), 7.98 (1H, d, J=8 Hz).

(28) 1-Allyl-3-isobutyryl-2-propylindole-6-carboxamide mp: 155–158° C.; NMR (CDCl$_3$, δ): 1.06 (3H, t, J=7 Hz), 1.27 (6H, d, J=7 Hz), 1.71 (2H, m), 3.11 (2H, m), 3.51 (1H, m), 4.83 (2H, m), 4.86 (1H, m), 5.19 (1H, m), 5.96 (1H, m), 7.58 (1H, d, J=8 Hz), 7.89 (1H, d, J=8 Hz), 7.96 (1H, s).

(29) 1-(2-Chlorobenzyl)-3-isobutyryl-2-(1-propenyl)indole-6-carboxamide mp: 190–193° C.; NMR (CDCl$_3$, δ): 1.23 (6H, d, J=7 Hz), 1.93 (3H, d, J=7 Hz), 3.51 (1H, m), 5.48 (2H, s), 5.91 (1H, dq, J=15, 7 Hz), 6.41 (1H, d, J=8 Hz), 6.71 (1H, d, J=15 Hz), 7.07 (1H, t, J=8 Hz), 7.23 (1H, d, J=8 Hz), 7.46 (1H, d, J=8 Hz), 7.62 (1H, d, J=8 Hz), 7.80 (1H, s), 8.24 (1H, d, J=8 Hz)

(30) 1-(2-Chlorobenzyl)-2-(1-hydroxypropyl)-3-isobutyrylindole-6-carboxamide mp: 220–223° C.; NMR (CDCl$_3$, δ): 0.94 (3H, t, J=7 Hz), 1.32 (3H, d, J=7 Hz), 1.39 (3H, d, J=7 Hz), 1.52 (1H, m), 1.93 (1H, m), 3.69 (1H, m), 4.68 (1H, m), 5.48 (1H, d, J=17 Hz), 5.66 (1H, d, J=17 Hz), 6.33 (1H, d, J=10 Hz), 6.43 (1H, d, J=8 Hz), 7.07 (1H, t, J=8 Hz), 7.21 (1H, t, J=8 Hz), 7.44 (1H, d, J=8 Hz), 7.68 (1H, d, J=8 Hz), 7.92 (1H, s), 7.96 (1H, d, J=8 Hz).

(31) 1-(2-Chlorobenzyl)-3-(3,3-dimethylbutanoyl)indole-6-carboxamide mp: 202–205° C.; NMR (CDCl$_3$, δ): 1.08 (9H, s), 2.69 (2H, s), 5.50 (2H, s), 6.73 (1H, d, J=8 Hz), 7.14 (1H, t, J=8 Hz), 7.28 (1H, t, J=8 Hz), 7.45 (1H, d, J=8 Hz), 7.62 (1H, d, J=8 Hz), 7.80 (1H, s), 7.99 (1H, s), 8.53 (1H, d, J=8 Hz).

(32) 1-(2-Chlorobenzyl)-2-propylindole-6-carboxamide mp: 174–177° C.; NMR (CDCl$_3$, δ): 1.00 (3H, t, J=7 Hz), 1.74 (2H, m), 2.61 (2H, t, J=7 Hz), 5.43 (2H, s), 6.15 (1H, d, J=8 Hz), 6.44 (1H, s), 7.00 (1H, t, J=8 Hz), 7.18 (1H, t, J=8 Hz), 7.4–7.5 (2H, m), 7.61 (1H, d, J=8 Hz), 7.79 (1H, s).

(33) 1-(2-Bromobenzyl)-2-propylindole-6-carboxamide mp: 166–168° C.; NMR (CDCl$_3$, δ): 1.00 (3H, t, J=7 Hz), 1.73 (2H, m), 2.59 (2H, m), 5.36 (2H, s), 6.10 (1H, d, J=8 Hz), 6.42 (1H, s), 7.0–7.15 (2H, m), 7.46 (1H, dd, J=1, 8 Hz), 7.61 (1H, dd, J=1, 8 Hz), 7.76 (1H, s).

(34) 2-Acetyl-1-(2-chlorobenzyl)-3-methylindole-6-carboxamide mp: 234–236° C.; NMR (DMSO-d$_6$, δ): 2.58 (3H, s), 2.71 (3H, s), 5.79 (2H, s), 6.03 (1H, d, J=8 Hz), 7.09 (1H, t, J=8 Hz), 7.24 (1H, t, J=8 Hz), 7.35 (1H, br s), 7.50 (1H, d, J=8 Hz), 7.70 (1H, d, J=8 Hz), 7.92 (1H, d, J=8 Hz), 7.98 (1H, s), 7.99 (1H, br s).

(35) 2-Chloro-1-(2-chlorobenzyl)-3-ethylindole-6-carboxamide mp: 195–198° C.; NMR (CDCl$_3$, δ): 1.27 (3H, t, J=7 Hz), 2.83 (2H, q, J=7 Hz), 5.49 (2H, s), 6.29 (1H, d, J=8 Hz), 7.03 (1H, t, J=8 Hz), 7.18 (1H, t, J=8 Hz), 7.42 (1H, d, J=8 Hz), 7.50 (1H, d, J=8 Hz), 7.63 (1H, d, J=8 Hz), 7.77 (1H, s).

(36) 1-(2-Chlorobenzyl)-2-propionyl-3-propylindole-6-carboxamide mp: 165–167° C.; NMR (CDCl$_3$, δ): 1.05 (3H, t, J=7 Hz), 1.13 (3H, t, J=7 Hz), 1.76 (2H, m), 2.93 (2H, q, J=7 Hz), 3.08 (2H, m), 5.70 (2H, s), 6.23 (1H, d, J=8 Hz), 6.97 (1H, t, J=8 Hz), 7.12 (1H, t, J=8 Hz), 7.47 l1H, d, J=8 Hz), 7.53 (1H, d, J=8 Hz), 7.74 (1H, s), 7.76 (1H, d, J=8 Hz).

(37) 1-(2-Chlorobenzyl)-2-isobutyryl-3-propylindole-6-carboxamide mp: 159–160.5° C.; NMR (CDCl$_3$, δ): 1.03 (3H, t, J=7 Hz), 1.12 (6H, d, J=7 Hz), 1.76 (2H, m), 3.04 (2H, m), 3.36 (1H, m), 5.66 (2H, s), 6.29 (1H, d, J=8 Hz), 6.99 (1H, t, J=8 Hz), 7.14 (1H, t, J=8 Hz), 7.38 (1H, d, J=8 Hz), 7.56 (1H, d, J=8 Hz), 7.76 (1H, d, J=8 Hz), 7.77 (1H, s).

(38) 1-(2-Chlorobenzyl)-3-(3-oxo-1-butenyl)indole-6-carboxamide mp: 248–250° C.; NMR (DMSO-d$_6$, δ): 2.30 (3H, s), 5.61 (2H, s), 6.74 (1H, d, J=8 Hz), 6.75 (1H, d, J=8 Hz), 7.2–7.4 (3H, m), 7.54 (1H, d, J=8Hz), 7.77 (1H, d, J=8 Hz), 7.80 (1H, d, J=15 Hz), 7.98 (1H, br s), 8.04 (1H, d, J=8 Hz), 8.11 (1H, s), 8.14 (1H, s).

(39) 4-(2-Chlorobenzyl)-3-oxo-1,2,3,4-tetrahydrocyclopent[b]indole-6-carboxamide mp: 289° C. (dec.); NMR (DMSO-d$_6$, δ): 2.95 (2H, m), 3.10 (2H, m), 5.67 (2H, s), 6.37 (1H, d, J=8 Hz), 7.16 (1H, t, J=8 Hz), 7.28 (1H, t, J=8 Hz), 7.40 (1H, br s), 7.53 (1H, d, J=8 Hz), 7.74 (1H, d, J=8 Hz), 7.88 (1H, d, J=8 Hz), 8.01 (1H, br s), 8.07 (1H, s).

(40) 4-(6-Chloro-3,4-methylenedioxybenzyl)-3-oxo-1,2,3,4-tetrahydrocyclopent[b]indole-6-carboxamide mp: 282° C. (dec.); NMR (DMSO-d$_6$, δ): 2.98 (2H, m), 3.09 (2H, m), 5.54 (2H, s), 5.97 (2H, s), 5.96 (1H, s), 7.17 (1H, s), 7.43 (1H, br s), 7.71 (1H, d, J=8 Hz), 7.86 (1H, d, J=8 Hz), 8.03 (1H, br s), 8.05 (1H, s).

(41) 1-[2-Chloro-4-(N-phenylsulfonylcarbamoyl)benzyl]-3-isobutyryl-2-propylindole-6-carboxamide mp: 147–150 ° C.; NMR (DMSO-d$_6$, δ): 0.88 (3H, t, J=7 Hz), 1.18 (6H, d, J=7 Hz), 1.45 (2H, sextet, J=7 Hz), 2.98–3.03 (2H, m), 3.55 (1H, septet, J=7 Hz), 5.68 (2H, s), 6.27 (1H, d, J=8 Hz), 7.28 (1H, s), 7.60–7.64 (3H, m), 7.69 (1H, dd, J=2, 8 Hz), 7.80 (1H, d, J=8 Hz), 7.92–7.96 (4H, m), 8.06 (1H, s).

EXAMPLE 76

The following compound described in (1) to (5) were prepared by a similar manner to that of Example 6.

(1) 1-(6-Chloro-3,4-methylenedioxybenzyl)-3-methoxyacetyl-2-propylindole-6-carboxamide (2) 1-(2-Chlorobenzyl)-3-ethoxyacetyl-2-propylindole-6-carboxamide NMR (DMSO-d$_6$, δ): 0.93 (3H, t, J=7 Hz), 1.18 (3H, t, J=7 Hz), 1.46 (2H, sextet, J=7 Hz), 3.03 (3H, t, J=7 Hz), 3.62 (2H, q, J=7 Hz), 4.74 (2H, s), 5.63 (2H, s), 6.22 (1H, d, J=8 Hz), 7.17 (1H, t, J=8 Hz), 7.30 (1H, s), 7.33 (1H, t, J=8 Hz), 7.58 (1H, d, J=8 Hz), 7.80 (1H, d, J=8 Hz), 7.92 (1H, d, J=8 Hz), 7.94 (1H, s), 8.00 (1H, s).

(3) 1-(2-Chlorobenzyl)-3-isobutyryl-2-propylindole-6-ylacetamide mp: 146–148° C.; IR (KBr): 1715, 1650 cm$^{-1}$; NMR (CDCl$_3$, δ): 1.01 (3H, t, J=7 Hz), 1.30 (6H, d, J=7 Hz), 1.57–1.67 (2H, m), 3.02–3.08 (2H, m), 3.51–3.60 (1H, m), 3.66 (2H, s), 5.45 (2H, s), 6.29 (1H, d, J=7.5 Hz), 7.04–7.09 (2H, m), 7.21 (2H, t, J=7.5 Hz), 7.47 (1H, d, J=7.5 Hz), 7.93 (1H, d, J=7.5 Hz). MASS (m/z): 411(M$^+$+1), 74 (bp).

(4) 1-(6-Chloro-3,4-methylenedioxybenzyl)-3-isobutyryl-2-propylindole-6-ylacetamide mp: 136–138° C.; IR (KBr): 1655, 1505 cm$^{-1}$; NMR (CDCl$_3$, δ): 1.04 (3H, t, J=7 Hz), 1.29 (6H, d, J=7 Hz), 1.55–1.67 (2H, m), 3.01–3.07 (2H, m), 3.50–3.58 (1H, m), 3.69 (2H, s), 5.33 (2H, s), 5.75 (1H, s), 5.90 (2H, s), 6.92 (1H, s), 7.09 (1H, s), 7.19 (1H, d, J=7.5 Hz), 7.91 (1H, d, J=7.5 Hz); MASS (m/z): 455 (M$^+$+1), 74 (bp).

(5) 1-(2-Chlorobenzyl)-3-nitro-2-propylindole-6-carboxamide

NMR (DMSO-d$_6$, δ):0.95 (3H, t, J=7 Hz), 1.54 (2H, sextet, J=7 Hz), 3.13–3.17 (2H, m), 5.72 (2H, s), 6.44 (1H, d, J=8 Hz), 7.20 (1H, t, J=8 Hz), 7.36 (1H, t, J=8 Hz), 7.42 (1H, s), 7.60 (1H, d, J=8 Hz), 7.96 (1H, d, J=8 Hz), 8.03 (1H, s), 8.10 (1H, s), 8.22 (1H, d, J=8 Hz).

EXAMPLE 77

The following compounds described in (1) to (13) were prepared in a similar manner to that of Example 26.

(1) 1-(4-Chloro-2-fluorobenzyl)-3-methoxyacetyl-2-propylindole-6-carboxamide mp: 192–193° C.; NMR (DMSO-d$_6$, δ): 0.94 (3H, t, J=7 Hz), 1.44 (2H, sextet, J=7 Hz), 3.09 (2H, t, J=7 Hz), 3.41 (3H, s), 4.69 (2H, s), 5.64 (2H, s), 6.50 (1H, t, J=8 Hz), 7.18 (1H, dd, J=2, 8 Hz), 7.33 (1H, s), 7.55 (1H, dd, J=2, 8 Hz), 7.79 (1H, d, J=8 Hz), 7.89 (1H, d=8 Hz), 7.92 (1H, s), 8.06 (1H, s).

(2) 1-(2,4-Dichlorobenzyl)-3-methoxyacetyl-2-propylindole-6-carboxamide mp: 203–205° C.; NMR (DMSO-d$_6$, δ): 0.94 (3H, t, J=7 Hz), 1.98 (2H, sextet, J=7 Hz), 3.04 (2H, t, J=7 Hz), 3.42 (3H, s), 4.71 (2H, s), 5.60 (2H, s), 6.20 (1H, d, J=8 Hz), 7.27 (1H, dd, J=2, 8 Hz), 7.32 (1H, s), 7.77 (1H, d, J=2 Hz), 7.82 (1H, d, J=8 Hz), 7.92 (1H, d, J=8 Hz), 7.94 (1H, s), 7.98 (1H, s).

(3) 1-(4-Bromo-2-chlorobenzyl)-3-methoxyacetyl-2-propylindole-6-carboxamide mp: 178–180° C.;

NMR (DMSO-d$_6$, δ): 0.94 (3H, t, J=7 Hz), 1.48 (2H, sextet, J=7 Hz), 3.04 (2H, t, J=7 Hz), 3.42 (3H, s), 4.68 (2H, s), 5.57 (2H, s), 6.13 (1H, d, J=8 Hz), 7.30 (1H, s), 7.38 (1H, dd, J=2, 8 Hz), 7.80 (1H, d, J=8 Hz), 7.86 (1H, d, J=2 Hz), 7.90 (1H, d, J=8 Hz), 7.93 (1H, s), 7.97 (1H, s).

(4) 1-(4-Bromo-2-fluorobenzyl)-3-methoxyacetyl-2-propylindole-6-carboxamide mp: 197–199° C.; NMR (DMSO-d$_6$, δ): 0.94 (3H, t, J=7 Hz), 1.48 (2H, sextet, J=7 Hz), 3.09 (2H, t, J=7 Hz), 3.40 (3H, s), 4.67 (2H, s), 5.62 (2H, s), 6.43 (1H, d, J=8 Hz), 7.28 (1H, dd, J=2, 8 Hz), 7.65 (1H, dd, J=2, 6 Hz), 7.78 (1H, d, J=8 Hz), 7.90 (1H, d, J=8 Hz), 7.92 (1H, s), 8.05 (1H, s).

(5) 1-(2-Chloro-4-fluorobenzyl)-3-methoxyacetyl-2-propylindole-6-carboxamide mp: 174–176° C.; NMR (DMSO-d$_6$, δ): 0.93 (3H, t, J=7 Hz), 1.48 (2H, sextet, J=7 Hz), 3.04 (2H, t, J=7 Hz), 3.42 (3H, s), 4.70 (2H, s), 5.58 (2H, s), 6.25 (1H, d, J=8 Hz), 7.06 (1H, dt, J=2, 8 Hz), 7.32 (1H, s), 7.50 (1H, dd, J=2, 8 Hz), 7.80 (1H, d, J=8 Hz), 7.92 (1H, d, J=8 Hz), 7.94 (1H, s), 8.00 (1H, s).

(6) 1-(Benzo[b]thiophen-5-ylmethyl)-3-methoxyacetyl-2-propylindole-6-carboxamide mp: 197–199° C. (dec.); NMR (DMSO-d$_6$, δ): 0.92 (3H, t, J=7 Hz), 1.48 (2H, sextet, J=7 Hz), 3.14 (2H, t, J=7 Hz), 3.42 (3H, s), 4.72 (2H, s), 5.74 (2H, s), 7.10 (1H, d, J=8 Hz), 7.28 (1H, s), 7.38 (1H, d, J=5 Hz), 7.44 (1H, s), 7.75 (1H, d, J=5 Hz), 7.78 (1H, d, J=8 Hz), 7.88 (1H, d, J=8 Hz), 7.92 (1H, s), 7.96 (1H, d, J=8 Hz), 8.12 (1H, s).

(7) Methyl 1-(2,4-dichlorobenzyl)-3-isobutyryl-2-propylindole-6-carboxylate

NMR (CDCl₃, δ): 1.02 (3H, t, J=7 Hz), 1.31 (6H, d, J=7 Hz), 1.60 (2H, sextet, J=7 Hz), 3.06 (2H, t, J=7 Hz), 3.58 (2H, septet, J=7 Hz), 3.93 (3H, s), 5.46 (2H, s), 6.16 (1H, d, J=8 Hz), 7.04 (1H, d, J=8 Hz), 7.50 (1H, s), 7.90 (1H, s), 7.96 (2H, s).

(8) Methyl 3-isobutyryl-2-propyl-1-(3-pyridylmethyl)indole-6-carboxylate

NMR (CDCl₃, δ): 1.02 (3H, t, J=7 Hz), 1.30 (6H, d, J=7 Hz), 1.60 (2H, sextet, J=7 Hz), 3.12 (2H, t, J=7 Hz), 3.56 (2H, septet, J=7 Hz), 3.92 (3H, s), 5.48 (2H, s), 7.14–7.23 (2H, m), 7.92–7.95 (2H, m), 7.98 (1H, s), 8.42 (1H, d, J=2 Hz), 8.54 (1H, d, J=5 Hz).

(9) Methyl 3-isobutyryl-2-propyl-1-(1-naphthylmethyl)indole-6-carboxylate

NMR (CDCl₃, δ): 0.97 (3H, t, J=7 Hz), 1.34 (6H, d, J=7 Hz), 1.64 (2H, sextet, J=7 Hz), 3.04–3.10 (2H, m), 3.63 (1H, septet, J=7 Hz), 3.84 (3H, s), 5.92 (2H, s), 6.28 (1H, d, J=8 Hz), 7.22 (1H, t, J=8 Hz), 7.62 (1H, t, J=8 Hz), 7.69 (1H, t, J=8 Hz), 7.77 (1H, d, J=8 Hz), 7.77 (2H, s), 7.92 (1H, s).

(10) Methyl 3-isobutyryl-2-propyl-1-(2-naphthylmethyl)indole-6-carboxylate

NMR (CDCl₃, δ): 1.00 (3H, t, J=7 Hz), 1.32 (6H, d, J=7 Hz), 1.55–1.68 (2H, m), 3.13–3.18 (2H, m), 3.60 (1H, septet, J=7 Hz), 3.88 (3H, s), 5.62 (2H, s), 7.17 (1H, d, J=8 Hz), 7.29 (2H, s), 7.42–7.48 (2H, m), 7.64–7.68 (1H, m), 7.80 (2H, d, J=2 Hz), 7.96 (2H, s), 8.04 (1H, s).

(11) Methyl 1-(6-chloro-3,4-methylenedioxybenzyl)-3-methoxyacetyl-2-propylindole-6-carboxylate NMR (CDCl₃, δ): 1.04 (3H, t, J=7 Hz), 1.56–1.72 (2H, m), 3.06–3.13 (2H, m), 3.58 (3H, s), 3.93 (3H, s), 4.73 (2H, s), 5.40 (2H, s), 5.70 (1H, s), 5.38 (2H, s), 6.92 (1H, s), 7.63 (1H, d, J=8 Hz), 7.96 (1H, s), 7.98 (1H, d, J=8 Hz).

(12) Methyl 1-(2-chlorobenzyl)-3-ethoxyacetyl-2-propylindole-6-carboxylate

NMR (CDCl₃, δ): 1.03 (3H, t, J=7 Hz), 1.34 (3H, t, J=7 Hz), 1.56–1.70 (2H, m), 3.10 (3H, t, J=7 Hz), 3.77 (2H, q, J=7 Hz), 3.92 (3H, s), 4.79 (2H, s), 5.52 (2H, s), 6.24 (1H, d, J=8 Hz), 7.03 (1H, t, J=8 Hz), 7.22 (1H, t, J=3 Hz), 7.46 (1H, d, J=8 Hz), 7.85 (1H, d, J=8 Hz), 7.92 (1H, s), 7.98 (1H, d, J=8 Hz).

(13) 1-(2-Chloro-4-methoxycarbonylbenzoyl)-3-isobutyryl-2-propylindole-6-carboxamide NMR (CDCl₃, δ): 1.01 (3H, t, J=7 Hz), 1.32 (6H, d, J=7 Hz), 1.60 (2H, sextet, J=7 Hz), 3.02–3.06 (2H, m), 3.56 (1H, septet, J=7 Hz), 3.90 (3H, s), 5.53 (2H, s), 6.28 (1H, d, J=8 Hz), 7.63 (1H, d, J=8 Hz), 7.69 (1H, d, J=8 Hz), 7.82 (1H, s), 7.98 (1H, d, J=8 Hz), 8.14 (1H, s).

It will be understood that various changes and modifications can be made in the details of procedure, formulation and use without departing from the spirit of the invention, especially as defined in the following claims.

We claim:

1. A method of treating a mammal having precancerous lesions comprising administering a pharmacologically effective amount of a compound of Formula I or pharmaceutically acceptable salt thereof:

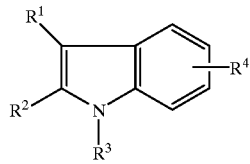

wherein $R^1$ is selected from the group consisting of hydrogen, halogen, nitro, carboxy, protected carboxy, acyl, cyano, hydroxyimino(lower)alkyl, lower alkenyl optionally substituted with oxo, or lower alkyl optionally substituted with protected carboxy, carboxy or hydroxy;

$R^2$ is selected from the group consisting of hydrogen, halogen, lower alkenyl, acyl, or lower alkyl optionally substituted with protected carboxy, carboxy, lower alkoxy, or hydroxy, alternatively, $R^1$ and $R^2$, together with the carbon atoms to which they are attached form a 4- to 7-membered carbocyclic ring optionally substituted with oxo;

$R^3$ is selected from the group consisting of lower alkenyl or lower alkyl, both of which are optionally substituted with one or more substituent(s) selected from the group consisting of (1) oxo, (2) aryl optionally substituted with one or more substituents selected from the group consisting of halogen, aryl, lower alkoxy, lower aklylenedioxy, cyano, nitro, carboxy, protected carboxy, acyl, and amino optionally substituted with acyl or protected carboxy, and (3) a heterocyclic group optionally substituted with halogen; and $R^4$ is selected from the group consisting of carboxy, protected carboxy, acyl, cyano, halogen, a heterocyclic group, amino optionally substituted with acyl or protected carboxy, or lower alkyl optionally substituted with protected carboxy, carboxy, or acyl;

or its pharmaceutically acceptable salt.

2. The method of claim 1, wherein $R^1$ is selected from the group consisting of cyano, acyl, or lower alkyl optionally substituted with hydroxy; $R^2$ is selected from the group consisting of hydrogen, acyl, lower alkenyl, or lower alkyl optionally substituted with lower alkoxy or hydroxy; $R^3$ is methyl substituted with aryl or a heterocyclic group, wherein aryl is optionally substituted with one or more substituent selected from the group consisting of halogen, lower alkylenedioxy, protected carboxy and carboxy; or $R^1$ and $R^2$ together with the carbon atoms to which they are attached represent a 4- to 7-membered carbocyclic ring optionally substituted with oxo; and $R^4$ is selected from the group consisting of acyl, cyano, or a heterocyclic group.

3. The method of claim 2, wherein $R^1$ is selected from the group consisting of lower alkyl, or lower alkanoyl optionally substituted with hydroxy, lower alkoxy, or aryl; $R^2$ is selected from the group consisting of hydrogen, lower alkenyl, or lower alkyl optionally substituted with lower alkoxy; and $R^3$ is benzyl optionally substituted with one or more substituent(s) selected from the group consisting of halogen and lower alkylenedioxy.

4. The method of claim 3, wherein $R^4$ is —C(O)NR⁵R⁶ wherein $R^5$ is selected from the group consisting of hydrogen or lower alkyl, and $R^6$ is selected from the group consisting of hydrogen, hydroxy, lower alkoxy, arylsulfonyl, a heterocyclic group, or lower alkyl optionally substituted with lower cycloalkyl or a heterocyclic group; or $R^5$ and $R^6$, together with the nitrogen atom to which they are attached, may represent a heterocyclic group.

5. The method of claim 4 wherein $R^1$ is lower alkanoyl optionally substituted with alkoxy; $R^2$ is lower alkyl; and $R^4$ is carbamoyl.

6. A method for inhibiting the growth of neoplastic cells comprising exposing the cells to a growth inhibiting effective amount of a compound of Formula I or pharmaceutically acceptable salt thereof:

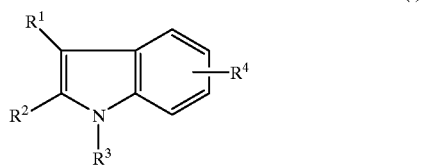

(I)

Wherein $R^1$ is selected from the group consisting of cyano, acyl, or lower alkyl optionally substituted with hydroxy; $R^2$ is selected from the group consisting of hydrogen, acyl, lower alkenyl, or lower alkyl optionally substituted with lower alkoxy or hydroxy; $R^3$ is methyl substituted with aryl or a heterocyclic group, wherein aryl is optionally substituted with one or more substituent selected from the group consisting of halogen, lower alkylenedioxy, protected carboxy and carboxy; or $R^1$ and $R^2$ together with the carbon atoms to which they are attached represent a 4- to 7-membered carbocyclic ring optionally substituted with oxo; and $R^4$ is selected from the group consisting of acyl, cyano, or a heterocyclic group.

7. The method of claim 6, wherein, $R^1$ is selected from the group consisting of lower alkyl, or lower alkanoyl optionally substituted with hydroxy, lower alkoxy, or aryl; $R^2$ is selected from the group consisting of hydrogen, lower alkenyl, or lower alkyl optionally substituted with lower alkoxy; and $R^3$ is benzyl optionally substituted with one or more substituent(s) selected from the group consisting of halogen and lower alkylenedioxy.

8. The method of claim 7, wherein $R^4$ is —C(O)NR$^5$R$^6$ wherein $R^5$ is selected from the group consisting of hydrogen or lower alkyl, and $R^6$ is selected from the group consisting of hydrogen, hydroxy, lower alkoxy, arylsulfonyl, a heterocyclic group, or lower alkyl optionally substituted with lower cycloalkyl or a heterocyclic group; or $R^5$ and $R^6$, together with the nitrogen atom to which they are attached, may represent a heterocyclic group.

9. The method of claim 8 wherein $R^1$ is lower alkanoyl optionally substituted with alkoxy; $R^2$ is lower alkyl; and $R^4$ is carbamoyl.

10. A method for regulating apoptosis in human cells comprising exposing said cells to an effective amount of a compound of the formula:

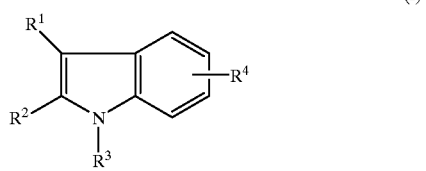

(I)

wherein $R^1$ is selected from the group consisting of hydrogen, halogen, nitro, carboxy, protected carboxy, acyl, cyano, hydroxyimino(lower)alkyl, lower alkenyl optionally substituted with oxo, or lower alkyl optionally substituted with protected carboxy, carboxy or hydroxy;

$R^2$ is selected from the group consisting of hydrogen, halogen, lower alkenyl, acyl, or lower alkyl optionally substituted with protected carboxy, carboxy, lower alkoxy, or hydroxy, or $R^1$ and $R^2{}_1$ together with the carbon atoms to which they are attached form a 4- to 7-membered carbocyclic ring optionally substituted with oxo;

$R^3$ is selected from the group consisting of lower alkenyl or lower alkyl, both of which are optionally substituted with one or more substituent(s) selected from the group consisting of (1) oxo, (2) aryl optionally substituted with one or more substituents selected from the group consisting of halogen, aryl, lower alkoxy, lower aklylenedioxy, cyano, nitro, carboxy, protected carboxy, acyl, and amino optionally substituted with acyl or protected carboxy, and (3) a heterocyclic group optionally substituted with halogen; and $R^4$ is selected from the group consisting of carboxy, protected carboxy, acyl, cyano, halogen, a heterocyclic group, amino optionally substituted with acyl or protected carboxy, or lower alkyl optionally substituted with protected carboxy, carboxy, or acyl;

or its pharmaceutically acceptable salt.

11. The method of claim 10, wherein $R^1$ is selected from the group consisting of cyano, acyl, or lower alkyl optionally substituted with hydroxy; $R^2$ is selected from the group consisting of hydrogen, acyl, lower alkenyl, or lower alkyl optionally substituted with lower alkoxy or hydroxy; $R^3$ is methyl substituted with aryl or a heterocyclic group, wherein aryl is optionally substituted with one or more substituent selected from the group consisting of halogen, lower alkylenedioxy, protected carboxy and carboxy; or $R^1$ and $R^2$ together with the carbon atoms to which they are attached represent a 4- to 7-membered carbocyclic ring optionally substituted with oxo; and $R^4$ is selected from the group consisting of acyl, cyano, or a heterocyclic group.

12. The method of claim 11, wherein, $R^1$ is selected from the group consisting of lower alkyl, or lower alkanoyl optionally substituted with hydroxy, lower alkoxy, or aryl; $R^2$ is selected from the group consisting of hydrogen, lower alkenyl, or lower alkyl optionally substituted with lower alkoxy; and $R^3$ is benzyl optionally substituted with one or more substituent(s) selected from the group consisting of halogen and lower alkylenedioxy.

13. The method of claim 12, wherein $R^4$ is —C(O)NR$^5$R$^6$ wherein $R^5$ is selected from the group consisting of hydrogen or lower alkyl, and $R^6$ is selected from the group consisting of hydrogen, hydroxy, lower alkoxy, arylsulfonyl, a heterocyclic group, or lower alkyl optionally substituted with lower cycloalkyl or a heterocyclic group; or $R^5$ and $R^6$, together with the nitrogen atom to which they are attached, may represent a heterocyclic group.

14. The method of claim 13 wherein $R^1$ is lower alkanoyl optionally substituted with alkoxy; $R^2$ is lower alkyl; and $R^4$ is carbamoyl.

* * * * *